US011028449B2

(12) United States Patent
Knight et al.

(10) Patent No.: US 11,028,449 B2
(45) Date of Patent: *Jun. 8, 2021

(54) MICROBIOME BASED SYSTEMS, APPARATUS AND METHODS FOR MONITORING AND CONTROLLING INDUSTRIAL PROCESSES AND SYSTEMS

(71) Applicant: Biota Technology, Inc., Oakland, CA (US)

(72) Inventors: Rob Knight, San Diego, CA (US); Ajay Kshatriya, Oakland, CA (US); Chris Lauber, Boulder, CO (US); J. Gregory Caporaso, Flagstaff, AZ (US); Dan Knights, St. Paul, MN (US); Ryan Gill, Denver, CO (US); Joel Moxley, Highlands Ranch, CO (US)

(73) Assignee: Biota Technology, Inc., San Diego, CA (US)

( * ) Notice: Subject to any disclaimer, the term of this patent is extended or adjusted under 35 U.S.C. 154(b) by 667 days.

This patent is subject to a terminal disclaimer.

(21) Appl. No.: 14/585,078

(22) Filed: Dec. 29, 2014

(65) Prior Publication Data

US 2015/0284810 A1 Oct. 8, 2015

Related U.S. Application Data

(60) Provisional application No. 61/922,734, filed on Dec. 31, 2013, provisional application No. 61/944,961, filed on Feb. 26, 2014.

(51) Int. Cl.
C12Q 1/6888 (2018.01)
G16B 10/00 (2019.01)
G16B 20/00 (2019.01)
C12Q 1/689 (2018.01)
C09K 8/582 (2006.01)
E21B 43/16 (2006.01)
E21B 47/11 (2012.01)

(52) U.S. Cl.
CPC .......... C12Q 1/6888 (2013.01); C09K 8/582 (2013.01); C12Q 1/689 (2013.01); E21B 43/16 (2013.01); E21B 47/11 (2020.05); G16B 10/00 (2019.02); G16B 20/00 (2019.02); C12Q 2600/156 (2013.01)

(58) Field of Classification Search
None
See application file for complete search history.

(56) References Cited

U.S. PATENT DOCUMENTS

| 5,593,883 | A | 1/1997 | Cano |
| 6,543,535 | B2 | 4/2003 | Converse et al. |
| 9,771,795 | B2 | 9/2017 | Knight et al. |
| 10,767,476 | B2 | 9/2020 | Knight et al. |
| 2001/0045279 | A1 | 11/2001 | Converse et al. |
| 2006/0154306 | A1 | 7/2006 | Kotlar et al. |
| 2008/0082469 | A1 | 4/2008 | Wilkinson et al. |
| 2010/0081184 | A1 | 4/2010 | Downey et al. |
| 2010/0216219 | A1 | 8/2010 | Hendrickson et al. |
| 2011/0067856 | A1 | 3/2011 | Kohr |
| 2011/0250582 | A1 | 10/2011 | Gates et al. |
| 2011/0308790 | A1 | 12/2011 | Strapoc et al. |
| 2012/0165215 | A1 | 6/2012 | Andersen et al. |
| 2012/0214713 | A1 | 8/2012 | Mu et al. |
| 2012/0252775 | A1 | 10/2012 | Finegold |
| 2012/0253770 | A1 | 10/2012 | Stern et al. |
| 2012/0308988 | A1 | 12/2012 | Discenzo |
| 2012/0310614 | A1 | 12/2012 | Beattie |
| 2013/0121968 | A1 | 5/2013 | Quay |
| 2014/0288853 | A1 | 9/2014 | Dreyfus et al. |
| 2014/0378319 | A1 | 12/2014 | Regberg et al. |
| 2015/0053407 | A1 | 2/2015 | Voordouw et al. |
| 2015/0284811 | A1 | 10/2015 | Knight et al. |
| 2016/0011203 | A1 | 1/2016 | Martin et al. |
| 2016/0232311 | A1 | 8/2016 | Segal et al. |
| 2016/0283651 | A1 | 9/2016 | Knight et al. |
| 2016/0290132 | A1 | 10/2016 | Knight et al. |
| 2017/0139078 | A1 | 5/2017 | Knight et al. |
| 2017/0370213 | A1 | 12/2017 | Knight et al. |
| 2021/0010370 | A1 | 1/2021 | Knight et al. |

FOREIGN PATENT DOCUMENTS

| WO | WO-2011098770 A1 | 8/2011 |
| WO | WO-2015103165 A1 | 7/2015 |
| WO | WO-2015103332 A2 | 7/2015 |
| WO | WO-2015103332 A3 | 7/2015 |

OTHER PUBLICATIONS

Blieck et al. Applied and Environmental Microbiology vol. 73, No. 3, Feb. 2007.*
"U.S. Appl. No. 15/087,552, Non Final Office Action dated Oct. 31, 2016", 24 pgs.
Chikere, et al., "Monitoring of microbial hydrocarbon remediation in the soil", 2011.
Rshedi, Hamid, et al., "Chapter 3: Microbial Enhanced Oil Recovery", Introduction to Enhanced Oil Recovery (EOR) Processes and Bioremediation of Oil-Contaminated Sites [Online]. Retrieved from the Internet: <URL: http://www.intechopen.com/books/introduction-to-enhanced-oil-recovery-eor-processes-and-bioremediation-of-oi, CC BY 3.0 license, (May 23, 2012), 73-88.
Soh, Jung, et al., "Phoenix 2: A locally installable large-scale 16S rRNA gene sequence analysis pipeline with Web interface", Journal of Biotechnology 167(4), (Sep. 20, 2013). 393-403.
Wooley, "A Primer on Metagenomics", (2010), 13 pgs.
"U.S. Appl. No. 14/586,865, Response filed Apr. 16, 2018 to Non Final Office Action dated Dec. 15, 2017", 32 pgs.

(Continued)

Primary Examiner — Joseph Woitach
(74) Attorney, Agent, or Firm — Schwegman Lundberg & Woessner, P.A.

(57) ABSTRACT

There are provided methods, systems and processes for the utilization of microbial and related genetic information for use in industrial settings, such as the exploration, determination, and recovery of natural resources, minerals, and energy sources, the monitoring and analysis of processes, activities, and materials transmission.

20 Claims, 12 Drawing Sheets

Specification includes a Sequence Listing.

(56) References Cited

OTHER PUBLICATIONS

"European Application Serial No. 14876039.0, Extended European Search Report dated Jan. 10, 2018", 12 pgs.

"U.S. Appl. No. 14/586,865, Non Final Office Action dated Dec. 15, 2017", 23 pgs.

"U.S. Appl. No. 15/641,965, Preliminary Amendment filed Sep. 19, 2017", 7 pgs.

"U.S. Appl. No. 14/586,865, Non Final Office Action dated Dec. 21, 2018", 15 pgs.

"U.S. Appl. No. 15/087,497, Non Final Office Action dated Dec. 14, 2018", 13 pgs.

"U.S. Appl. No. 15/087,552, Examiner Interview Summary dated Dec. 29, 2016", 6 pgs.

"U.S. Appl. No. 15/087,552, Supplemental Preliminary Amendment filed Jun. 20, 2016", 4 pgs.

"U.S. Appl. No. 15/340,419, Response filed Mar. 25, 2019 to Restriction Requirement dated Jan. 25, 2019", 6 pgs.

"U.S. Appl. No. 15/340,419, Restriction Requirement dated Jan. 25, 2019", 8 pgs.

"U.S. Appl. No. 15/586,865, Response filed Mar. 21, 2019 to Non Final Office Action dated Dec. 21, 2018", 12 pgs.

"International Application Serial No. PCT/US2014/072607, Response filed Oct. 30, 2015 to Written Opinion dated May 15, 2015", 51 pgs.

Magot, et al., "Microbiology of petroleum reservoirs", Antonie van Leeuwenhoek 77, (2000), 103-116 pgs.

"U.S. Appl. No. 14/586,865, Response filed Sep. 30, 2019 to Final Office Action dated Jun. 28, 2019", 18 pgs.

"U.S. Appl. No. 14/586,865, Final Office Action dated Jun. 28, 2019", 15 pgs.

"U.S. Appl. No. 15/087,497, Final Office Action dated Aug. 22, 2019", 17 pgs.

"U.S. Appl. No. 15/087,497, Response filed May 9, 2019 to Non Final Office Action dated Dec. 14, 2018", 11 pgs.

"U.S. Appl. No. 15/340,419, Non Final Office Action dated Jun. 27, 2019", 16 pgs.

"U.S. Appl. No. 15/340,419, Response filed Sep. 27, 2019 to Non-Final Office Action dated Jun. 27, 2019", 18 pgs.

"U.S. Appl. No. 15/641,965, Response filed Oct. 7, 2019 to Restriction Requirement dated Aug. 7, 2019", 13 pgs.

"U.S. Appl. No. 15/641,965, Restriction Requirement dated Aug. 7, 2019", 6 pgs.

"European Application Serial No. 14876039.0, Response filed Sep. 20, 2019 to Invitation pursuant to Rule 137(4) EPC and Article 94(3) EPC dated May 3, 2019", 28 pgs.

"U.S. Appl. No. 15/087,497, Response filed Nov. 22, 2019 to Final Office Action dated Aug. 22, 2019", 18 pgs.

"U.S. Appl. No. 15/087,497, Advisory Action dated Dec. 4, 2019", 3 pgs.

"U.S. Appl. No. 15/641,965, Non Final Office Action dated Dec. 12, 2019", 15 pgs.

"U.S. Appl. No. 15/340,419, Final Office Action dated Jan. 10, 2020", 18 pgs.

"U.S. Appl. No. 15/641,965, Response filed Mar. 6, 2020 to Non Final Office Action dated Dec. 12, 2019", 27 pgs.

"European Application Serial No. 14876039.0, Communication Pursuant to Article 94(3) EPC dated Feb. 6, 2020", 6 pgs.

"U.S. Appl. No. 15/087,497, Notice of Allowance dated Dec. 9, 2020", 13 pgs.

"U.S. Appl. No. 14/586,865, Response filed Oct. 12, 2020 to Non Final Office Action dated Jun. 12, 2020", 24 pgs.

"U.S. Appl. No. 16/943,631, Preliminary Amendment filed Oct. 7, 2020", 7 pgs.

"U.S. Appl. No. 15/340,419, Non Final Office Action dated Sep. 23, 2020", 11 pgs.

"U.S. Appl. No. 14/586,865, Examiner Interview Summary dated Jun. 29, 2020", 3 pgs.

"U.S. Appl. No. 14/586,865, Non Final Office Action dated Jun. 12, 2020", 25 pgs.

"U.S. Appl. No. 15/087,497, Examiner Interview Summary dated Sep. 4, 2020", 3 pgs.

"U.S. Appl. No. 15/087,497, Non Final Office Action dated Aug. 3, 2020", 15 pgs.

"U.S. Appl. No. 15/087,497, Response filed Aug. 31, 2020 to Non Final Office Action dated Aug. 3, 2020", 12 pgs.

"U.S. Appl. No. 15/340,419, Response filed Apr. 10, 2020 to Final Office Action dated Jan. 10, 2020", 21 pgs.

"U.S. Appl. No. 15/641,965, 312 Amendment filed Jul. 29, 2020", 7 pgs.

"U.S. Appl. No. 15/641,965, Notice of Allowability dated May 8, 2020", 11 pgs.

"U.S. Appl. No. 15/641,965, Notice of Allowability dated Aug. 12, 2020", 2 pgs.

"U.S. Appl. No. 15/641,965, Notice of Allowability dated Aug. 18, 2020", 2 pgs.

"U.S. Appl. No. 15/641,965, Notice of Allowance dated Apr. 29, 2020", 14 pgs.

"U.S. Appl. No. 15/641,965, PTO Response to Rule 312 Communication dated Jul. 30, 2020", 2 pgs.

"U.S. Appl. No. 14/586,865, Final Office Action dated Aug. 10, 2018", 15 pgs.

"U.S. Appl. No. 15/087,497, Examiner Interview Summary dated Aug. 10, 2018", 3 pgs.

"U.S. Appl. No. 15/087,497, Response filed Sep. 5, 2018 to Restriction Requirement dated Jul. 5, 2018.pdf", 8 pgs.

"U.S. Appl. No. 15/087,497, Restriction Requirement dated Jul. 5, 2018", 8 pgs.

"U.S. Appl. No. 15/340,419, Examiner Interview Summary dated Jan. 12, 2021", 3 pgs.

"U.S. Appl. No. 15/340,419, Response filed Jan. 25, 2021 to Non Final Office Action dated Sep. 23, 2020", 9 pgs.

U.S. Appl. No. 14/586,865, filed Dec. 30, 2014, Microbiome Based Systems, Apparatus and Methods for the Exploration and Production of Hydrocarbons.

U.S. Appl. No. 15/087,552, U.S. Pat. No. 9,771,95, filed Mar. 31, 2016, Microbiome Based Systems, Apparatus and Methods for the Exploration and Production of Hydrocarbons.

U.S. Appl. No. 15/087,497, filed Mar. 31, 2016, Microbiome Based Systems, Apparatus and Methods for the Exploration and Production of Hydrocarbons.

U.S. Appl. No. 15/641,965, filed Jul. 5, 2017, Microbiome Based Systems, Apparatus and Methods for the Exploration and Production of Hydrocarbons.

U.S. Appl. No. 15/340,419, filed Nov. 1, 2016, Microbiome Based Systems, Apparatus and Methods for the Exploration and Production of Hydrocarbons.

* cited by examiner

FIG. 6

| | IT2 | HI3 | MD2 | CA1 | PE5 | CO1 | DF3 | PE1 | SP2 | CO3 | SA2 | CM1 |
|---|---|---|---|---|---|---|---|---|---|---|---|---|
| CM1 | 0.779 | 0.727 | 0.809 | 0.703 | 0.866 | 0.781 | 0.834 | 0.858 | 0.829 | 0.742 | 0.705 | 0.000 |
| SA2 | 0.779 | 0.749 | 0.735 | 0.858 | 0.865 | 0.756 | 0.834 | 0.860 | 0.837 | 0.703 | 0.000 | 0.705 |
| CO3 | 0.729 | 0.735 | 0.763 | 0.861 | 0.813 | 0.707 | 0.788 | 0.824 | 0.785 | 0.000 | 0.703 | 0.742 |
| SP2 | 0.734 | 0.734 | 0.869 | 0.812 | 0.738 | 0.772 | 0.691 | 0.717 | 0.000 | 0.785 | 0.837 | 0.829 |
| PE1 | 0.759 | 0.840 | 0.882 | 0.858 | 0.636 | 0.839 | 0.873 | 0.000 | 0.717 | 0.824 | 0.860 | 0.858 |
| DF3 | 0.703 | 0.780 | 0.868 | 0.829 | 0.888 | 0.764 | 0.000 | 0.873 | 0.691 | 0.788 | 0.834 | 0.834 |
| CO1 | 0.702 | 0.742 | 0.797 | 0.709 | 0.846 | 0.000 | 0.764 | 0.839 | 0.772 | 0.707 | 0.756 | 0.781 |
| PE5 | 0.771 | 0.845 | 0.888 | 0.864 | 0.000 | 0.846 | 0.888 | 0.836 | 0.736 | 0.813 | 0.865 | 0.866 |
| CA1 | 0.758 | 0.705 | 0.747 | 0.000 | 0.864 | 0.709 | 0.829 | 0.858 | 0.812 | 0.691 | 0.858 | 0.703 |
| MD2 | 0.840 | 0.814 | 0.000 | 0.747 | 0.888 | 0.797 | 0.868 | 0.882 | 0.869 | 0.763 | 0.735 | 0.809 |
| HI3 | 0.726 | 0.000 | 0.814 | 0.705 | 0.845 | 0.742 | 0.780 | 0.840 | 0.734 | 0.735 | 0.749 | 0.727 |
| IT2 | 0.000 | 0.726 | 0.840 | 0.758 | 0.771 | 0.702 | 0.703 | 0.759 | 0.734 | 0.729 | 0.779 | 0.779 |

SEQUENCE LISTING

<160> NUMBER OF SEQ ID NOS: 65

<210> SEQ ID NO 1
<211> LENGTH: 60
<212> TYPE: DNA
<213> ORGANISM: Artificial Sequence
<220> FEATURE:

<223> OTHER INFORMATION: Primer

<400> SEQUENCE: 1
aatgatacgg cgaccaccga gatctacact atggtaattg tgtgccagcm gccgcggtaa    60

<210> SEQ ID NO 2
<211> LENGTH: 68
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (25)..(36)
<223> OTHER INFORMATION: n is a, c, g, or t

<400> SEQUENCE: 2
caagcagaag acggcatacg agatnnnnnn nnnnnnagtc agtcagccgg actachvggg    60 twtctaat    68

<210> SEQ ID NO 3
<211> LENGTH: 31
<212> TYPE: DNA
<213> ORGANISM: Artificial Sequence
<220> FEATURE:
<223> OTHER INFORMATION: Primer

<400> SEQUENCE: 3
tatggtaatt gtgtgccagc mgccgcggta a    31

<210> SEQ ID NO 4
<211> LENGTH: 32
<212> TYPE: DNA
<213> ORGANISM: Artificial Sequence
<220> FEATURE:
<223> OTHER INFORMATION: Primer

<400> SEQUENCE: 4
agtcagtcag ccggactach vgggtwtcta at    32

<210> SEQ ID NO 5
<211> LENGTH: 32
<212> TYPE: DNA
<213> ORGANISM: Artificial Sequence
<220> FEATURE:
<223> OTHER INFORMATION: Primer

<400> SEQUENCE: 5
attagawacc cbdgtagtcc ggctgactga ct    32

<210> SEQ ID NO 6
<211> LENGTH: 41
<212> TYPE: DNA
<213> ORGANISM: Artificial Sequence
<220> FEATURE:
<223> OTHER INFORMATION: Primer

<400> SEQUENCE: 6
gccttgccag cccgctcagt cagagtttga tcctggctca g    41

<210> SEQ ID NO 7
<211> LENGTH: 52
<212> TYPE: DNA
<213> ORGANISM: Artificial Sequence
<220> FEATURE:
<223> OTHER INFORMATION: Primer

```
<220> FEATURE:
<221> NAME/KEY: misc_feature
<222> LOCATION: (20)..(31)
<223> OTHER INFORMATION: n is a, c, g, or t

<400> SEQUENCE: 7
gcctccctcg cgccatcagn nnnnnnnnnn ncatgctgcc tcccgtagga gt        52

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
gtgccagcmg ccgcggtaa                                              19

<210> SEQ ID NO 9
<211> LENGTH: 17
<212> TYPE: DNA
<213> ORGANISM: Artificial Sequence
<220> FEATURE:
<223> OTHER INFORMATION: Primer

<400> SEQUENCE: 9
gacgggcggt gwgtrca                                                17

<210> SEQ ID NO 10
<211> LENGTH: 12
<212> TYPE: DNA
<213> ORGANISM: Artificial Sequence
<220> FEATURE:
<223> OTHER INFORMATION: primer or barcode

<400> SEQUENCE: 10
acgtgccgta ga                                                     12

<210> SEQ ID NO 11
<211> LENGTH: 21
<212> TYPE: DNA
<213> ORGANISM: Artificial Sequence
<220> FEATURE:
<223> OTHER INFORMATION: primer or barcode

<400> SEQUENCE: 11
catgctgcct cccgtaggag t                                           21

<210> SEQ ID NO 12
<211> LENGTH: 12
<212> TYPE: DNA
<213> ORGANISM: Artificial Sequence
<220> FEATURE:
<223> OTHER INFORMATION: primer or barcode

<400> SEQUENCE: 12
acgctatctg ga                                                     12

<210> SEQ ID NO 13
<211> LENGTH: 21
<212> TYPE: DNA
<213> ORGANISM: Artificial Sequence
<220> FEATURE:
<223> OTHER INFORMATION: primer or barcode

<400> SEQUENCE: 13
```
catgctgcct cccgtaggag t                                                  21

<210> SEQ ID NO 14
<211> LENGTH: 12
<212> TYPE: DNA
<213> ORGANISM: Artificial Sequence
<220> FEATURE:
<223> OTHER INFORMATION: primer or barcode

<400> SEQUENCE: 14
actcgattcg at                                                            12

<210> SEQ ID NO 15
<211> LENGTH: 21
<212> TYPE: DNA
<213> ORGANISM: Artificial Sequence
<220> FEATURE:
<223> OTHER INFORMATION: primer or barcode

<400> SEQUENCE: 15
catgctgcct cccgtaggag t                                                  21

<210> SEQ ID NO 16
<211> LENGTH: 12
<212> TYPE: DNA
<213> ORGANISM: Artificial Sequence
<220> FEATURE:
<223> OTHER INFORMATION: primer or barcode

<400> SEQUENCE: 16
acacgagcca ca                                                            12

<210> SEQ ID NO 17
<211> LENGTH: 21
<212> TYPE: DNA
<213> ORGANISM: Artificial Sequence
<220> FEATURE:
<223> OTHER INFORMATION: primer or barcode

<400> SEQUENCE: 17
catgctgcct cccgtaggag t                                                  21

<210> SEQ ID NO 18
<211> LENGTH: 12
<212> TYPE: DNA
<213> ORGANISM: Artificial Sequence
<220> FEATURE:
<223> OTHER INFORMATION: primer or barcode

<400> SEQUENCE: 18
agactgcgta ct                                                            12

<210> SEQ ID NO 19
<211> LENGTH: 21
<212> TYPE: DNA
<213> ORGANISM: Artificial Sequence
<220> FEATURE:
<223> OTHER INFORMATION: primer or barcode

<400> SEQUENCE: 19
catgctgcct cccgtaggag t                                                  21

<210> SEQ ID NO 20
<211> LENGTH: 12
<212> TYPE: DNA
<213> ORGANISM: Artificial Sequence

```
<220> FEATURE:
<223> OTHER INFORMATION: primer or barcode

<400> SEQUENCE: 20
acatgatcgt tc                                                          12

<210> SEQ ID NO 21
<211> LENGTH: 21
<212> TYPE: DNA
<213> ORGANISM: Artificial Sequence
<220> FEATURE:
<223> OTHER INFORMATION: primer or barcode

<400> SEQUENCE: 21
catgctgcct cccgtaggag t                                                21

<210> SEQ ID NO 22
<211> LENGTH: 12
<212> TYPE: DNA
<213> ORGANISM: Artificial Sequence
<220> FEATURE:
<223> OTHER INFORMATION: primer or barcode

<400> SEQUENCE: 22
accgcagagt ca                                                          12

<210> SEQ ID NO 23
<211> LENGTH: 21
<212> TYPE: DNA
<213> ORGANISM: Artificial Sequence
<220> FEATURE:
<223> OTHER INFORMATION: primer or barcode

<400> SEQUENCE: 23
catgctgcct cccgtaggag t                                                21

<210> SEQ ID NO 24
<211> LENGTH: 12
<212> TYPE: DNA
<213> ORGANISM: Artificial Sequence
<220> FEATURE:
<223> OTHER INFORMATION: primer or barcode

<400> SEQUENCE: 24
acttgtagca gc                                                          12

<210> SEQ ID NO 25
<211> LENGTH: 21
<212> TYPE: DNA
<213> ORGANISM: Artificial Sequence
<220> FEATURE:
<223> OTHER INFORMATION: primer or barcode

<400> SEQUENCE: 25
catgctgcct cccgtaggag t                                                21

<210> SEQ ID NO 26
<211> LENGTH: 12
<212> TYPE: DNA
<213> ORGANISM: Artificial Sequence
<220> FEATURE:
<223> OTHER INFORMATION: primer or barcode

<400> SEQUENCE: 26
agcgctgatg tg                                                          12
```

```
<210> SEQ ID NO 27
<211> LENGTH: 21
<212> TYPE: DNA
<213> ORGANISM: Artificial Sequence
<220> FEATURE:
<223> OTHER INFORMATION: primer or barcode

<400> SEQUENCE: 27
catgctgcct cccgtaggag t                                              21

<210> SEQ ID NO 28
<211> LENGTH: 12
<212> TYPE: DNA
<213> ORGANISM: Artificial Sequence
<220> FEATURE:
<223> OTHER INFORMATION: primer or barcode

<400> SEQUENCE: 28
acattcagcg ca                                                        12

<210> SEQ ID NO 29
<211> LENGTH: 21
<212> TYPE: DNA
<213> ORGANISM: Artificial Sequence
<220> FEATURE:
<223> OTHER INFORMATION: primer or barcode

<400> SEQUENCE: 29
catgctgcct cccgtaggag t                                              21

<210> SEQ ID NO 30
<211> LENGTH: 12
<212> TYPE: DNA
<213> ORGANISM: Artificial Sequence
<220> FEATURE:
<223> OTHER INFORMATION: primer or barcode

<400> SEQUENCE: 30
agatcggctc ga                                                        12

<210> SEQ ID NO 31
<211> LENGTH: 21
<212> TYPE: DNA
<213> ORGANISM: Artificial Sequence
<220> FEATURE:
<223> OTHER INFORMATION: primer or barcode

<400> SEQUENCE: 31
catgctgcct cccgtaggag t                                              21

<210> SEQ ID NO 32
<211> LENGTH: 12
<212> TYPE: DNA
<213> ORGANISM: Artificial Sequence
<220> FEATURE:
<223> OTHER INFORMATION: primer or barcode

<400> SEQUENCE: 32
acatcactta gc                                                        12

<210> SEQ ID NO 33
<211> LENGTH: 21
<212> TYPE: DNA
<213> ORGANISM: Artificial Sequence
<220> FEATURE:
<223> OTHER INFORMATION: primer or barcode
```

```
<400> SEQUENCE: 33
catgctgcct cccgtaggag t                                              21

<210> SEQ ID NO 34
<211> LENGTH: 12
<212> TYPE: DNA
<213> ORGANISM: Artificial Sequence
<220> FEATURE:
<223> OTHER INFORMATION: primer or barcode

<400> SEQUENCE: 34
actcacggta tg                                                        12

<210> SEQ ID NO 35
<211> LENGTH: 21
<212> TYPE: DNA
<213> ORGANISM: Artificial Sequence
<220> FEATURE:
<223> OTHER INFORMATION: primer or barcode

<400> SEQUENCE: 35
catgctgcct cccgtaggag t                                              21

<210> SEQ ID NO 36
<211> LENGTH: 12
<212> TYPE: DNA
<213> ORGANISM: Artificial Sequence
<220> FEATURE:
<223> OTHER INFORMATION: primer or barcode

<400> SEQUENCE: 36
agctatccac ga                                                        12

<210> SEQ ID NO 37
<211> LENGTH: 21
<212> TYPE: DNA
<213> ORGANISM: Artificial Sequence
<220> FEATURE:
<223> OTHER INFORMATION: primer or barcode

<400> SEQUENCE: 37
catgctgcct cccgtaggag t                                              21

<210> SEQ ID NO 38
<211> LENGTH: 12
<212> TYPE: DNA
<213> ORGANISM: Artificial Sequence
<220> FEATURE:
<223> OTHER INFORMATION: primer or barcode

<400> SEQUENCE: 38
accacataca tc                                                        12

<210> SEQ ID NO 39
<211> LENGTH: 21
<212> TYPE: DNA
<213> ORGANISM: Artificial Sequence
<220> FEATURE:
<223> OTHER INFORMATION: primer or barcode

<400> SEQUENCE: 39
catgctgcct cccgtaggag t                                              21

<210> SEQ ID NO 40
```

-continued

```
<211> LENGTH: 12
<212> TYPE: DNA
<213> ORGANISM: Artificial Sequence
<220> FEATURE:
<223> OTHER INFORMATION: primer or barcode

<400> SEQUENCE: 40
aggtgtgatc gc                                                              12

<210> SEQ ID NO 41
<211> LENGTH: 21
<212> TYPE: DNA
<213> ORGANISM: Artificial Sequence
<220> FEATURE:
<223> OTHER INFORMATION: primer or barcode

<400> SEQUENCE: 41
catgctgcct cccgtaggag t                                                    21

<210> SEQ ID NO 42
<211> LENGTH: 12
<212> TYPE: DNA
<213> ORGANISM: Artificial Sequence
<220> FEATURE:
<223> OTHER INFORMATION: primer or barcode

<400> SEQUENCE: 42
acgtctgtag ca                                                              12

<210> SEQ ID NO 43
<211> LENGTH: 21
<212> TYPE: DNA
<213> ORGANISM: Artificial Sequence
<220> FEATURE:
<223> OTHER INFORMATION: primer or barcode

<400> SEQUENCE: 43
catgctgcct cccgtaggag t                                                    21

<210> SEQ ID NO 44
<211> LENGTH: 12
<212> TYPE: DNA
<213> ORGANISM: Artificial Sequence
<220> FEATURE:
<223> OTHER INFORMATION: primer or barcode

<400> SEQUENCE: 44
agagtcctga gc                                                              12

<210> SEQ ID NO 45
<211> LENGTH: 21
<212> TYPE: DNA
<213> ORGANISM: Artificial Sequence
<220> FEATURE:
<223> OTHER INFORMATION: primer or barcode

<400> SEQUENCE: 45
catgctgcct cccgtaggag t                                                    21

<210> SEQ ID NO 46
<211> LENGTH: 12
<212> TYPE: DNA
<213> ORGANISM: Artificial Sequence
<220> FEATURE:
<223> OTHER INFORMATION: primer or barcode

<400> SEQUENCE: 46
```
aagagatgtc ga                                                             12

<210> SEQ ID NO 47
<211> LENGTH: 21
<212> TYPE: DNA
<213> ORGANISM: Artificial Sequence
<220> FEATURE:
<223> OTHER INFORMATION: primer or barcode

<400> SEQUENCE: 47
catgctgcct cccgtaggag t                                                   21

<210> SEQ ID NO 48
<211> LENGTH: 12
<212> TYPE: DNA
<213> ORGANISM: Artificial Sequence
<220> FEATURE:
<223> OTHER INFORMATION: primer or barcode

<400> SEQUENCE: 48
acactagatc cg                                                             12

<210> SEQ ID NO 49
<211> LENGTH: 21
<212> TYPE: DNA
<213> ORGANISM: Artificial Sequence
<220> FEATURE:
<223> OTHER INFORMATION: primer or barcode

<400> SEQUENCE: 49
catgctgcct cccgtaggag t                                                   21

<210> SEQ ID NO 50
<211> LENGTH: 12
<212> TYPE: DNA
<213> ORGANISM: Artificial Sequence
<220> FEATURE:
<223> OTHER INFORMATION: primer or barcode

<400> SEQUENCE: 50
aggacgcact gt                                                             12

<210> SEQ ID NO 51
<211> LENGTH: 21
<212> TYPE: DNA
<213> ORGANISM: Artificial Sequence
<220> FEATURE:
<223> OTHER INFORMATION: primer or barcode

<400> SEQUENCE: 51
catgctgcct cccgtaggag t                                                   21

<210> SEQ ID NO 52
<211> LENGTH: 12
<212> TYPE: DNA
<213> ORGANISM: Artificial Sequence
<220> FEATURE:
<223> OTHER INFORMATION: primer or barcode

<400> SEQUENCE: 52
agagagcaag tg                                                             12

<210> SEQ ID NO 53
<211> LENGTH: 21
<212> TYPE: DNA

```
<213> ORGANISM: Artificial Sequence
<220> FEATURE:
<223> OTHER INFORMATION: primer or barcode

<400> SEQUENCE: 53
catgctgcct cccgtaggag t                                              21

<210> SEQ ID NO 54
<211> LENGTH: 12
<212> TYPE: DNA
<213> ORGANISM: Artificial Sequence
<220> FEATURE:
<223> OTHER INFORMATION: primer or barcode

<400> SEQUENCE: 54
acgcgatact gg                                                        12

<210> SEQ ID NO 55
<211> LENGTH: 21
<212> TYPE: DNA
<213> ORGANISM: Artificial Sequence
<220> FEATURE:
<223> OTHER INFORMATION: primer or barcode

<400> SEQUENCE: 55
catgctgcct cccgtaggag t                                              21

<210> SEQ ID NO 56
<211> LENGTH: 12
<212> TYPE: DNA
<213> ORGANISM: Artificial Sequence
<220> FEATURE:
<223> OTHER INFORMATION: primer or barcode

<400> SEQUENCE: 56
agagcaagag ca                                                        12

<210> SEQ ID NO 57
<211> LENGTH: 21
<212> TYPE: DNA
<213> ORGANISM: Artificial Sequence
<220> FEATURE:
<223> OTHER INFORMATION: primer or barcode

<400> SEQUENCE: 57
catgctgcct cccgtaggag t                                              21

<210> SEQ ID NO 58
<211> LENGTH: 12
<212> TYPE: DNA
<213> ORGANISM: Artificial Sequence
<220> FEATURE:
<223> OTHER INFORMATION: primer or barcode

<400> SEQUENCE: 58
aatcagtctc gt                                                        12

<210> SEQ ID NO 59
<211> LENGTH: 21
<212> TYPE: DNA
<213> ORGANISM: Artificial Sequence
<220> FEATURE:
<223> OTHER INFORMATION: primer or barcode

<400> SEQUENCE: 59
catgctgcct cccgtaggag t                                              21
```

<210> SEQ ID NO 60
<211> LENGTH: 12
<212> TYPE: DNA
<213> ORGANISM: Artificial Sequence
<220> FEATURE:
<223> OTHER INFORMATION: primer or barcode

<400> SEQUENCE: 60
agcttgacag ct                                                              12

<210> SEQ ID NO 61
<211> LENGTH: 21
<212> TYPE: DNA
<213> ORGANISM: Artificial Sequence
<220> FEATURE:
<223> OTHER INFORMATION: primer or barcode

<400> SEQUENCE: 61
catgctgcct cccgtaggag t                                                    21

<210> SEQ ID NO 62
<211> LENGTH: 12
<212> TYPE: DNA
<213> ORGANISM: Artificial Sequence
<220> FEATURE:
<223> OTHER INFORMATION: primer or barcode

<400> SEQUENCE: 62
actacagcct at                                                              12

<210> SEQ ID NO 63
<211> LENGTH: 21
<212> TYPE: DNA
<213> ORGANISM: Artificial Sequence
<220> FEATURE:
<223> OTHER INFORMATION: primer or barcode

<400> SEQUENCE: 63
catgctgcct cccgtaggag t                                                    21

<210> SEQ ID NO 64
<211> LENGTH: 12
<212> TYPE: DNA
<213> ORGANISM: Artificial Sequence
<220> FEATURE:
<223> OTHER INFORMATION: primer or barcode

<400> SEQUENCE: 64
acagtgcttc at                                                              12

<210> SEQ ID NO 65
<211> LENGTH: 21
<212> TYPE: DNA
<213> ORGANISM: Artificial Sequence
<220> FEATURE:
<223> OTHER INFORMATION: primer or barcode

<400> SEQUENCE: 65
catgctgcct cccgtaggag t                                                    21

MICROBIOME BASED SYSTEMS, APPARATUS AND METHODS FOR MONITORING AND CONTROLLING INDUSTRIAL PROCESSES AND SYSTEMS

This application: (i) claims, under 35 U.S.C. § 119(e)(1), the benefit of the filing date of Dec. 31, 2013 of U.S. provisional application Ser. No. 61/922,734; and (ii) claims, under 35 U.S.C. § 119(e)(1), the benefit of the filing date of Feb. 26, 2014 of U.S. provisional application Ser. No. 61/944,961, the entire disclosures of each of which are incorporated herein by reference.

This invention was made with Government support under SBIR award number 1416179 by the National Science Foundation. The Government has certain rights in this invention.

REFERENCE TO AN ELECTRONIC SEQUENCE LISTING

The content of the electronic sequence listing (B1a_ST25.txt; Size 13 KB; and Date of Creation Jun. 20, 2015) is herein incorporated by reference in its entirety.

BACKGROUND OF THE INVENTION

Field of the Invention

The present inventions relate to novel and unique methods, systems and processes for monitoring, analyzing and controlling industrial activities. Industrial activities entail a wide range of endeavors that are directed toward agriculture, manufacturing, chemical processing, energy exploration and production, energy generation, mining, and transpiration, to name a few. Typically, industrial activities are thought of as being large scale operations, such as an open pit gold mine spanning hundreds of thousands of acres, a cosmetics line having hundreds of products and formulations, an oil field having hundreds of producing wells, a natural gas pipeline network having thousands of miles of pipeline, and a dairy farm having over a thousand cows. Yet, they may also include smaller scale, and small-scale operations, such as a small custom cheese maker in Wisconsin, an organic vineyard in California, and a marijuana grower in Colorado.

There has been a continuous need for a better understanding of industrial activities, and to integrate and use this understanding to improve and enhance these operations. Thus, great efforts have been made in areas such as factory automation and control, mine engineering and management, and oil field reservoir management, to name a few. Generally, these efforts have focused on traditional sensing, analysis and control methodologies. These traditional methodologies would include such things as temperature and pressure sensing, optical sensors, I/O (i.e., input/output modules), optical data transmission (e.g., fiber optics), communication systems (e.g., Ethernet networks), programmable logic controllers (i.e., PLCs), computer based algorithms to analyze data, such as seismic data, GPS location information, mechanical testing, such as tensile strength, and chemical analysis, such as pH. Thus, and in general, for their sources of information, the industrial arts have focused on what could be termed traditional physical phenomena that are directly observable or measurable, e.g., how hot is the reaction vessel, how much wheat per acre was harvested.

The art of industrial monitoring, automation and control, however, has largely ignored the microbial and genetic information that is present in, or associated with, an industrial operation. While efforts have been made to evaluate a particular microbial present in an industrial operation, these efforts have largely focused on identification, e.g., through DNA analysis, for the purposes of eliminating undesirable microbes and increasing beneficial ones. Further, analysis and work has taken place to genetically engineer microbes to meet, or fulfill, a particular function in an industrial operation. However, it is believed that prior to the present inventions, the use of microbial and genetic information, has never been used, and was not able to be used, for the purposes monitoring, analyzing and controlling industrial activities, such as, industrial operation, automation, control, planning and prediction.

Thus, and in general, the present inventions provide apparatus, systems and methods for determining and characterizing the microbiome of an industrial operation or settings, obtaining such microbiome information, converting such information into a form that is useful in an industrial operation or setting, using such information in the industrial activity, and combinations and variations of these. In view of the ubiquitous nature of genetic material and microorganisms, the present inventions provide the ability to control, enhance, monitor, and predict performance of industrial activities in a wide range of fields and applications.

The terms microbiome, microbiome information, microbiome data, and similar such terms are used herein in the broadest possible sense, unless expressly stated otherwise, and would include: a census of currently present microorganisms, both living and nonliving, which may have been present months, years, millennia or longer ("the microbiota"); a census of components of the microbiome other than bacteria and archaea, e.g., viruses and microbial eukaryotes; population studies and characterizations of microorganisms, genetic material, and biologic material; a census of any detectable biological material; and information that is derived or ascertained from genetic material, biomolecular makeup, fragments of genetic material, DNA, RNA, protein, carbohydrate, metabolite profile, fragment of biological materials and combinations and variations of these.

As used herein, the terms historic microbiome information and historic microbiome data are to be given their broadest possible meaning, unless specified otherwise, and includes publicly available databases, e.g., the Earth Microbiome Project, the Human Microbiome Project, American Gut, GreenGenes, the Ribosomal Database Project, the International Nucleotide Sequence Database Collaboration (INSDC), American Gut, etc., regarding the microbiome. It would also include databases that are based upon real-time microbiome data and derived microbiome data. These databases may be cloud-based, locally-based, or hosted on remote systems other than cloud-based systems.

As used herein, the terms real-time microbiome information and real-time microbiome data are to be given their broadest possible meaning, unless specified otherwise, and includes microbiome information that is collected or obtained at a particular industrial setting during an industrial activity, which would include for example sampling and determining the microbiome present in a pipeline flow, in returns from drilling a borehole, in hydraulic fracturing fluid, agricultural runoff or soil samples taken during a planting or harvesting.

As used herein, the terms derived microbiome information and derived microbiome data are to be given their broadest possible meaning, unless specified otherwise, and includes any real-time, historic, and combinations of these, microbiome information that has been computationally linked or used to create a relationship such as for example evaluating the microbiome of hydraulic fracturing fluid before, during, and after hydraulic fracturing stages, evaluating the microbiome between planting and harvesting, and evaluating the historic microbiome of deep core samples with the microbiome of hydrocarbon product delivered from the well. Thus, derived microbiome information provides information about the industrial process setting or activity that may not be readily ascertained from non-derived information.

As used herein, the terms predictive microbiome information and predictive microbiome data are to be given their broadest possible meaning, unless specified otherwise, and includes information that is based upon combinations and computational links or processing of historic, predictive, real-time, and derived microbiome information, data, and combinations, variations and derivatives of these, which information predicts, forecasts, directs, or anticipates a future occurrence, event, state, or condition in the industrial setting, or allows interpretation of a current or past occurrence. Thus, by way of example, predictive microbiome information would include: a determination and comparison of real-time microbiome information and the derived microbiome information of an exploratory process to identify a hydrocarbon source; a comparison of real-time microbiome information collected during the advancement of a borehole to predict a perforation or hydraulic fracturing pattern; a determination and comparison of derived microbiome information and historic microbiome information of a chemical processing plant to identify an enhanced efficiency in the process; and, a comparison and analysis of historic microbiome data from, for example, core samples and derived microbiome information from well cutting returns to characterize a formation.

Real-time, derived, and predicted data may be collected and stored, and thus, become historic data for an ongoing or future process, setting, or application.

SUMMARY

Accordingly, there has been a long-standing and unfulfilled need for better abilities to monitor, analyze, plan and control industrial activities and endeavors, including activities and endeavors, among other things, that are directed toward agriculture, manufacturing, chemical processing, energy exploration and production, food production, energy generation, mining, and transpiration. Traditional monitoring and control applications have significant failings and have not met these continuing needs. Accordingly, the present inventions, among other things, solve these needs by providing the articles of manufacture, devices and processes taught, disclosed and claimed herein.

Thus, there is provided an industrial operation including: analyzing a material from a location associated with an industrial operation; obtaining microbiome information, the microbiome information selected from the group consisting of historic microbiome information, real time microbiome information, derived microbiome information and predictive microbiome information; and, performing an evaluation on the microbiome information, the evaluation including: a relationship based processing including a related genetic material component and an industrial setting component; and, a bioinformatics stage; whereby the evaluation provides information to direct the industrial operation.

There is further provide the present systems, operations and methods having one or more of the following features: wherein, the historic microbiome information is selected from the group consisting of the Earth Microbiome Project, the Human Microbiome Project, American Gut, Green-Genes, the Ribosomal Database Project, the International Nucleotide Sequence Database Collaboration (INSDC), and American Gut; wherein, the real time microbiome information is selected from material selected from the group consisting of pipeline flow, drilling returns, fracturing returns, hydraulic fracturing fluid, crude oil, hydrocarbon streams, agricultural runoff, ground water, soil samples, soils samples taken during a planting, soil sample taken during a harvesting, food samples and subterranean formation; wherein, the industrial setting component is selected from the group consisting of GPS data; location data, system component identification, subsystem component identification, pump station true vertical depth of a well, pH, measured depth of a well, processing stage, geological parameter, formation permeability, viscosity, porosity, pressure, flow, and temperature; wherein, the bioinformatics stage has submitting the microbiome information to QIIME processing; wherein, the bioinformatics stage has: compiling metadata mapping; barcode decoding; OTU picking; constructing phylogentic trees; constructing a BIOM table; and UniFac and PCoA; wherein, the bioinformatics stage has: compiling metadata mapping; barcode decoding; OTU picking; constructing phylogentic trees; constructing a BIOM table; and UniFac and PCoA; wherein, the bioinformatics stage has: compiling metadata mapping; barcode decoding; OTU picking; constructing phylogentic trees; constructing a BIOM table; and UniFac and PCoA; wherein, the bioinformatics stage has: compiling metadata mapping; OTU picking; constructing phylogentic trees; constructing a BIOM table; and UniFac and PCoA; wherein, the bioinformatics stage has: compiling metadata mapping; OTU picking; constructing a BIOM table; and UniFac and PCoA; and wherein, the bioinformatics stage has: constructing a BIOM table; and UniFac and PCoA.

Still moreover there is provided a method of controlling an industrial operation including: analyzing a material from a location associated with an industrial operation to provide a first microbiome information; associating the first microbiome information with a condition of the operation; obtaining a second microbiome information; associating the second microbiome information with the first microbiome information; and, evaluating the first microbiome information, the associated condition, and the second microbiome information, the evaluation including QIIME processing, the QIIME processing including constructing a phylogentic tree, constructing a BIOM table, UniFac, and PCoA; whereby the evaluation identifies a characteristic of the operation; and, directing the industrial operation based in part on the identified characteristic of operation; whereby the industrial operation is based upon the evaluation of microbiome information.

Yet further there is provided a method of controlling an industrial operation including: analyzing a material from a location associated with an industrial operation to provide a first microbiome information; associating the first microbiome information with a condition of the operation; obtaining a second microbiome information; associating the second microbiome information with the first microbiome information; and, evaluating the first microbiome information, the associated condition, and the second microbiome information, the evaluation including constructing a phylogentic tree and UniFac; whereby the evaluation identifies a characteristic of the operation; and, directing the industrial operation based in part on the identified characteristic of operation;

whereby the industrial operation is based upon the evaluation of microbiome information.

Furthermore there is provided a method of controlling an industrial operation including: analyzing a material from a location associated with an industrial operation to provide a first microbiome information; associating the first microbiome information with a condition of the operation; obtaining a second microbiome information; associating the second microbiome information with the first microbiome information; and, evaluating the first microbiome information, the associated condition, and the second microbiome information, the evaluation including compiling a sample metadata mapping file containing mapped information, submitting the mapped information to QIIME processing; whereby the evaluation identifies a characteristic of the operation; and, directing the industrial operation based in part on the identified characteristic of operation; whereby the industrial operation is based upon the evaluation of microbiome information.

Yet still additionally, there is provided an industrial operation including: analyzing a material from a location associated with an industrial operation; obtaining microbiome information; and, performing an evaluation on the microbiome information, whereby the evaluation provides information to direct the industrial operation.

There is further provide the present systems, operations and methods having one or more of the following features: wherein, the microbiome information has historic microbiome information; wherein, the microbiome information has real time microbiome information; wherein, the microbiome information has derived microbiome information; wherein, the microbiome information has predictive microbiome information; wherein the analysis has selection and sequencing of the material; wherein the analysis has extracting genetic material from the material; wherein the analysis has preparation of libraries; wherein the analysis has extracting material including genetic material selected from the group consisting of a SSU rRNA gene 16S, SSU rRNA gene 18S, LSU rRNA gene 23S, LSU rRNA 28S, ITS in the rRNA operon, and ITS in the rRNA cpn60; wherein the analysis has providing a phylogenetic tree; wherein the analysis has a correction step; wherein the analysis has an extraction procedure selected from the group consisting of beating, sonicating, freezing and thawing, and chemical disruption; wherein the analysis has amplification of at least a portion of the material; wherein the analysis has providing a genetic barcode to a sample of the material; wherein the microbiome information defines a phylogenetic tree; wherein the microbiome information has a OUT; wherein the microbiome information defines an OUT; wherein the microbiome information defines a biogeographical pattern; wherein the microbiome information has information obtained from variable regions of the 16S rRNA; wherein the variable regions are selected from the group consisting of V2, V4, and V6; wherein the evaluation has forming an n-dimensional plot, where n is selected from the group of integers consisting of 3, 4, 5, 6, 8, 9, 10, 11, 12, 13, and 14; wherein the evaluation has measuring a change in gene sequences; wherein the evaluation has measuring a change in gene sequences and using the measured change as a molecular clock in the evaluation to determine the related nature of material; and wherein the material is selected from the group of consisting of fracturing fluid, drilling mud, drilling fluid returns, a material from an agriculture operation, a material from a chemical operation, a material from a cosmetic operation and a material from a mining operation.

There is further provide the present systems, operations and methods having one or more of the following features: wherein at least a portion of the information resulting from the evaluation is displayed in a two dimensional plot; wherein at least a portion of the information resulting from the evaluation is displayed in a three dimensional plot; wherein at least a portion of the information resulting from the evaluation is displayed in a plot including colors associated with microbiome information; wherein at least a portion of the information resulting from the evaluation is displayed in a plot including colors associated with a type of information selected from the group consisting of microbiome information and non-genetic information; each type of information including a different color; wherein at least a portion of the information resulting from the evaluation is displayed in a plot including colors associated with a type of information selected from the group consisting of microbiome information and non-genetic information; each type of information including a different color; and the non-genetic information selected from the group consisting of temperature, gps, pressure, depth, borehole true vertical depth, casing collar location, and viscosity; wherein at least a portion of the information resulting from the evaluation is transmitted to a memory storage device; wherein at least a portion of the information resulting from the evaluation is communicated to a controller; wherein at least a portion of the information resulting from the evaluation is displayed in a two dimensional plot; and, wherein at least a portion of the information resulting from the evaluation is displayed in a three dimensional plot.

Yet still there is provided a method of controlling an industrial operation including: analyzing a material from a location associated with an industrial operation to provide a first microbiome information; associating the first microbiome information with a condition of the operation; obtaining a second microbiome information; associating the second microbiome information with the first microbiome information; and, evaluating the first microbiome information, the associated condition, and the second microbiome information, whereby the evaluation identifies a characteristic of the operation, and using the identified characteristic to direct the industrial operation; whereby the industrial operation is based upon the evaluation of microbiome information.

There is further provide the present systems, operations and methods having one or more of the following features: wherein the industrial operation is selected from the group consisting of hydraulic fracturing, drilling a borehole, an agriculture operation, a chemical operation, a cosmetic operation and a mining operation.

There is further provide the present systems, operations and methods having one or more of the following features: wherein the second microbiome information is historic information and the first microbiome information is real time information; wherein the second microbiome information is derived microbiome information and the first microbiome information is real time information; wherein the second microbiome information is historic information and the first microbiome information is derived microbiome information; wherein the second microbiome information is historic information and the first microbiome information is derived microbiome information; wherein, the first microbiome information is stored as historic microbiome information; wherein, the first microbiome information has real time microbiome information; wherein, the second microbiome information has derived microbiome information;

and including obtaining a third microbiome information and wherein, the third microbiome information has predictive microbiome information.

Moreover there is provided a method of controlling an industrial process including: analyzing a material from an industrial process to provide a first microbiome information; obtaining a second microbiome information; associating the first microbiome information, the second microbiome information or both information with a condition of the processes; and, storing at least on of the first, or the second microbiome information; evaluating the first microbiome information, the associated condition, and the second microbiome information, whereby the evaluation provides predictive information.

There is further provide the present systems, operations and methods having one or more of the following features: wherein at least a portion of the information resulting from the evaluation is displayed in a plot having colors associated with a type of information selected from the group consisting of microbiome information and non-genetic information; each type of information having a different color; and the non-genetic information selected from the group consisting of temperature, gps, pressure, depth, borehole true vertical depth, casing collar location, and viscosity.

BRIEF DESCRIPTION OF THE DRAWINGS

FIG. 6 is graph and illustration of an embodiment of a matrix in accordance with the present inventions.

DESCRIPTION OF THE PREFERRED EMBODIMENTS

Figure 1:
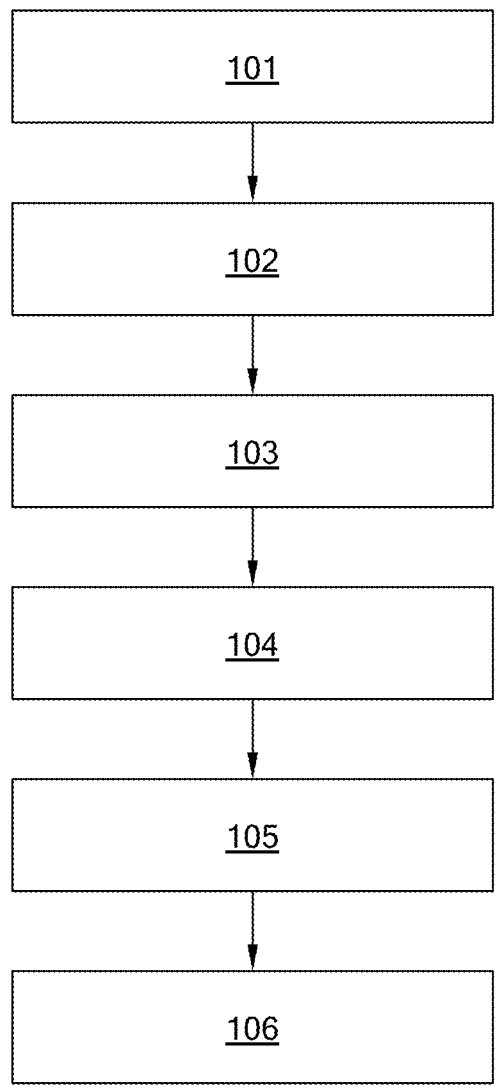
FIG. 1 is a flow chart of an embodiment of a process in accordance with the present inventions.

In general, the present inventions relate to methods, systems and processes for the utilization of microbial and DNA-related information as well as the determination and relative characterization of microbes and genetic material for use in industrial settings. These industrial settings include the exploration, determination, and recovery of natural resources, minerals, and energy sources; the monitoring and analysis of processes, activities, and materials transmission such as slurries, food products, and hydrocarbon-containing sources; agricultural processes and systems; the analysis and monitoring of equipment, life cycle, and efficacy; as well as the optimization of industrial and agricultural processes; and combinations and variations of these and other activities. Further, specific fields for these industrial settings for the present invention would include, for example, energy exploration and production including all phases of well planning, construction, completion, production, intervention and workover, and decommissioning including perforation and hydraulic fracturing and reservoir management; pipelines, including monitoring, sampling, maintenance, and diagnostics; mineral, gems, and precious and rare substance exploration and production; chemical and biochemical processing including refining, food processing, agriculture including plant breeding, crop insurance, commodity pricing, management of inputs such as fertilizer and water; waste management; environmental monitoring, tracking, and remediation; water purification and quality control; security, forensics, product and source identification, identification and tracking of persons, and counterfeit identification; consumer products including health and beauty and personal services; and other industrial settings where microbes and/or genetic material may be present. The present invention finds utility in the forgoing applications and settings as well as in many other applications and settings in view of the ubiquitous nature of genetic material and microorganisms.

Thus, microbes and genetic material exist in industrial settings environment from historic, e.g., archaeological sources, deep within the earth, highly automated and mechanical settings, the air, and essentially within any location that has not been sterilized (and even in such settings genetic material that may be useful for analysis may be present). These microbes and their genetic material provide a significant yet largely untapped source of information for monitoring, refining, improving, and conducting industrial activity.

In general, the present inventions further relate to systems and methods for determining and characterizing the microbiomes of such industrial settings, and in particular determining through relationship-based processing, which include custom and unique analytics tools and algorithms, data management, cleansing, filtering, and quality control, which in turn provide information about the industrial setting. Such characterized information, for example, can have, and be used for, predictive, historical, analytic, development, control and monitoring purposes.

The relationship-based processing utilizing microbiome information may include historic microbiome information, real-time-based microbiome information, derived microbiome information, and predictive microbiome information, and combinations and variations of these. Further, this relationship-based processing utilizes these various types of microbiome information in combination with other data and information such as GPS data; traditional industrial automation data, e.g., flow rate, temperature, pressure; geologic data; and climate data.

This information, data, processing algorithms support software, such as human machine interface (HMI) programs and graphic programs, and databases, may be cloud-based, locally-based, hosted on remote systems other than cloud-based systems, and combinations and variations of these.

Thus, real-time, derived, and predicted data may be collected and stored and thus become historic data for an ongoing process, setting, or application. In this manner, the collection, use, and computational links can create a real-time situation in which machine learning can be applied to further enhance and refine the industrial activities or processes. Further, real-time, derived, predictive, and historic data can be, and preferably is, associated with other data and information. Thus, the microbiome information can be associated with GPS data; location data, e.g., particular components and subsystems in an industrial process such as for example a particular pump station in a pipeline, a particular measured or true vertical depth of a well; processing stage or step such as filtration of fermentation broth, a unit operation during a chemical or biochemical process including petrochemical refining, pharmaceutical production, stage of a hydraulic fracturing operation; geological parameters including formation permeability and porosity; the identifying features of a subject for cosmetics; factory processing conditions such as pressure, flow, temperature, and time; soil moisture, nutrient, and rainfall conditions in agricultural processes.

Thus, real-time, derived, historic, and predictive microbiome information may be further combined or processed with these other sources of information and data regarding the industrial setting or process to provide combined, derived, and predictive information. In this manner, the microbiome information is used in combination with other data and information to provide for unique and novel ways to conduct industrial operations, to develop or plan industrial operations, to refine and enhance existing industrial operations and combinations of these and other activities.

Preferably, these various types of information and data are combined where one or more may become metadata for the other. In this manner, information may be linked in a manner that provides for rapid, efficient, and accurate processing to provide useful information relating to the industrial setting. Thus for example, in agricultural setting the soil moisture content, the GPS location down to the square yard of a large farm may be linked as metadata to the real-time microbiome information during planting and compared with similarly linked meta-data obtained during harvesting along with crop yield for that acre to refine and enhance the agricultural processing of the field in which the acre is located. Thus for an example in an exploration and production hydrocarbon setting, GPS data, geologic data, and measured total depth data may be used as metadata associated with real-time microbiome data obtained from well cutting returns. This metadata linked real-time microbiome data is then analyzed during the advancement of the borehole to determine the characterization of the formation and a perforation and hydraulic fracturing plan to improve production. Thus for an example in an exploration and production hydrocarbon setting, microbiome data obtained from well cutting returns may be used as metadata and associated with real-time GPS data, geologic data, and measured total depth data. This metadata-linked historic microbiome data is then analyzed during the advancement of the borehole, potentially in conjunction with real-time data, to determine the characterization of the formation and a perforation and hydraulic fracturing plan to improve production.

Thus it is understood that microbiome information may be used as metadata or may be the underlying information with which the metadata is associated. Further, in creating larger databases it may be advantageous to have the ability to disassociate some metadata from the underlying information. In this manner, historic microbiome information may be collected which has far greater utilization in which companies or individuals are more willing to participate or contribute yet which provides the ability to be utilized in further and improved derived and predictive activities.

In general, historic microbiome data may be obtained from known databases or it may be obtained from conducting population studies or censuses of the microbiome for the particular industrial setting. Thus samples of biological materials are collected and characterized. This characterized information is then processed and stored. Preferably, the data is processed and stored in a manner that provides for ready and efficient access and utilization in subsequent steps, often using auxiliary data structures such as indexes or hashes.

In general, real-time microbiome data may be obtained from conducting population studies or censuses of the microbiome as it exists at a particular point in time, or over a timeseries, for the particular industrial setting. Thus samples of biological materials are collected and characterized. This characterized information is then processed and stored. Preferably, the data is processed and utilized in subsequent steps or may be stored as historic data in a manner that provides for ready and efficient access and utilization in subsequent steps.

Generally, microbiome information may be contained in any type of data file that is utilized by current sequencing systems or that is a universal data format such as for example FASTQ (including quality scores), FASTA (omitting quality scores), GFF (for feature tables), etc. This data or files may then be combined using various software and computational techniques with identifiers or other data, examples of such software and identifiers for the combining of the various types of this information include the BIOM file format and the MI(x)S family of standards developed by the Genomic Standards Consortium. For example, information from a programmable logic controller (PLC) in an industrial setting may be combined with microbial information for storage or further processing. Similarly, information from measuring-while-drilling (MWD), logging-while-drilling (LWD), and M/LWD which is provided in known formats and has known user interfaces may be combined with microbiome information for display and analysis in subsequent processing. Additionally by way of example, in agricultural settings, data from a harvesting combine regarding yield, microbiome information, and commodities price information may be displayed or stored or used for further processing. The combination and communication of these various systems can be implemented by various data processing techniques, conversions of files, compression techniques, data transfer techniques, and other techniques for the efficient, accurate, combination, signal processing and overlay of large data streams and packets.

In general, real-time, historic, and combinations and variations of this microbiome information is analyzed to provide a census or population distribution of various microbes. Unlike conventional identification of a particular species that is present, the analysis of the present invention determines in an n-dimensional space (a mathematical construct having 2, 3, 5, 12, 1000, or more dimensions), the interrelationship of the various microbes present in the system, and potentially also interrelationship of their genes, transcripts, proteins and/or metabolites. The present inventions provide further analysis to this n-dimensional space information, which analysis renders this information to a format which is more readily usable and processable and understandable. Thus, for example, by using the techniques of the present invention, the n-dimensional space information is analyzed and studied for patterns of significance pertinent to a particular industrial setting and then converted to more readily usable data such as for example a 2-dimensional color-coded plot for presentation through a HMI (Human-Machine Interface).

Additionally, the n-dimensional space information may be related, e.g., transformed or correlated with, physical, environmental, or other data such as the presence of a mineral or the geologic time period and conditions under which a particular formation was created, either by projection into the same spatial coordinates or by relation of the coordinate systems themselves, or by feature extraction or other machine learning or multivariate statistical techniques. This related n-dimensional space information may then be further processed into a more readily usable format such as a 2-dimensional representation. Further, this 2-dimensional representation and processing may, for example, be based upon particular factors or features that are of significance in a particular industrial setting. The 2-dimensional information may also be further viewed and analyzed for determining particular factors or features of significance for a system. Yet further, either of these types of 2-dimensional information may be still further processed using for example mathematical transformation functions to return them to an n-dimensional space which mathematical functions which may be based upon known or computationally determined factors or features.

Thus the present inventions provide for derived and predicted information that can be based upon the computational distillation of complex n-dimensional space microbiome information, which may be further combined with other data. This computationally distilled data or information may then be displayed and used for operational purposes in the industrial setting, it may be combined with additional data and displayed and used for operational purposes in the industrial setting, it may be alone or in combination with additional information subjected to trend, analysis, to determine features or factors of significance, it may be used for planning and operational purposes in combinations and variations of these and other utilizations.

Generally and for example, in ascertaining microbiome information the selection and sequencing of particular regions or portions of genetic materials may be used, including for example, the SSU rRNA gene (16S or 18S), the LSU rRNA gene (23S or 28S), the ITS in the rRNA operon, cpn60, and various other segments consisting of base pairs, peptides or polysaccharides for use in characterizing the microbial community and the relationships among its constituents.

In general, an embodiment of a method of the present invention may include one or more of the following steps which may be conducted in various orders: sample preparation including obtaining the sample at the designated location, and manipulating the sample; extraction of the genetic material and other biomolecules from the microbial communities in the sample; preparation of libraries with identifiers such as an appropriate barcode such as DNA libraries, metabolite libraries, and protein libraries of the material; sequence elucidation of the material (including, for example, DNA, RNA, and protein) of the microbial communities in the sample; processing and analysis of the sequencing and potentially other molecular data; and exploitation of the information for industrial uses.

For example, turning to FIG. 1, there is shown an example of a flowchart setting forth various embodiments of these processes applied across various industrial settings. Thus, sampling 101 is performed. The sampling may be for example from an agricultural, petroleum, mineral, food, surfaces, air, water, human source or subject. The samples can include for example solid samples such as soil, sediment, rock, metal counters, and food. The samples can include for example liquid samples such as petroleum, surface water, and subsurface water. The samples can include for example complex fluid and fluid mixtures such as drilling mud, and fracturing fluid. The sample once obtained has the genetic material isolated or obtained from the sample 102, which for example can be DNA, RNA, proteins and fragments of these.

A library is prepared 103 from the genetic material. In this stage of the process the library can be prepared by use of amplification, shotgun, whole molecule techniques among others. Additionally, amplification to add adapters for sequencing, and barcoding for sequences can be preformed. Shotgun by sonication, enzymatic cleavage may be performed. Whole molecules can also be sued to sequence all DNA in a sample.

Sequencing 104 is performed. Preferably, the sequencing is with a high-throughput system, such as for example 454, Illunina, PacBio, or IonTorrent.

Sequence analysis 105 is prepared. This analysis preferably can be performed using tools such as QIIME Analysis Pipeline, Machine learning, and UniFrac. Preferably, there is assigned a sequence to the sample via barcode, for among other things quality control of sequence data.

The analysis 105, is utilized in an industrial application 106. The applications can include for example, cosmetics, agriculture, animal husbandry, pharmaceuticals, space exploration, oil, petroleum, geothermal, alternative energy, and production in factories.

Figure 2:
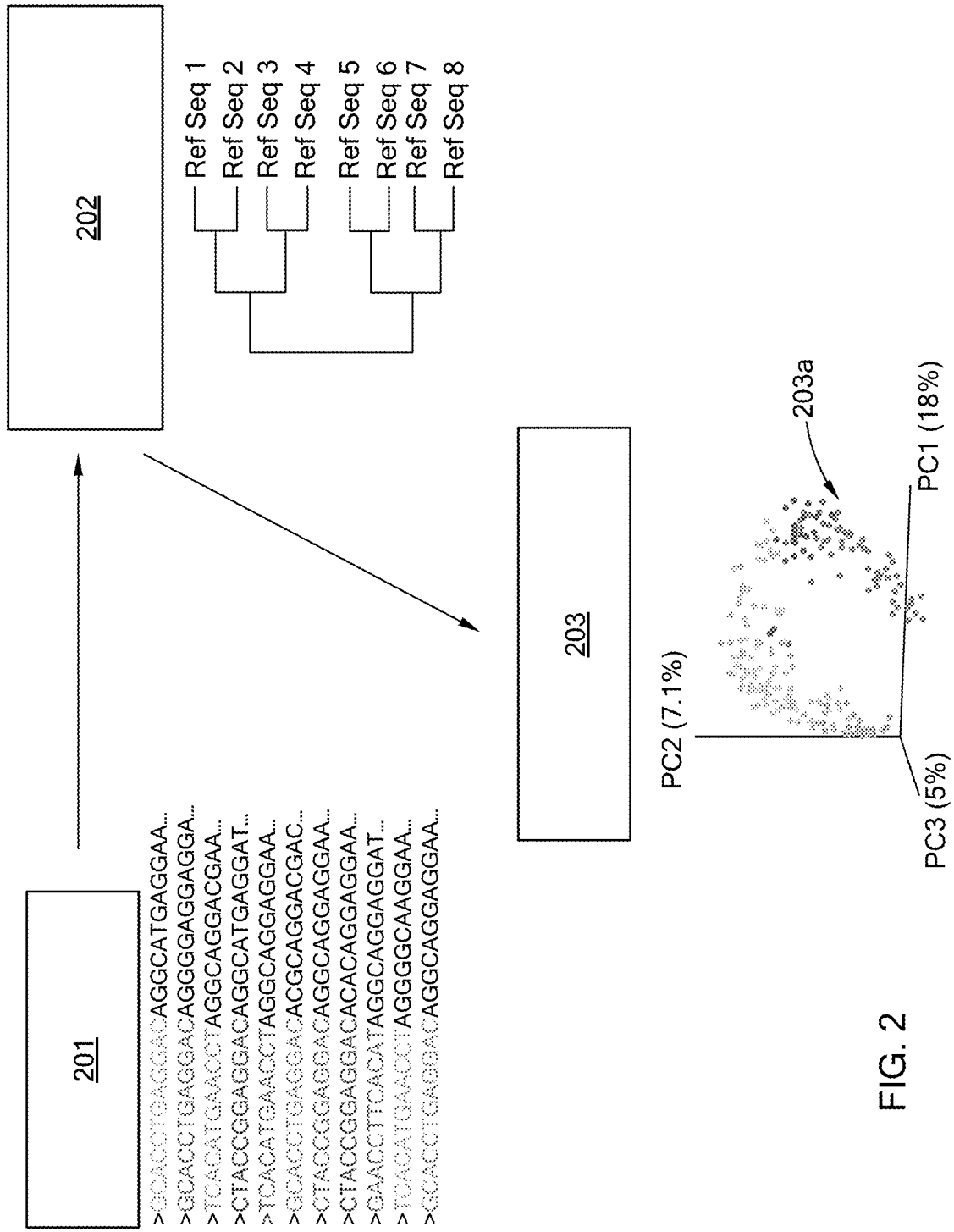
FIG. 2 is a flow chart of an embodiment of a process in accordance with the present inventions.

Turning to FIG. 2, there is illustrated an embodiment of the general processing and analysis of the biomolecular material, which is step 105 of FIG. 1. Thus as generally shown in FIG. 2, and as explained in greater detail below, generally, the processing and analysis further involves matching 201 the sequences to the samples, aligning the sequences to each other, and using the aligned sequences to build a phylogenetic tree 202, further distilling the data to form an n-dimensional plot and then a two or three dimensional plot or other graphical displays, including displays of the results of machine learning and multivariate statistical routines, and using the two or three-dimensional plot or other graphical displays to visualize patterns of the microbial communities in a particular sample over time 203.

Although HMI-type presentation of this information is presently preferred, it should be understood that such plots may be communicated directly to a computational means such as a large computer or computing cluster for performing further analysis to provide predictive information. Thus, the matched sequence samples 201 would be an example of real-time or historic microbiome information, the phylogenetic tree 202 would be an example of derived microbiome information, and portions of the graphical displays 203 which have derived microbial information combined with other data would be an example of predictive microbiome information. Thus, for example, if the information 203 related to exploration and production of hydrocarbons a uniquely colored section, e.g., 203a (grey scale used for purposes of patent figures), would indicate areas of higher oil saturation and thus predictive information of where greater hydrocarbon production would occur. It should be understood that the information section 203, if not otherwise predictive of future processes or activities, would merely be derived data.

Generally, a phylum is a group of organisms at the formal taxonomic level of Phylum based on sequence identity, physiology, and other such characteristics. There are approximately fifty bacterial phyla, which include Actinobacteria, Proteobacteria, and Firmicutes. Phylum is the classification that is a level below Kingdom, in terms of classifications of organisms. For example, or *E. coli* the taxonomy string is Kingdom: Bacteria; Phylum: Proteobacteria; Class: Gammaproteobacteria; Order: Enterobacteriales; Family: Enterobacteriaceae; Genus: *Escherichia*; and Species: *coli*.

Generally, phylogeny refers to the evolutionary relationship between a set of organisms. This relationship can be based on morphology, biochemical features, and/or nucleic acid (DNA or RNA) sequence. One can measure the changes in gene sequences and use that as a molecular clock to determine how closely or distantly the sequences, and hence the organisms that contain them, are related.

Generally, phylotype (also referred to as operational taxonomic unit ("OTU")) is analogous to "species", although phylotypes can also be defined at other taxonomic levels and these other levels are sometimes critical for identifying microbial community features relevant to a specific analysis. Because short DNA, RNA or protein sequences ("reads") can be used, these sequences may not accurately identify many organisms to the level of species, or even strain (the most detailed level of phylogenetic resolution, which is sometimes important because different strains can have different molecular functions). In cases where a "phylotype" matches a sequence or group of sequences from a known organism in the databases, it can used to say that a particular sequence is from an organism like, for example, *E. coli*.

Generally, a taxon is a group of organisms at any level of taxonomic classification. Here, taxon (plural: taxa) is a catchall term used in order to obviate the usage of the organism names repeatedly and to provide generality across taxonomic levels.

Microbial community diversity and composition may vary considerably across industrial environments and settings, and the present inventions link these changes to biotic or abiotic factors and other factors and conditions in the industrial environment to create derived and predictive information. Thus these patterns of microbial communities for example geological patterns of microbial communities or patterns of microbial communities in an industrial system (microbiosystem metrics) which are determined by the present invention can give rise to predictive information for use in the industrial setting.

Examinations of microbial populations, e.g., a census, may provide insights into the physiologies, environmental tolerances, and ecological strategies of microbial taxa, particularly those taxa which are difficult to culture and that often dominate in natural environments. Thus, this type of derived data is utilized in combination with other data in order to form predictive information.

Microbes are diverse, ubiquitous, and abundant, yet their population patterns and the factors driving these patterns were prior to the present inventions not readily understood in industrial settings and thus it is believed never effectively used for the purposes for ascertaining predictive information. Microorganisms, just like macroorganisms (i.e., plants and animals), exhibit no single shared population pattern. The specific population patterns shown by microorganisms are variable and depend on a number of factors, including, the degree of phylogenetic resolution at which the communities are examined (e.g., *Escherichia*), the taxonomic group in question, the specific genes and metabolic capabilities that characterize the taxon, and the taxon's interactions with members of other taxa. Thus, such population patterns can be determined in industrial settings and utilized as derived data for the purposes of ascertaining predictive information.

However, for certain environments, common patterns may emerge if the biogeography (e.g., microbial populations for example as determined from a census), of that particular environment is specifically examined. In particular, the structure and diversity of soil bacterial communities have been found to be closely related to soil environmental characteristics such as soil pH. A comprehensive assessment of the biogeographical patterns of, for example, soil bacterial communities requires 1) surveying individual communities at a reasonable level of phylogenetic detail (depth), and 2) examining a sufficiently large number of samples to assess spatial patterns (breadth). The studies of biogeographical patterns is not limited to soil, and will be extended to other environments, including but not limited to, any part of a living organisms, bodies of water, ice, the atmosphere, energy sources, factories, laboratories, farms, processing plants, hospitals, and other locations, systems and areas.

It should be understood that the use of headings in this specification is for the purpose of clarity, and are not limiting in any way. Thus, the processes and disclosures described under a heading should be read in context with the entirely of this specification, including the various examples. The use of headings in this specification should not limit the scope of protection afford the present inventions.

Collection

Generally, samples will be collected in a manner ensuring that microbes from the target source are the most numerous in the samples while minimizing the contamination of the sample by the storage container, sample collection device, the sample collector, other target or other non-target sources that may introduce microbes into the sample from the target source. Further, samples will be collected in a manner to ensure the target source is accurately represented by single or multiple samples at an appropriate depth (if applicable) to meet the needs of the microbiome analysis, or with known reference controls for possible sources of contamination that can be subtracted by computational analysis. Precautions should be taken to minimize sample degradation during shipping by using commercially available liquids, dry ice or other freezing methods for the duration of transit.

For example, samples can be collected in sterile, DNA/DNase/RNA/RNase-free primary containers with leak resistant caps or lids and placed in a second leak resistant vessel to limit any leakage during transport. Appropriate primary containers can include any plastic container with a tight fitting lid or cap that is suitable for work in microbiology or molecular biology considered to be sterile and free of microbial DNA (or have as little as possible) at minimum. (However, it should be noted that human DNA contamination, depending upon the markers or specific type microbe that is being looked at may not present a problem.) The primary container can also be comprised of metal, clay, earthenware, fabric, wood, etc. So long as the container may be sterilized and tested to ensure that it is ideally DNA/DNase/RNA/RNase-free (or at least contains levels of nucleic acid much lower than the biomass to be studied, and low enough concentration of nuclease that the nucleic acids collected are not degraded) and can be closed with a tight-fitting and leak resistant lid, cap or top, then it can be used as a primary container.

The primary container with the sample can then be placed into a secondary container, if appropriate. Appropriate secondary containers can include plastic screw top vessels with tight fitting lids or caps and plastic bags such as freezer-grade zip-top type bags. The secondary container can also be comprised of metal, clay, earthenware, fabric, wood, etc. So long as the container can be closed or sealed with a tight-fitting and leak resistant lid, cap or top, then it can be used as a secondary container. The secondary container can also form a seal on itself or it can be fastened shut for leak resistance.

The samples should generally be collected with minimal contact between the target sample and the sample collector to minimize contamination. The sample collector, if human, should generally collect the target sample using gloves or other barrier methods to reduce contamination of the samples with microbes from the skin. The sample can also be collected with instruments that have been cleaned. The sample collector, if machine, should be cleaned and sterilized with UV light and/or by chemical means prior to each sample collection. If the machine sample collector requires any maintenance from a human or another machine, the machine sample collector must be additionally subjected to cleaning prior to collecting any samples.

After the sample is collected and placed in a primary and secondary container, the samples will be preserved. One method of preservation is by freezing on dry ice or liquid nitrogen to between 4° C. to −80° C. Another method of preservation is the addition of preservatives such as RNAstable®, LifeGuard™ or another commercial preservative, and following the respective instructions. So long as the preservation method will allow for the microbial nucleic acid to remain stable upon storage and upon later usage, then the method can be used.

The samples will be shipped in an expedient method to the testing facility. In another embodiment, the testing of the sample can be done on location. The sample testing should be performed within a time period before there is substantial degradation of the microbial material with in the sample. So long as the sample remains preserved and there is no substantial degradation of the microbial material, any method of transport in a reasonable period of time is sufficient.

Tracers will be added to the inflow of a sampling catchment to identify the organisms present in the system that are not from the target source. The tracer can be microorganisms or anything that will allow for analysis of the flow path. For example, in an oil setting, a tracer can be used to calibrate the effectiveness of a flooding operation (water, $CO_2$, chemical, steam, etc.). The tracer will be used to determine factors such as the amount of injection fluid flowing through each zone at the production wellbore and the path of the injection fluid flow from the injection site to the production bore.

DNA/RNA Extraction

The extraction of genetic material will be performed using methods with the ability to separate nucleic acids from other, unwanted cellular and sample matter in a way to make the genetic material suitable for library construction. For example, this can be done with methods including one or more of the following, but not limited to, mechanical disruption such as bead beating, sonicating, freezing and thawing cycles; chemical disruption by detergents, acids, bases, and enzymes; other organic or inorganic chemicals. Isolation of the genetic material can be done through methods including one or more of the following, but not limited to, binding and elution from silica matrices, washing and precipitation by organic or inorganic chemicals, electroelution or electrophoresis or other methods capable of isolating genetic material.

Extractions will be done in an environment suitable to exclude microbes residing in the air or on other surfaces in the work area where the extraction is taking place. Care will be taken to ensure that all work surfaces and instruments are cleaned to remove unwanted microbes, nucleases and genetic material. Cleaning work surfaces and instruments can include, but is not limited to, spraying and/or wiping surfaces with a chlorine bleach solution, commercially available liquids such as DNAse AWAY™ or RNase AWAY™ or similar substances that are acceptable in routine decontamination of molecular biology work areas. Furthermore, aerosol barrier pipette tips used in manual, semi-automated or automated extraction process will be used to limit transfer of genetic material between instruments and samples.

Controls for Reagents for extractions and/or primary containers (when appropriate) will be tested to ensure they are free of genetic material. Testing of the reagents includes, but is not limited to performing extraction "blanks" where only the reagents are used in the extraction procedure. When necessary primary collection containers may also be tested for the presence of genetic material serving as one type of 'negative control' in PCR of the genetic material of the sample. In either case, testing the blank or negative control may be accomplished, but not limited to, spectrophotometric, fluorometric, electrophoretic, PCR or other assays capable of detecting genetic material. followed by testing the blank for the presence of genetic material by, but not limited to, spectrophotometric, fluorometric, electrophoretic, PCR or other assays capable of detecting genetic material.

The following examples are provide to illustrate various devices, tools, configurations and activities. These examples are for illustrative purposes, and should not be view as, and do not otherwise limit the scope of the present inventions.

Example 1

Collection and Extraction of DNA

Specific examination of microbial biogeography requires collection of samples, using the above general guidelines for sample containers, at a predetermined depth using a device to obtain a roughly equivalent amount of sample from each sampling location at the target location(s). The number of samples to be collected will be determined by the spatial and temporal scales over which microbial communities vary, the effect size of different factors that affect the community, and the range of conditions that need to be tested to ensure that the relevant diversity of the microbial communities is adequately represented in the samples. Further, samples can be analyzed individually or combined to produce a composite sample to represent the target sites. Samples should be preserved by storing on ice and shaded from sunlight while in transit from the field. Samples can remain at approximately 4° C. for 1-3 days for shipping or can be frozen at −20° C. or −80° C. and shipped on dry ice. Samples frozen at −80° C. can be stored indefinitely. DNA can be extracted by any method suitable for isolating the genetic material from the soil matrix.

Example 2

Agricultural Soil from a 1 Hectare Plot with Single Tube DNA Extraction

At the target site, ten points within the hectare will be selected using a stratified random sampling approach with each point marked to avoid re-sampling of the same point. At each point, a soil corer with diameter of 8 cm will be used to collect a column of soil from the top 5 cm of the mineral soil and placed in a sterile whirl type bag. The bags of soil will then be placed in a cooler to protect the samples from sunlight. Samples can be stored and shipped individually or combined to make a composite sample to represent the target site. The sample temperature should be between 4° C. and −80° C. for storage and shipment.

Once the sample(s) are received at the analysis facility, (Step 1) 0.1 g of soil from each sample will be placed in a Bead tube of the MoBio™ PowerSoil® DNA extraction kit. (Step 2) 60 µl of Solution will then be added to the sample in the Bead Tube and heated to 65° C. for 10 minutes. (Step 3) The sample will then be shaken on a vortexer at maximum speed for 2 minutes using the MoBio™ vortex adapter. After shaking the sample will be centrifuged for 1 minute at 10,000×g and the supernatant transferred to a clean tube provided with the extraction kit. (Step 4) To the supernatant, 250 µl of Solution C2 will be added and mixed by inverting 5 times and placed on ice for 5 minutes. The sample will then be centrifuged for 1 minute at 10,000×g and the supernatant transferred to a new tube provided by with the extraction kit. (Step 5) To the supernatant, 200 µl of Solution C3 will be added and mixed by inverting 5 times and placed on ice for 5 minutes. The sample will then be centrifuged for 1 minute at 10,000×g and 700 µl the supernatant transferred to a new tube provided by with the extraction kit. (Step 6) To the supernatant, 1200 µl of Solution C4 will be added and inverted 5 times to mix. (Step 7) 625 µl of the sample+C4 solution will be loaded on to a Spin Filter provided with the extraction kit and centrifuged for 1 minute at 10,000×g. The Spin Filter will be removed from the catch tube and the eluate discarded followed by replacement of the Spin Filter into the catch tube. Step 6 will be repeated until the entire volume of sample+C4 has been passed through the Spin Filter. After the final volume of eluate has been discarded, (Step 8) the Spin Filter will be placed back into the catch tube to which 500 µl Solution C5 will be added to the spin Filter and centrifuged for 30 seconds at 10,000×g. The eluate in the catch tube will be discarded and the Spin Filter placed into the catch tube and centrifuged for an additional 1 minute 10,000×g. (Step 9) The Spin Filter will be placed in a new catch tube to which 100 µl Solution C6 will be added to Spin Filter and allowed to incubate at room temperature for 1 minute. The Spin filter will then be centrifuged for 30 seconds at 10,000×g and the eluted DNA stored at −20° C. until needed.

Example 3

Timber Farm Soil Depth Profile with 96 Well Plate DNA Extraction

At the target site, a pit approximately 50 cm wide by 30 cm deep will be excavated using a common spade shovel. With the soil profile exposed, five points at 5 cm distance intervals from the surface will be selected for sampling. Starting from the deepest point of the soil profile an ethanol sterilized metal spatula will be used to collect approximately 10 g of soil and be placed in a sterile 50 ml conical centrifuge tube. Once collected, the metal spatula will be wiped clean and sterilized with ethanol before collection of the next sample in the depth profile. Each depth of the profile will be collected in the same way with the last sample coming from a depth of 5 cm. Soil will be collected from nineteen pits meaning there will be ninety-five samples for DNA extraction. The tubes of soil will then be placed in a cooler to protect the samples from sunlight. The sample temperature should be between 4° C. and −80° C. for storage and shipment.

DNA will be extracted using the MoBio™ PowerSoil® 96 well DNA extraction kit. (Step 1) The Bead Plate will be centrifuge for 1 minute at 2500×g to pellet the beads. The Square Well Mat will be removed from the Bead Plate and set aside. 0.1 to 0.25 grams of a sample will be added to each well. The last well will not have any sampled loaded and serve as the extraction blank to test the reagents and plasticware for DNA contamination. (Step 2) 750 µl of Bead Solution will be added to the wells of the Bead Plate. Then 60 µl of Solution C1 will be added as well. The Square Well Mat will be secured tightly to the plate. The sealed plates will be placed in 65° C. water bath for 10 minutes without submerging the plates. (Step 3) The Bead Plate will be placed between the aluminum plate adapters and securely fastened to the 96 Well Plate Shaker and shaken at speed 20 for 20 minutes. The plates will be removed from the shaker and centrifuged at room temperature for 6 minutes at 4500× g. (Step 4) The Square Well Mat will be removed and approximately 400-500 µl of the supernatant will be transferred from the Bead Plate into a new 96 well plate containing 250 µl of Solution C2 in each well. This solution will be mixed by pipetting up and down 4 times and then sealed with Sealing Tape. (Step 5) The sample+C2 plate will be incubated on ice for 10 minutes, then centrifuged at room temperature for 6 minutes at 4500×g. (Step 6) The Sealing Tape will be removed carefully and approximately 600 µl of the supernatant will be transferred, while avoiding the pellet, from the sample+C2 plate to a new plate containing 200 µl of Solution C3 in each well. This solution will be mixed by pipetting up and down 4 times and then sealed with Sealing Tape. (Step 7) The sample+C3 plate will be incubated on ice for 10 minutes, then centrifuged at room temperature for 6 minutes at 4500×g. (Step 8) 650 µl of C4 will be added to each well in a new 96 well plate and covered with Sealing Tape. (Step 9) The Sealing Tape will be carefully removed and approximately 750 µl of the supernatant will be transferred, while avoiding the pellet, from the sample+C3 plate to the new plate containing 650 µl of Solution C4 in each well. (Step 10) A second 650 µl aliquot of Solution C4 will be added to the sample+C4 plate and mixed by pipetting up and down 4 times. The plate will be sealed with Sealing Tape. (Step 11) A filter plate will be placed on top of a spin plate. 650 µl of the sample+C4 solution will be added to each well on the spin plate. The spin plate will be covered with centrifuge tape and then centrifuged for 5 minutes at 4500× g. (Step 12) The eluate in the bottom plate will be discarded and the spin plate will be placed back on top. (Step 13) Steps 11 and 12 will be repeated until all of the sample+C4 solution has passed through the spin plate. (Step 14) The spin plate will be placed on the bottom plate and 500 µl of C5 will be added to each well, covered with centrifuge tape and centrifuged for five minutes at 4500×g. The eluate in the bottom plate will be discarded and spin plate will be placed on top. (Step 15) The spin plate will be centrifuged for six minutes at 4500×g. (Step 16) The spin plate will be placed onto the Microplate and the centrifuge tape will be removed. (Step 17) 100 µl of Solution C6 will be added to each well, covered with centrifuge tape, and incubated at room temperature for 10 minutes. (Step 18) The spin plate will be removed and discarded and the microplate will be sealed with the sealing mat provided in the extraction kit. The DNA can be stored at −20° C. until needed.

Example 4

Crude Oil Sample from Production Well

Triplicate samples from three wells each from three different formations at three time points (t0, t0 plus one week, and t0 plus one month) will be collected. The wells will be matched (as much as possible) for geological features including production zone and distance between the surface and the oil/water interface, and physical and chemical features of the fluid (e.g., temperature, viscosity, pressure, and hydrocarbon composition). One sample from the corresponding collection tanks will be gathered when each of these samples are collected. These will be known as the "baseline" samples.

Triplicate samples will also be collected from the wellhead of six wells (n=18), three each from two different single-production-zone wells. These wells will be matched as closely as possible to the wells sampled for the baseline samples, but from different production zones. Triplicate samples will be collected from the wellheads of five wells, each producing from different, known combinations of production zones (n=15).

Oil samples will be collected in sterile 50 ml conical tubes containing 10 ml RNAlater and placed in secondary containment to prevent leakage during transit and preserve the microbes in the sample. Once the sample(s) are received at an analysis facility or a mobile analysis station, (Step 1) 200 µl of oil from each sample will be placed in a Bead tube of the MoBio™ PowerSoil® DNA extraction kit. (Step 2) 60 µL of Solution will then be added to the sample in the Bead Tube and heated to 65° C. for 10 minutes. (Step 3) The sample will then be shaken on a vortexer at maximum speed for 2 minutes using the MoBio™ vortex adapter. After shaking the sample will be centrifuged for 1 minute at 10,000×g and the supernatant transferred to a clean tube provided with the extraction kit. (Step 4) To the supernatant, 250 µl of Solution C2 will be added and mixed by inverting 5 times and placed on ice for 5 minutes. The sample will then be centrifuged for 1 minute at 10,000×g and the supernatant transferred to a new tube provided by with the extraction kit. (Step 5) To the supernatant, 200 µl of Solution C3 will be added and mixed by inverting 5 times and placed on ice for 5 minutes. The sample will then be centrifuged for 1 minute at 10,000×g and 700 µl the supernatant transferred to a new tube provided by with the extraction kit. (Step 6) To the supernatant, 1200 µl of Solution C4 will be added and inverted 5 times to mix. (Step 7) 625 µl of the sample+C4 solution will be loaded on to a Spin Filter provided with the extraction kit and centrifuged for 1 minute at 10,000×g. The Spin Filter will be removed from the catch tube and the eluate discarded followed by replacement of the Spin Filter into the catch tube. Step 7 will be repeated until the entire volume of sample+C4 has been passed through the Spin Filter. After the final volume of eluate has been discarded, (Step 8) the Spin Filter will be placed back into the catch tube to which 500 µl Solution C5 will be added to the spin Filter and centrifuged for 30 seconds at 10,000×g. The eluate in the catch tube will be discarded and the Spin Filter placed into the catch tube and centrifuged for an additional 1 minute 10,000×g. (Step 9) The Spin Filter will be placed in a new catch tube to which 100 µl Solution C6 will be added to Spin Filter and allowed to incubate at room temperature for 1 minute. The Spin filter will then be centrifuged for 30 seconds at 10,000×g and the eluted DNA stored at −20° C. until needed.

Example 5

Subsurface Sediment from Exploration Borehole

At the target site, samples will be collected from the material brought to the surface by the drill with the depth of the sample estimated from the length of drill inserted into the borehole. Approximately 50 g of sediment from the drill will be collected using an ethanol sterilized metal spatula and placed into a sterile whirl type bag and stored in cooler. The metal spatulas will be wiped clean and ethanol sterilized in between the collection of each sample. The sample temperature should be between 4° C. and −80° C. for storage and shipment.

Once the sample(s) are received at an analysis facility or mobile testing station, (Step 1) 0.1 g of soil from each sample will be placed in a Bead tube of the MoBio™ PowerSoil® DNA extraction kit. (Step 2) 60 µL of Solution will then be added to the sample in the Bead Tube and heated to 65° C. for 10 minutes. (Step 3) The sample will then be shaken on a vortexer at maximum speed for 2 minutes using the MoBio™ vortex adapter. After shaking the sample will be centrifuged for 1 minute at 10,000×g and the supernatant transferred to a clean tube provided with the extraction kit. (Step 4) To the supernatant, 250 µl of Solution C2 will be added and mixed by inverting 5 times and placed on ice for 5 minutes. The sample will then be centrifuged for 1 minute at 10,000×g and the supernatant transferred to a new tube provided by with the extraction kit. (Step 5) To the supernatant, 200 µl of Solution C3 will be added and mixed by inverting 5 times and placed on ice for 5 minutes. The sample will then be centrifuged for 1 minute at 10,000×g and 700 µl the supernatant transferred to a new tube provided by with the extraction kit. (Step 6) To the supernatant, 1200 µl of Solution C4 will be added and inverted 5 times to mix. (Step 7) 625 µl of the sample+C4 solution will be loaded on to a Spin Filter provided with the extraction kit and centrifuged for 1 minute at 10,000×g. The Spin Filter will be removed from the catch tube and the eluate discarded followed by replacement of the Spin Filter into the catch tube. Step 7 will be repeated until the entire volume of sample+C4 has been passed through the Spin Filter. After the final volume of eluate has been discarded, (Step 8) the Spin Filter will be placed back into the catch tube to which 500 µl Solution C5 will be added to the Spin Filter and centrifuged for 30 seconds at 10,000×g. The eluate in the catch tube will be discarded and the Spin Filter placed into the catch tube and centrifuged for an additional 1 minute 10,000×g. (Step 9) The Spin Filter will be placed in a new catch tube to which 100 µl Solution C6 will be added to Spin Filter and allowed to incubate at room temperature for 1 minute. The Spin filter will then be centrifuged for 30 seconds at 10,000×g and the eluted DNA stored at −20° C. until needed.

Library Preparation

Amplification

Genetic material from the samples will be subjected to polymerase chain reaction (PCR) to amplify the gene of interest and encode each copy with barcode unique to the sample. Generally, PCR amplifies a single or a few copies of a piece of DNA across several orders of magnitude, generating thousands to millions, or more, of copies of a particular DNA sequence using a thermostable DNA polymerase. PCR will be used to amplify a portion of specific gene from the genome of the microbes present in the sample. Any method which can amplify genetic material quickly and accurately can be used for library preparation.

The PCR primer will be designed carefully to meet the goals of the sequencing method. The PCR primer will contain a length of nucleotides specific to the target gene, may contain an adapter that will allow the amplicon, also known as the PCR product, to bind and be sequenced on a high-throughput sequencing platform, and additional nucleotides to facilitate sequencing. The portion of the gene with adapters, barcode and necessary additional nucleotides is known as the "amplicon." It being understood that future systems may not use, or need, adaptors.

The microbial ribosome is made up component proteins and non-coding RNA molecules, one of which is referred to as the 16S ribosomal RNA (or 16S rRNA). The 16S subunit is a component of the small subunit (SSU) of bacterial and archaeal ribosomes. It is 1.542 kb (or 1542 nucleotides) in length. The gene encoding the 16S subunit is referred to as the 16S rRNA gene. The 16S rRNA gene is used for reconstructing phylogenies because it is highly conserved between different species of bacteria and archaea, meaning that all of these organisms encode it in their genomes and it can be easily identified in genomic sequences, but it additionally contains regions that are highly variable, so there is a phylogenetic signature in the sequence of the gene. As a result of these same properties, batch sequencing of all of the 16S rRNA gene sequence in a sample containing many microbial taxa are informative about which microbial taxa are present. These studies are made possible by the remarkable observation that a small fragment of the 16S rRNA gene is sufficient as a proxy for the full-length sequence for many community analyses, including those based on a phylogenetic tree. Although the phylogenetic trees produced from approximately 250-base reads from the 454 Life Sciences™ (Roche) GS FLX instrument are relatively inaccurate, they are still much better, as has been identified and is known to the art, than the "star phylogeny," (phylogeny that assumes all species are equally related), that all non-phylogenetic methods for comparing communities use implicitly (e.g., by counting how many species are shared). However, such trees should, at most, be used as a guide to community comparisons and not for inferring true phylogenetic relationships among reads. Advances in sequencing technology, such as the availability of 400-base reads with the Titanium™ kit from Roche; the Illumina™ platforms which can produce 450 Gb per day, and in the course of a 10.8 day run produces 1.6 billion 100-base paired-end reads (HiSeq2000) or for single-day experiments can generate 1.5 Gb per day from 5 million 150-base paired-end reads (MiSeq™), or in the future, the availability of instruments providing 1500-base single-molecule reads, as reported by Pacific Biosciences™, will also improve the accuracy/productivity of existing methods for building phylogenetic trees and classifying functions of metagenomic reads.

Although metagenomics and other alternative techniques provide insight into all of the genes (and potentially gene functions) present in a given community, 16S rRNA-based studies are extremely valuable given that they can be used to discover and record unexplored biodiversity and the ecological characteristics of either whole communities or individual microbial taxa. 16S rRNA phylogenies tend to correspond well to trends in overall gene content. Therefore the ability to relate trends at the species level to host or environmental parameters has proven immensely powerful to understanding the relationships between the microbes and the world.

Alternative microbiome measurement techniques provide important information that is complementary to 16S rRNA or other marker-gene data: shotgun metagenomics provides genome content for the entire microbiome; transcriptomics measures gene expression by microbes, indicating which genes are actually being used by the microbes; proteomics measures actual production of enzymes and other functional proteins in the microbiome; metabolomics directly measures metabolite content in a sample.

Generally, analysis of ribosomal genes (SSU, LSU, ITS) will be used for the determination and characterization of microbes in industrial settings where the only requirement for choosing the particular gene for amplification is that the gene is at least somewhat conserved between different species of microbes. For instance, the amplification, sequencing and analysis of the small subunit ("SSU") of the ribosomal gene (16S rRNA gene) would be used for bacteria and archaea while analysis of the microeukarytotes such as nematodes, ciliates and amoeba would analyze the small subunit ribosomal gene (18S rRNA gene) common in these organisms. Further LSU, ITS and mitochondrial marker such as Cytb or cox1, generally may also be used and could provide enhanced performance. Fungal populations may also be characterized by the intragenic transcribed spacer gene ("ITS gene") in addition to 18S rRNA gene. Furthermore, the large subunit ribosomal gene ("LSU") could be analyzed alone or in combination with portions of the SSU in a single amplicon. The genetic material for any analysis could be derived from DNA or cDNA (i.e., complementary DNA) produced from the reverse transcription of RNA isolated from the target sample or samples.

Complete marker genes generally cannot, because of their length, be sequenced using high-throughput methods. However, the use of PacBio or Moleculo can provide the ability to obtain such a complete sequence. Therefore, a shorter region of the marker gene sequence must be selected to act as proxy. Currently, there is no consensus on a single best region, and consequently different groups are sequencing different or multiple regions. This diversity of methods hinders direct comparisons among studies. Standardization on a single region would be helpful on this front. Of the nine variable regions in the 16S rRNA gene, several of the more popular regions include the regions surrounding V2, V4, and V6. Generally, a combination of variable and moderately conserved regions appears to be optimal for performing analyses at different phylogenetic depths. Both the choice of region and the design of the primers are crucial, and poor design of primers can lead to radically different experimental conclusions. Additionally, primer bias due to differential annealing leads to the over- or underrepresentation of specific taxa can lead to some groups being missed entirely if they match the consensus sequence poorly. Issues of primer bias can be important. For example, although some widely used primers such as 8F, 337F, 338R, 515F, 915F, 930R, 1046R, and 1061R match >95% of the sequences in Ribosome Database Project (RDP) from all of the major bacterial phyla in the gut (Firmicutes, Bacteroidetes, Actinobacteria, Verrucomicrobia, and Proteobacteria), others miss specific divisions. For example, 784F is biased against Verrucomicrobia; 967F matches <5% of Bacteroidetes; and 1492R matches 61% of Actinobacteria, 54% of Proteobacteria, and fewer than half of the other divisions. Comparisons of relative abundance among different studies should thus be treated with caution. However, meta-analysis of presence/absence data from different studies is particularly useful for revealing broad trends, even when different studies use different primers.

As more sequence data and better taxonomic assignments become available, improved primer sets, with better coverage (including primers for archaea and eukaryotes), will likely provide a substantial advantage over present degenerate primer techniques. Specifically, 16S rRNA and 18s rRNA reads from metagenomic studies provide a source of sequences that is not subject to PCR primer bias (although other biases are present) and therefore covers taxa that are missed by existing but popular primer sets, although in practice exploiting this information has been quite challenging. Another promising approach is the use of miniprimers, which, together with an engineered DNA polymerase, may allow greater coverage of desired groups.

Furthermore, improvements in the ability to produce high quantities of primers (e.g. millions of individual primers) will enable amplification of high quantities of regions (e.g. millions of individual regions), which may be distinct to each microbe or targeted at multiple sites obtained from existing databases or from shotgun sequencing. Such an application could be used to improved discrimination and/or prediction for a particular environment and target parameter (e.g. oil saturation in a reservoir). For example, we might determine that a collection of genes related to hydrocarbon reduction or oxidation are predictive of oil/water saturation, and then design primer sets against all of such genes identified via shotgun sequencing of a series of samples obtained from wells with varying oil/water saturation levels.

The primers designed for amplification will be well-suited for the phylogenetic analysis of sequencing reads. Thus, the primer design will be based on the system of sequencing, e.g., chain termination (Sanger) sequencing or high-throughput sequencing. Within the system, there are also many options on the method. For example, for high-throughput sequencing, the sequencing can be performed by, but is not limited to, 454 Life Sciences™ Genome Sequencer FLX (Roche) machine or the Illumina™ platforms (MiSeq™ or HiSeq™). These will be described more in the Sequencing section below.

Barcoding

High-throughput sequencing, described below, has revolutionized many sequencing efforts, including studies of microbial community diversity. High-throughput sequencing is advantageous because it eliminates the labor-intensive step of producing clone libraries and generates hundreds of thousands of sequences in a single run. However, two primary factors limit culture-independent marker gene-based analysis of microbial community diversity through high-throughput sequencing: 1) each individual run is high in cost, and 2) separating a single plate across multiple runs is difficult. For example, analysis of multiple libraries on the 454™/Roche sequencers has room for up to a maximum of only 16 independent samples, which have to be physically segregated using manifolds on the sequencing medium. These separation manifolds block wells on the sequencing plate from accommodating bead-bound DNA template molecules, and thus limit the number of output sequences.

A solution to these limitations is barcoding. For barcoding, a unique tag will be added to each primer before PCR amplification. Because each sample will be amplified with a known tagged (barcoded) primer, an equimolar mixture of PCR-amplified DNA can be sequenced from each sample and sequences can be assigned to samples based on these unique barcodes. The presence of these assigned barcodes allow for independent samples to be combined for sequencing, with subsequent bioinformatic separation of the sequencer output. By not relying on physical separators, this procedure maximizes sequence space and multiplexing capabilities. This technique will be used to process many samples (eg 25, 200, 1000, and above) as many as 25 samples in a single high-throughput sequencing run. This number will be increased depending on advances in high-throughput sequencing technology, without limit to the number of samples to be sequenced in a single high-throughput sequencing run.

Barcodes, or unique DNA sequence identifiers, have traditionally been used in different experimental contexts, such as sequence-tagged mutagenesis (STM) screens where a sequence barcode acts as an identifier or type specifier in a heterogeneous cell-pool or organism-pool. However, STM barcodes are usually 20-60 bases (or nt) long, are pre-selected or follow ambiguity codes, and exist as one unit or split into pairs. Such long barcodes are not particularly compatible with available high-throughput sequencing platforms because of restrictions on read length.

Although very short (2- or 4-nt) barcodes can be used with high-throughput sequencing platforms, a more definitive assignment of samples and/or for enhanced multiplexing capabilities can be accomplished by lengthening the barcodes or variations in the fixed forward and reverse linkers used to generate the initial cDNA libraries. Shorter barcodes also have a steeper trade-off between number of possible barcodes and the minimum number of nucleotide variations between individual barcodes.

Existing barcoding methods have limits both in the number of unique barcodes used and in their ability to detect sequencing errors that change sample assignments (this robustness is especially important for sample assignment because the 5' end of the read (sequence for one strand of nucleic acid in a sample) is somewhat more error-prone). Barcodes based on error-correcting codes, which are widely used in devices in other technologies like telecommunications and electronics, will be applied for high-throughput sequencing barcoding purposes. A class of error-correcting codes called Hamming codes, which use a minimum amount of redundancy and will be simple to implement using standard linear algebra techniques. Hamming codes, like all error-correcting codes, employ the principle of redundancy and add redundant parity bits to transmit data over a noisy medium. Sample identifiers will be encoded with redundant parity bits. Then the sample identifiers will be "transmitted" as codewords. Each base (A, T, G, C) will be encoded using 2 bits and using 8 bases for each codeword. Therefore, 16-bit codewords will be transmitted. The codeword and bases is not limited to these numbers, as any number of bits and codewords can be designed by a person of ordinary skill in the art. The design of the barcode is based on the goals of the method. Hamming codes are unique in that they use only a subset of the possible codewords, particularly those that lie at the center of multidimensional spheres (hyperspheres) in a binary subspace. Single bit errors fall within hyperspheres associated with each codeword, and thus they can be corrected. Double bit errors do not fall within hyperspheres associated with each codeword, and thus they can be detected but not corrected.

Another encoding schemes, such as Golay codes, will also be used for barcoding. Golay codes of 12 bases can correct all triple-bit errors and detect all quadruple-bit errors. The extended binary Golay code encodes 12 bits of data in a 24-bit word in such a way that any 3-bit errors can be corrected or any 7-bit errors can be detected. The perfect binary Golay code, has codewords of length 23 and is obtained from the extended binary Golay code by deleting one coordinate position (conversely, the extended binary Golay code is obtained from the perfect binary Golay code by adding a parity bit). In standard code notation the codes have parameters corresponding to the length of the codewords, the dimension of the code, and the minimum Hamming distance between two codewords, respectively.

In mathematical terms, the extended binary Golay code consists of a 12-dimensional subspace W of the space $V=F_2^{24}$ of 24-bit words such that any two distinct elements of W differ in at least eight coordinates. Equivalently, any non-zero element of W has at least eight non-zero coordinates. The possible sets of non-zero coordinates as w ranges over W are called codewords. In the extended binary Golay code, all code words have the Hamming weights of 0, 8, 12, 16, or 24. Up to relabeling coordinates, W is unique.

Figure 3:
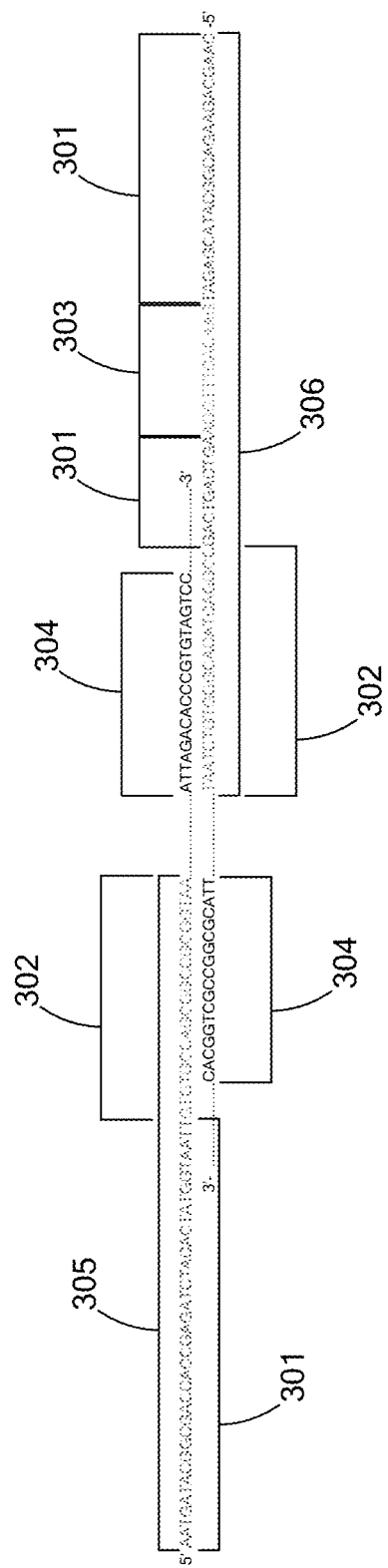
FIG. 3 is an illustration of an embodiment of barcoded primers for high-throughput sequencing in accordance with the present inventions.

FIG. 3 shows an example of the general design for barcoded primers for high-throughput sequencing. The primer will be designed to include nucleotides specific for the sequencing platform 301; nucleotides specific for the gene of interest 302; nucleotides for the Golay barcode 303; and the nucleotides of the gene 304. Upon amplification, one contiguous string of nucleotides known as the "forward" primer 305 will be formed from the platform specific sequencing adaptors 301 and the gene specific primer and linker 302. Additionally formed upon amplification will be one contiguous string of nucleotides known as the "reverse" primer formed from the platform specific sequencing adaptors 301, the gene specific primer and linker 302, and the barcode 303.

Figure 4:
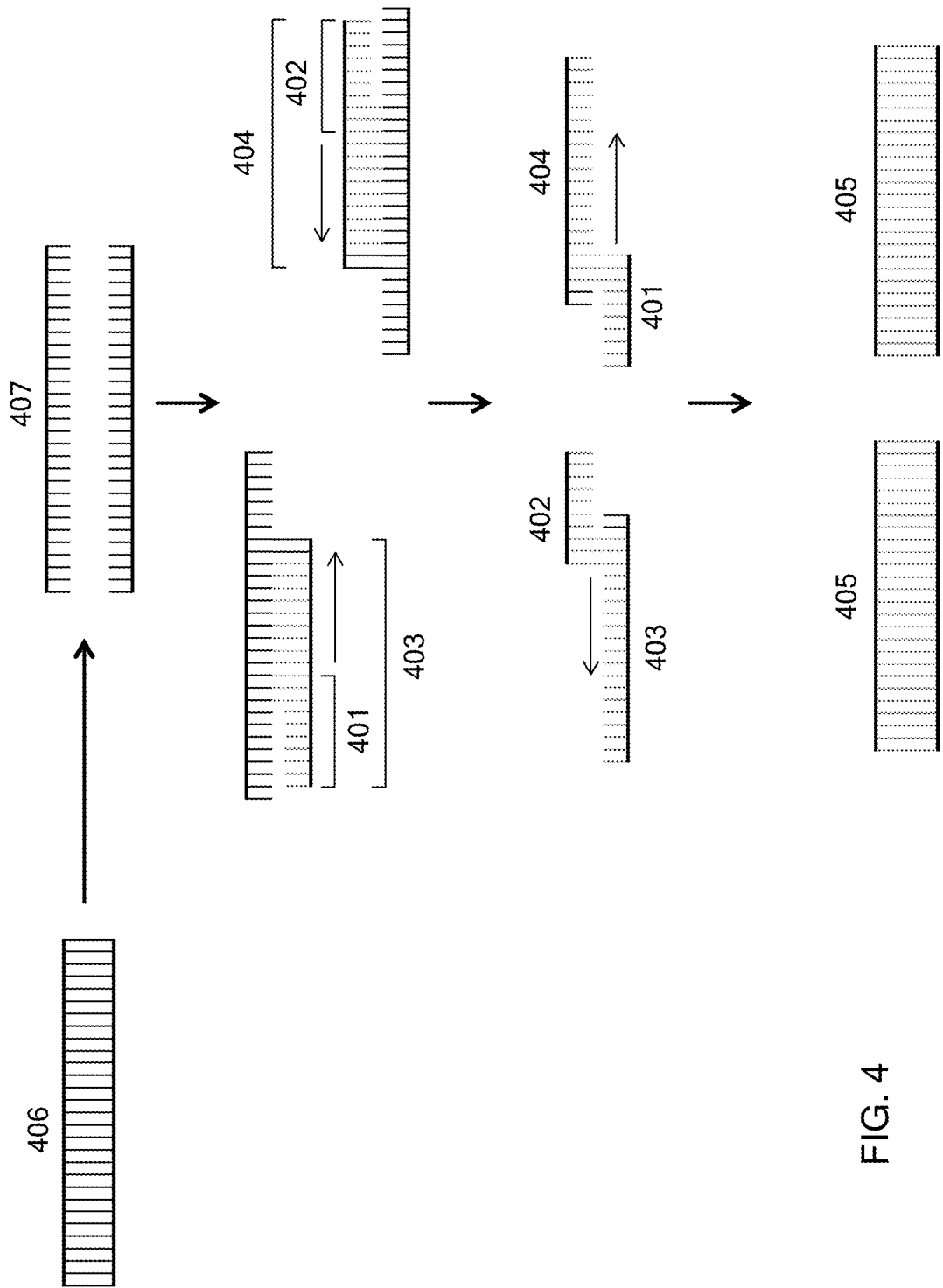
FIG. 4 is an illustration of an embodiment of polymerase chain reaction (PCR) in accordance with the present inventions.

FIG. 4 shows the general scheme for PCR using barcoded primers, designed as previously described. Double stranded target DNA 406 is denatured 407. Strands 401 and 402 will be annealed to the gene via the gene specific primer and linker (FIG. 3, 302). Thermostable DNA polymerase extends primers creating strands 403 and 404. Strands 403 and 404 will be denatured from the target DNA. Then strand 401 will be annealed to strand 404 while strand 402 will be annealed to strand 403. Through amplification, new strands 405 are produced. Strand 405 is a barcoded amplicon that can be sequenced. Further, other error-correcting codes may be utilized such as Gray codes, low-density parity check codes, etc.

The barcoded high-throughput sequencing technique yields provides a robust description of the changes in bacterial community structure across the sample set. A high-throughput sequencing run is expensive, and the large number of custom primers required only adds to this cost. However, the barcoding technique allows for thousands of samples to be analyzed simultaneously, with each community analyzed in considerable detail. Although the phylogenetic structure and composition of the surveyed communities can be determined with a high degree of accuracy, the barcoded high-throughput sequencing method may not allow for the identification of bacterial taxa at the finest levels of taxonomic resolution. However, with increasing read lengths in sequencing, this constraint will gradually become less relevant.

Example 6

In one example, specifically for the Illumina™ sequencing machinery (described below), the following primers will be designed for amplification of 16S rRNA. The primer sequences in this protocol are always listed in the 5'->3' orientation.

515f PCR Primer Sequence—Forward Primer
Field description (space-delimited):
1. 5' Illumina™ adapter
2. Forward primer pad
3. Forward primer linker
4. Forward primer (515f)

(SEQ ID NO: 1)
AATGA TACGG CGACC ACCGA GATCT ACACT ATGGT

AATTG TGTGC CAGCM GCCGC GGTAA

806r PCR Primer Sequence—Reverse Primer, Barcoded
Sheet of primer constructs contains 2168 Golay barcoded reverse PCR primers generated specifically for this set of primers.
Field description (space-delimited):
1. Reverse complement of 3' Illumina™ adapter
2. Golay barcode
3. Reverse primer pad
4. Reverse primer linker
5. Reverse primer (806r)

(SEQ ID NO: 2)
CAAGC AGAAG ACGGC ATACG AGAT XXXXXXXXXXXX

AGTCA GTCAG CCGGA CTACH VGGGT WTCTA AT

Illumina™ PCR Conditions: 515f-806r Region of the 16S rRNA Gene:
Complete Reagent Recipe (Master Mix) for 1×PCR Reaction

| | |
|---|---|
| PCR Grade H2O (note a) | 13.0 μL |
| 5 Primer Hot MM (note b) | 10.0 μL |
| Forward primer (10 μM) | 0.5 μL |
| Reverse primer (10 μM) | 0.5 μL |
| Template DNA | 1.0 μL |
| Total reaction volume | 25.0 μL |

Notes:
PCR grade water was purchased from MoBio™ Laboratories (MoBio™ Labs: Item#17000-11)
Five Prime Hot Master Mix (5 prime: Item# 2200410)
Final primer concentration of mastermix: 0.2 μM Thermocycler Conditions for 96 Well Thermocyclers:
94° C. 3 minutes
94° C. 45 seconds
50° C. 60 seconds
72° C. 90 seconds
Repeat steps 2-4 35 times
72° C. 10 minutes
4° C. HOLD
Thermocycler Conditions for 384 Well Thermocycler
94° C. 3 minutes
94° C. 60 seconds
50° C. 60 seconds
72° C. 105 seconds
Repeat steps 2-4 35 times
72° C. 10 minutes
4° C. HOLD The samples will be amplified in triplicate, meaning each sample will be amplified in 3 replicate 25 μL PCR reactions. The triplicate PCR reactions will be combined for each sample into a single volume. The combination will result in a total of 75 μL of amplicon for each sample. The amplicons from different samples will not be combined at this point. The amplicons for each sample will be run on an agarose gel. Expected band size for 515f/806r is roughly 300-350 bp. Amplicons will be quantified using Picogreen's® instructions. An equal amount of amplicon from each sample will be combined into a single, sterile tube. Generally, 240 ng of DNA per sample will be pooled. However, higher amounts can be used if the final pool will be gel isolated or when working with low biomass samples. When working with multiple plates of samples, it is typical to produce a single tube of amplicons for each plate of samples. The amplicon pool will be cleaned using MoBio™ UltraClean® PCR Clean-Up Kit #12500, following the instructions provided therein. If working with more than 96 samples, the pool will need to be split evenly for cleaning and then recombined. If spurious bands are present on the previously mentioned agarose gel, half of the final pool will be run on a gel and then gel extracted to select only the target bands. The concentration of the final pool will be determined fluorometrically with PicoGreen® ds DNA reagent, or equivalent assay, as spectrophotometric methods are not suitable for quantification. However, the 260 nm/280 nm ratio should be determined spectrophotometrically as this is a measure of sample purity and critical to successful sequencing with the ratio between 1.8 and 2.0. An aliquot of this final sample will be used for sequencing along with sequencing primers listed below.

Read 1 sequencing primer:
Field description (space-delimited):
1, Forward primer pad
2, Forward primer linker
3, Forward primer (SEQ ID NO: 3)
TATGG TAATT GTGTG CCAGC MGCCG CGGTA A Read 2 sequencing primer:
Field description (space-delimited):
1, Reverse primer pad
2, Reverse primer linker
3, Reverse primer (SEQ ID NO: 4)
AGTCA GTCAG CCGGA CTACH VGGGT WTCTA AT Index sequence primer
Field description (space-delimited):
1. Reverse complement of reverse primer
2. Reverse complement of reverse primer linker
3. Reverse complement of reverse primer pad (SEQ ID NO: 5)
ATTAG AWACC CBDGT AGTCC GGCTG ACTGA CT Example 7

In another example, for each sample, the 16S rRNA gene will be amplified using a primer set including:
Forward primer (5'-GCCTTGCCAGCCCGCTCAGTCAGAGTTTGAT-CCTGGCTCAG-3') (SEQ ID NO: 6) which contains the 454 Life Sciences™ primer B, the broadly conserved bacterial primer 27F, and a 2-base linker sequence ("TC");
Reverse primer (5'-GCCTCCCTCGCGCCATCAGNNNNNNNNNNNN-NCATGCTGCCTCCCGTAGGA GT-3') (SEQ ID NO: 7) which contains the 454 Life Sciences™ primer A, the bacterial primer 338R, a "CA" inserted as a linker between the barcode and the rRNA primer (with the specific linker depending on the region of sequence targeted by the primer and which, unlike the PCR primer which is designed to be complimentary to the target sequences, is specifically designed to not be complimentary to the target sequences so the base pairing interactions are disrupted in all target sequences at this position—if this linker were not present, some barcodes would anneal to the target, while some would not, leading to barcode-specific PCR biases) and a unique 12-bp error-correcting Golay barcode used to tag each PCR product (designated by NNNNNNNNNNNN). PCRs will consist of 0.25 µL (30 µM) of each forward and reverse primer, 3 µL of template DNA, and 22.5 µL of Platinum® PCR SuperMix by Invitrogen™. Samples will be denatured at 94° C. for 3 min, then amplified by using 35 cycles of 94° C. for 45 seconds, 50° C. for 30 seconds, and 72° C. for 90 seconds. A final extension of 10 minutes at 72° C. will be added at the end of the program to ensure complete amplification of the target region. All samples will be amplified in triplicate. Negative controls (both no-template and template from unused cotton swabs (referring back to Example 6)) will be included in all steps of the process to check for primer or sample DNA contamination. All aliquoting and diluting of primers, as well as assembly of PCRs, will be done in a PCR hood in which all surfaces and pipettes had been decontaminated with DNA AWAY™ by Molecular BioProducts™ and exposed to UV light for 30 minutes.

A composite sample for DNA sequencing will be prepared by pooling approximately equal amounts of PCR amplicons from each sample. The replicate PCRs for each sample will be combined and cleaned with the Mobio™ UltraClean®-htp PCR Clean-up kit as directed by the manufacturer. Each sample (3 µL) was then quantified by using PicoGreen® dsDNA reagent by Invitrogen™ in 1× Tris-EDTA (pH 8.2) in a total volume of 200 µL on black, 96-well microtiter plates on a BioTek™ Synergy™ HTP microplate reader by BioTek Instruments, using the 480/520-nm excitation and emission filter pair. Once quantified, the appropriate volume of the cleaned PCR amplicons will be combined in a sterile, 50-mL polypropylene tube and precipitated on ice with sterile 5 M NaCl (0.2 M final concentration) and 2 volumes of ice-cold 100% ethanol for 45 minutes. The precipitated DNA will be centrifuged at 7,800 g for 40 minutes at 4° C., and the resulting will be washed with an equal volume of 70% ethanol and will be centrifuged again at 7,800 g for 20 minutes at 4° C. The supernatant will be removed, and the pellet will be air-dried for 7 minutes at room temperature, then resuspended in 100 µL of DNA-nuclease free water. The sample will be then ready for sequencing.

Example 8

Small-subunit ribosomal genes (16S) will be amplified using universal 515F (5'-GTGCCAGCMGCCGCGGTAA-3') (SEQ ID NO: 8) and 1391R (5'-GACGGGC-GGTGWGTRCA-3') (SEQ ID NO: 9) primers for bacterial 16S rRNA genes. The PCR reaction will contained 1×PCR Buffer from Invitrogen, 2.5 mM MgCl$_2$, 0.2 µM of each primer, 0.2 µM dNTPs, 0.5 U Taq DNA polymerase by Invitrogen™ and 1.0 µl template DNA. Amplification will be accomplished by initial denaturation at 94° C. for 3 minutes followed by 25 cycles of 94° C. for 30 seconds, 50° C. for 30 seconds and 72° C. for 30 seconds with a final extension at 72° C. for 10 minutes. Each DNA sample will be amplified in triplicate and the amplicons will be pooled by plot and run on a 1.5% agarose gel. The bands will be purified using the Promega™ Wizard® SV Gel and PCR Clean-Up System. The sample will be then ready for sequencing.

Example 9

In another example, a portion of the 16S small-subunit ribosomal gene (positions 27 to 338 [V1 and V2]; *Escheri-*

*chia coli* numbering) will be amplified using a 27F primer with a Roche 454 ™ A pyrosequencing adapter, while the 338R primer will contain a 12-bp bar-code sequence, a TC linker, and a Roche 454™ B sequencing adapter. The particular gene region has been shown to be very appropriate for accurate taxonomic classification of bacterial sequences, because other regions of the 16S rRNA gene can lead to significant misclassification of sequences. The barcode for each sample will be unique and error correcting to facilitate sorting of sequences from a single pyrosequencing run. PCRs will be conducted with 30 µM of each forward and reverse primer, 1.5 µl template DNA, and 22.5 µl Platinum® PCR SuperMix by Invitrogen™. Each sample will be amplified in triplicate, pooled, and cleaned using a MoBio™ 96 htp PCR cleanup kit. Equal amounts of PCR product for each sample will be combined in a single tube for sequencing.

Sequencing

The vast majority of life on earth is microbial, and the vast majority of these microbial species has not been, and is not capable of being easily cultured in the laboratory. Consequently, our primary source of information about most microbial species consists of fragments of their DNA sequences. Sequencing a DNA library will be done on a platform capable of producing many sequences for each sample contained in the library. High-throughput sequencing technologies have allowed for new horizons in microbial community analysis by providing a cost-effective method of identifying the microbial OTUs that are present in samples. These studies have drastically changed our understanding of the microbial communities in the human body and on the planet. This development in sequencing technology, combined with more advanced computational tools that employ metadata to relate hundreds of samples to one another in ways that reveal clear biological patterns, has reinvigorated studies of the 16S rRNA and other marker genes. Studies of 16S rRNA genes provide a view of which microbial taxa are present in a given sample because these genes provide an excellent phylogenetic marker. Although alternative techniques, such as metagenomics, provide insight into all of the genes (and potentially gene functions) present in a given community, 16S rRNA-based surveys are extraordinarily valuable given that they can be used to document unexplored biodiversity and the ecological characteristics of either whole communities or individual microbial taxa. Perhaps because 16S rRNA phylogenies tend to correspond well to trends in overall gene content, the ability to relate trends at the species level to host or environmental parameters has proven immensely powerful. The DNA encoding the 16S rRNA gene has been widely used to specify bacterial taxa, since the region can be amplified using PCR primers that bind to conserved sites in most or all species, and large databases are available relating 16S rRNA sequences to bacterial phylogenies. However, as previously discussed, other genes can be used to specify the taxa, such as 18S, LSU, ITS, and SSU (e.g., 16S). For the purposes of bacteria, cpn60 or ftsZ, or other markers, may also be utilized.

New technologies have led to extraordinary decreases in sequencing costs. This rapid increase in sequencing capacity has led to a process in which newer sequencing platforms generate datasets of unprecedented scale that break existing software tools: new software is then developed that exploits these massive datasets to produce new biological insight, but in turn the availability of these software tools prompts new experiments that could not previously have been considered, which lead to the production of the next generation of datasets, starting the process again.

High-Throughput Sequencing

With the advent of high-throughput sequencing, characterization of the nucleic acid world is proceeding at an accelerated pace. Three major high-throughput sequencing platforms are in use today: 1) the Genome Sequencers from Roche/454 Life Sciences™ [GS-20 or GS-FLX]; 2) the 1G Analyzer from Illumina™/Solexa™ which includes the MiSeq™ and the HiSeq™; and 3) the SOLiD™ System from Applied Biosystems™. Comparison across the three platforms reveals a trade-off between average sequence read length and the number of DNA molecules that are sequenced. The Illumina™/Solexa™ and SOLiD systems provide many more sequence reads, but render much shorter read lengths than the 454™/Roche Genome Sequencers. This makes the 454™/Roche platform appealing for use with barcoding technology, as the enhanced read length facilitates the unambiguous identification of both complex barcodes and sequences of interest. However, even reads of less than 100 bases can be used to classify the particular microbe in phylogenetic analysis. Any platform, for example, Illumina™, providing many reads and read lengths of a predetermined necessary length, for example, 150 base pairs or 100 base pairs, is acceptable for this method.

Because the accuracy of phylogenetic reconstruction depends sensitively on the number of informative sites, and tends to be much worse below a few hundred base pairs, the short sequence reads produced from high-throughput sequencing, which are 100 base pairs on average for the GS 20 (Genome Sequencer 20 DNA Sequencing System, 454 Life Sciences™), may be unsuitable for performing phylogenetically based community analysis. However, this limitation can be at least partially overcome by using a reference tree based on full-length sequences, such as the tree from the Greengenes 16S rRNA ARB Database, and then using an algorithm such as parsimony insertion to add the short sequence reads to this reference tree. These procedures are necessarily approximate, and may lead to errors in phylogenetic reconstruction that could affect later conclusions about which communities are more similar or different. One substantial concern is that because different regions of the rRNA sequence differ in variability, conclusions drawn about the similarities between communities from different studies might be affected more by the region of the 16S rRNA that was chosen for sequencing than by the underlying biological reality.

The increase in number of sequences per run from parallel high-throughput sequencing technologies such as the Roche 454 GS FLX™ (5×10$^5$) to Illumina GAIIx™ (1×10$^8$) is on the order of 1,000-fold and greater than the increase in the number of sequences per run from Sanger (1×10$^3$ through 1×10$^4$) to 454™. The transition from Sanger sequencing to 454™ sequencing has opened new frontiers in microbial community analysis by making it possible to collect hundreds of thousands of sequences spanning hundreds of samples. A transition to the Illumina™ platform allows for more extensive sequencing than has previously been feasible, with the possibility of detecting even OTUs that are very rare. By using a variant of the barcoding strategy used for 454™ with the Illumina™ platform, thousands of samples could be analyzed in a single run, with each of the samples analyzed in unprecedented depth.

A few sequencing runs using 454™/Roche's pyrosequencing platform can generate sufficient coverage for assembling entire microbial genomes, for the discovery, identification and quantitation of small RNAs, and for the detection of rare variations in cancers, among many other applications. However, as the analytical technology becomes more advanced, the coverage provided by this system becomes unnecessary for phylogenetic classification. For analysis of multiple libraries, the 454/Roche™ pyrosequencers can accommodate a maximum of only 16 independent samples, which have to be physically separated using manifolds on the sequencing medium, drastically limiting is utility in the effort to elucidate the diverse microbial communities in each sample. Relatively speaking, the Illumina™ platforms are experiencing the most growth. However, with the constant improvements in sequencing systems, the different platforms that will be used will change over time. Generally, the method describe herein will be used with any available high-throughput sequencing platform currently available or will be available in the future. For example, the method described herein will be applied to a sequencing method wherein the genetic material will be sequenced without barcoding by simply placing the DNA or RNA directly into a sequencing machine.

In general, high-throughput sequencing technology allows for the characterization of microbial communities orders of magnitude faster and more cheaply than has previously been possible. For example, a typical Illumina MiSeq™ run can produce as many as 50 million, short paired end reads in the v3 chemistry (~300 bp long; 1.5× $10^{10}$ bp of data) in 65 hours compared to Sanger sequencing which may take a day or more to produce only 96 reads of 800 bp in length (~7.7×10 bp of data). In addition, the ability to barcode amplicons from individual samples means that hundreds of samples can be sequenced in parallel, further reducing costs and increasing the number of samples that can be analyzed. Though high-throughput sequencing reads tend to be short compared to those produced by the Sanger method, the sequencing effort is best focused on gathering more short sequences (less than 150 base pairs or less than 100 base pairs) rather than fewer longer ones as much of the diversity of microbial communities lies within the "rare biosphere," also known as the "long tail," that traditional culturing and sequencing technologies are slow to detect due to the limited amount of data generated from these techniques.

In statistics, a power law is a functional relationship between two quantities, where one quantity varies as a power of another. Power law distributions or functions characterize an important number of behaviors from nature and human endeavor. The observation of such a distribution often points to specific kinds of mechanisms, and can often indicate a deep connection with other, seemingly unrelated systems. An example of a power law graph is shown in FIG. 12.

Figure 12:
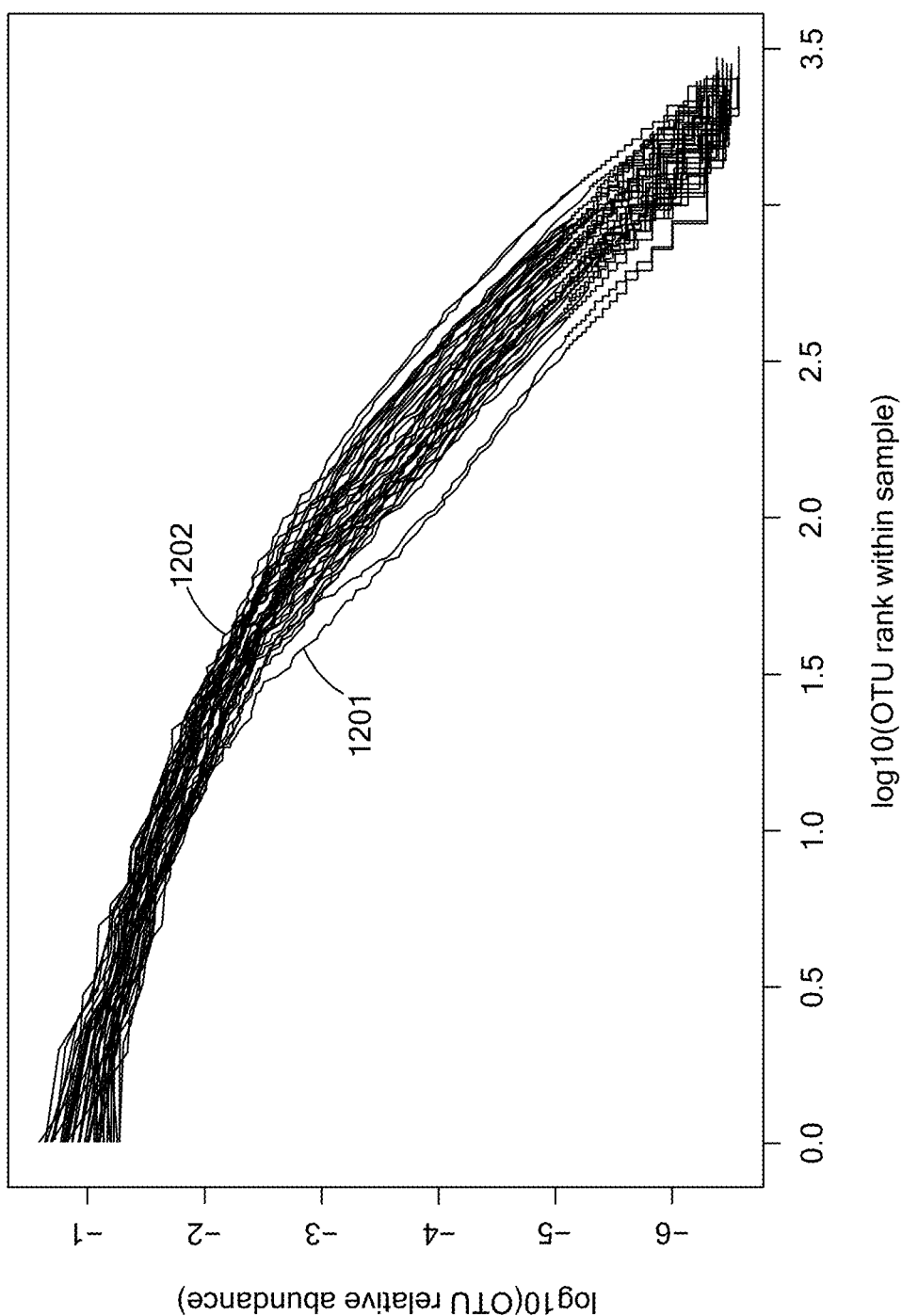
FIG. 12 is an illustration of a power law distribution in accordance with an embodiment of the present inventions.

FIG. 12 is a graph of a power law distribution. Each line, e.g., 1201, 1202, represents one of 134 human gut microbiome samples from healthy adults living in the USA included in a global survey of gut microbial diversity. To avoid undersampling of the rare microbiome, samples were sequenced at very high depth, ranging from 305,631 to 3,486,888 sequences per sample (mean±s.d.=2,018,984±543,962.2). The x- and y-axes are log scale (i.e., it is a log-log plot), where the y value represents the abundance of an OTU, and the x is the "rank" of that OTU from most abundant to least abundant. The fact that this relationship is linear in a log-log plot defines it as embodying a power law distribution. This means that the most abundant OTU is 10 times more abundant than the tenth most abundant OTU.

In the power law graph example, a long tail of some distributions of numbers is the portion of the distribution having a large number of occurrences far from the "head" or central part of the distribution. The distribution could involve many factors including but not limited to popularities, random numbers of occurrences of events with various probabilities, etc. A probability distribution is said to have a long tail, if a larger share of population rests within its tail than would under a normal distribution. A long-tail distribution will arise with the inclusion of many values unusually far from the mean. A long-tailed distribution is a particular type of heavy-tailed distribution.

Microorganisms of extremely low abundance have been designated the "rare biosphere" or "long tail," which the ecological significance of rare microorganisms is just beginning to be understood. One hypothesis is that rare members represent a dormant seed bank. Members of this seed bank may become active at random or in direct response to changes in the environment, for instance, to initiate community recovery after disturbance. This hypothesis is supported by a recent investigation of marine bacterioplankton responses to organic carbon additions, wherein rare members increased in abundance from less than 10 sequences to as many as thousands after carbon amendment. Similarly, a study in the Western English Channel showed that community members in low abundance were persistent over time, and that, in a few cases, populations of rare members occasionally bloomed. However, there also are situations in which rare members are hypothesized to be less important for the community, such as when populations are becoming extinct or are between favorable environments. Because members of the rare biosphere may provide novel products and processes, bioprospecting for these organisms has been made a priority.

The length of the read of a sequence describes the number of nucleotides in a row that the sequencer is able to obtain in one read. This length can determine the type of OTU obtained (e.g., family, genus or species). For example, a read length of approximately 300 base pairs will probably provide family information but not a species determination. Depth of coverage in DNA sequencing refers to the number of times a nucleotide is read during the sequencing process. On a genome basis, it means that, on average, each base has been sequenced a certain number of times (10×, 20× . . . ). For a specific nucleotide, it represents the number of sequences that added information about that nucleotide. Coverage is the average number of reads representing a given nucleotide in the reconstructed sequence. Depth can be calculated from the length of the original genome (G), the number of reads (N), and the average read length (L) as N×L/G. For example, a hypothetical genome with 2,000 base pairs reconstructed from 8 reads with an average length of 500 nucleotides will have 2× redundancy. This parameter also enables estimation of other quantities, such as the percentage of the genome covered by reads (coverage). Sometimes a distinction is made between sequence coverage and physical coverage. Sequence coverage is the average number of times a base is read. Physical coverage is the average number of times a base is read or spanned by mate paired reads.

Figure 5:
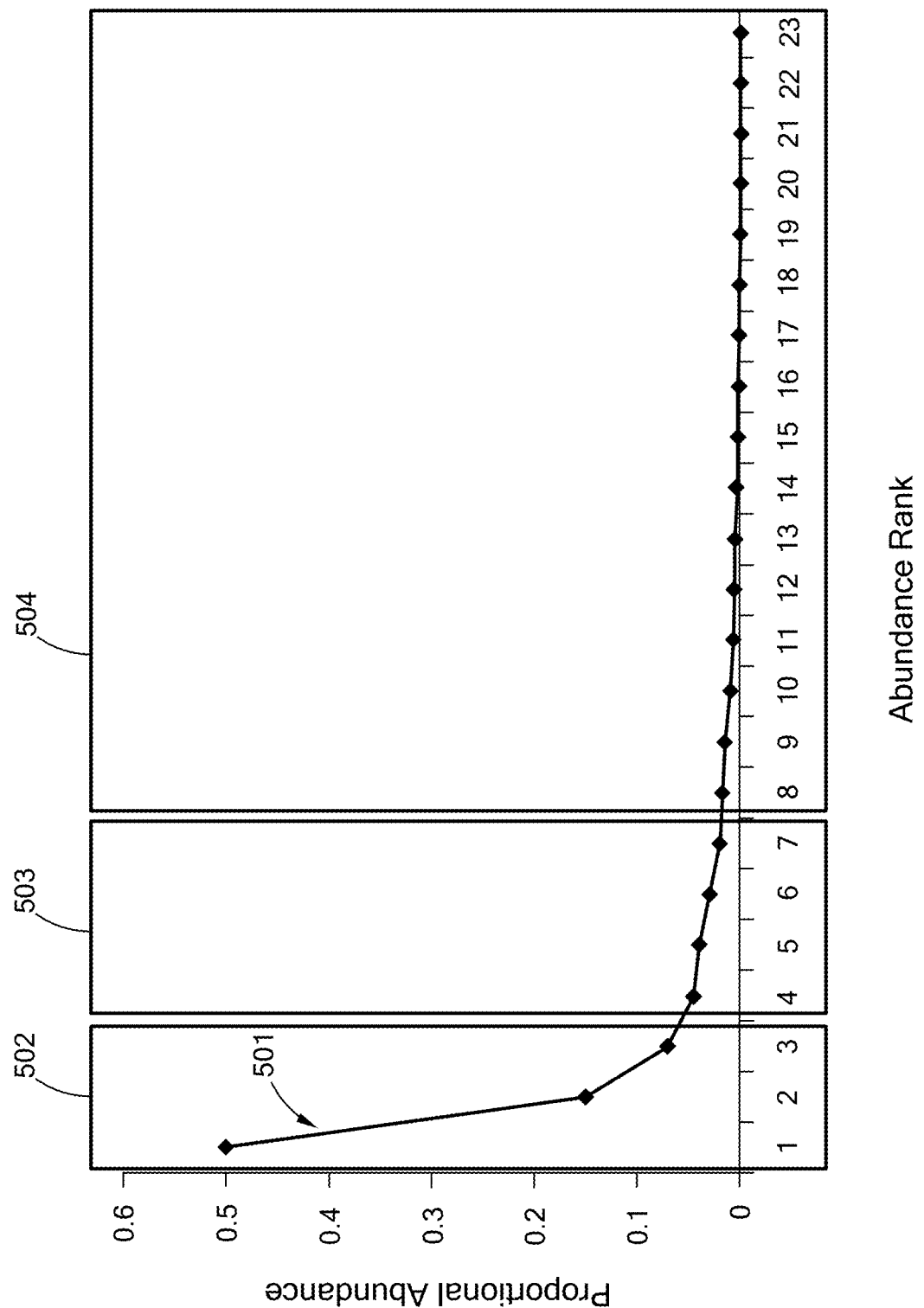
FIG. 5 is an illustration of an embodiment of a power law graph in accordance with the present inventions.

The line 501 plotted in the graph of FIG. 5 shows the ranked abundance of the OTUs on the x-axis with the most abundant species near the origin of the plot. The y-axis is the relative abundance of the OTU. The rare biosphere is the part of the line which has low values on the y-axis. For instance, OTU 10 is the $10^{th}$ most abundant organism but represents less than 0.1% of the total OTUs present in the sample, while OTU 1 represents 50% of the OTUs in the same sample. Organisms of lower abundance rank can be detected if more sequence reads are collected. For example, the most abundant OTUs that are in box 502 are verified by a relatively low read depth. The moderately abundant OTUs that are in box 503 are verified by an increasing read depth. The long tail, which signifies the rare members of the community, is in box 504. To verify that these sequences are present, a higher read depth (i.e. more sequences) must be obtained. Analyzing the rare biosphere is attainable because sequencing depth provided by high-throughput sequencing allows for the detection of microbes that would otherwise be detected only occasionally by chance with traditional techniques.

With existing technology, the realistic time requirement for nucleic acid extraction, library preparation and sequencing is approximately a few days for a few samples. Analysis of the sequencing data will require an additional few hours depending on the system. However, with minimizing the necessary read length, for example, to less than 150 base pairs or less than 100 base pairs, and maximizing the read depth in order to capture the organisms in the long tail of the power law graph, this time can be variable. Another variable factor is the advances in technology for high-throughput sequencing. Thus high-throughput sequencing will allow for the analysis of the more rare members (low abundance organisms) of any environment which may play critical role in, for example, oil and gas production, petroleum pipeline maintenance, food production, agriculture and other industries where microbes are present within a time-frame feasible for industrial settings. For example, the time from sampling to analysis of the sequencing information will be reduced to a few days or a few hours, and in another example, as quickly as under an hour, or under a few minutes, or preferably under a minute.

Pyrosequencing

One type of high-throughput sequencing is known as pyrosequencing. Pyrosequencing, based on the "sequencing by synthesis" principle, is a method of DNA sequencing widely used in microbial sequencing studies. Pyrosequencing involves taking a single strand of the DNA to be sequenced and then synthesizing its complementary strand enzymatically. The pyrosequencing method is based on observing the activity of DNA polymerase, which is a DNA synthesizing enzyme, with another chemiluminescent enzyme. The single stranded DNA template is hybridized to a sequencing primer and incubated with the enzymes DNA polymerase, ATP sulfurylase, luciferase and apyrase, and with the substrates adenosine 5' phosphosulfate (APS) and luciferin. Synthesis of the complementary strand along the template DNA allows for sequencing of a single strand of DNA, one base pair at a time, by the detection of which base was actually added at each step.

The template DNA is immobile, and solutions of A, C, G, and T nucleotides are sequentially added and removed from the reaction. The templates for pyrosequencing can be made both by solid phase template preparation (streptavidin-coated magnetic beads) and enzymatic template preparation (apyrase+exonuclease). Specifically, the addition of one of the four deoxynucleoside triphosphates (dNTPs) (dATPαS, which is not a substrate for a luciferase, is added instead of dATP) initiates the next step. DNA polymerase incorporates the correct, complementary dNTPs onto the template. This base incorporation releases pyrophosphate (PPi) stoichiometrically. Then, ATP sulfurylase quantitatively converts PPi to ATP in the presence of adenosine 5' phosphosulfate. This ATP acts to catalyze the luciferase-mediated conversion of luciferin to oxyluciferin that generates visible light in amounts that are proportional to the amount of ATP. Light is produced only when the nucleotide solution complements the particular unpaired base of the template. The light output in the luciferase-catalyzed reaction is detected by a camera and analyzed in a program. The sequence of solutions which produce chemiluminescent signals allows the sequence determination of the template. Unincorporated nucleotides and ATP are degraded by the apyrase, and the reaction can restart with another nucleotide.

Illumina's™ Sequencing by Synthesis (SBS)

Illumina's™ sequencing by synthesis (SBS) technology with TruSeq technology supports massively parallel sequencing using a proprietary reversible terminator-based method that enables detection of single bases as they are incorporated into growing DNA strands.

A fluorescently labeled terminator is imaged as each dNTP is added and then cleaved to allow incorporation of the next base. Since all four reversible terminator-bound dNTPs are present during each sequencing cycle, natural competition minimizes incorporation bias. The end result is true base-by-base. Although this is similar to pyrosequencing, the differences between the platforms are noteworthy. The method described herein can be applied to any high-throughput sequencing technology, past, present or future. Pyrosequencing and SBS are merely examples and do not limit the application of the method in terms of sequencing.

Analysis of Sequencing Data

Generally, as the expense of sequencing decreases, the methods for comparing different communities based on the sequences they contain become increasingly important, and are often the bottleneck in obtaining insight from the data. Sequence data can be analyzed in a manner in which sequences are identified and labeled as being from a specific sample using the unique barcode introduced during library preparation, if barcodes are used, or sample identifiers will be associated with each run directly if barcodes are not used. Once sequences have been identified as belonging to a specific sample, the relationship between each pair of samples will be determined based on the distance between the collection of microbes present in each sample. In particular, techniques that allow for the comparison of many microbial samples in terms of the phylogeny of the microbes that live in them ("phylogenetic techniques") are often necessary. Such methods are particularly valuable as the gradients that affect microbial distribution are analyzed, and where there is a need to characterize many communities in an efficient and cost-effective fashion. Gradients of interest include different physical or chemical gradients in natural environments, such as temperature or nutrient gradients in certain industrial settings.

When comparing microbial communities, researchers often begin by determining whether groups of similar community types are significantly different. However, to gain a broad understanding of how and why communities differ, it is essential to move beyond pairwise significance tests. For example, determining whether differences between communities stem primarily from particular lineages of the phylogenetic tree, or whether there are environmental factors (such as temperature, salinity, or acidity) that group multiple communities together is pivotal to an analysis. The analysis systems described herein are merely examples and are not limiting. Any methods which will distill massive data sets from raw sequences to human-interpretable formats, for example, 2-D or 3-D ordination plots, supervised learning for predictive modeling, or more traditional statistical significance testing, allowing for pattern elucidation and recognition, will be used.

QIIME

After DNA sequence data is obtained the bioinformatics stages begin. This includes barcode decoding, sequence quality control, "upstream" analysis steps (including clustering of closely related sequences and phylogenetic tree construction), and "downstream" diversity analyses, visualization, and statistics. All of these steps are currently facilitated by the Quantitative Insights Into Microbial Ecology (QIIME, www.qiime.org) open source software package, which is the most widely used software for the analysis of microbial community data generated on high-throughput sequencing platforms. QIIME was initially designed to support the analysis of marker gene sequence data, but is also generally applicable to "comparative-omics" data (including but not limited to metabolomics, metatranscriptomics, and comparative human genomics).

QIIME is designed to take users from raw sequencing data (for example, as generated on the Illumina™ and 454™ platforms) though the processing steps mentioned above, leading to quality statistics and visualizations used for interpretation of the data. Because QIIME scales to billions of sequences and runs on systems ranging from laptops to high-performance computer clusters, it will continue to keep pace with advances in sequencing technologies to facilitate characterization of microbial community patterns ranging from normal variations to pathological disturbances in many human, animal and environmental ecosystems.

For microbiome data analysis, the following steps will be taken. Unless otherwise noted, the steps will be performed with QIIME. However, other such systems may be used and the scope of protection afforded to the present inventions is not in anyway limited to, or dependent upon, the use of QIIME.

Compiling the Sample Metadata Mapping File

The first step in the bioinformatics stage of a microbial community analysis study is to consolidate the sample metadata in a spreadsheet. The sample metadata is all per-sample information, including technical information such as the barcode assigned to each sample, and "environmental" metadata. This environmental metadata will differ depending on the types of samples that are being analyzed. If, for example, the study is of microbial communities in soils, the pH and latitude where the soil was collected will be environment metadata categories. Alternatively, if the samples are of the human microbiome, environmental metadata may include subject identifiers and collection times. This spreadsheet will be referred to as the sample metadata mapping file in the following sections. An example sample metadata mapping file is provided as Table 1.

TABLE 1

Sample Metadata Mapping File

| Sample ID | Barcode Sequence | LinkerPrimerSequence | TEXTURE | DEPTH | TOT_ORG | SPECIFIC_LOCATION |
|---|---|---|---|---|---|---|
| IT2 | ACGTGCCGTAGA | CATGCTGCCTCCCGTAGGAGT | loamy sand | 0-0.05 | 39.1 | Itasca Lake State Park, MN USA |
| HI3 | ACGCTATCTGGA | CATGCTGCCTCCCGTAGGAGT | loamy sand | 0-0.05 | 182.4 | Kohala Peninsula, HI USA |
| MD2 | ACTCGATTCGAT | CATGCTGCCTCCCGTAGGAGT | sandy loam | 0-0.05 | 4.2 | Mojavo Desert, CA USA |
| CA1 | ACACGAGCCACA | CATGCTGCCTCCCGTAGGAGT | silt loam | 0-0.05 | 16.7 | Cedar Mtn, AZ, USA |
| PE3 | AGACTGCGTACT | CATGCTGCCTCCCGTAGGAGT | clay loam | 0-0.05 | 93.6 | Manu National Park, Peru |
| CO1 | ACATGATCGTTC | CATGCTGCCTCCCGTAGGAGT | sand | 0-0.05 | 15.9 | Fort Collins, CO USA |
| DF3 | ACCGCAGAGTCA | CATGCTGCCTCCCGTAGGAGT | loamy sand | 0-0.05 | 17 | Duke Forest, NC USA |
| PE1 | ACTTGTAGCAGC | CATGCTGCCTCCCGTAGGAGT | sandy loam | 0-0.05 | 134.2 | Manu National Park, Peru |
| SP2 | AGCGCTGATGTG | CATGCTGCCTCCCGTAGGAGT | loamy sand | 0-0.05 | 81 | Sequola National Park, CA USA |
| CO3 | ACATTCAGCGCA | CATGCTGCCTCCCGTAGGAGT | sandy loam | 0-0.05 | 8.2 | Shortgrass Steppe LTFR, CO USA |
| SA2 | AGATCGGCTCGA | CATGCTGCCTCCCGTAGGAGT | sand | 0-0.05 | 25 | Sunset Crater, AZ USA |
| CM1 | ACATCACTTAGC | CATGCTGCCTCCCGTAGGAGT | silty clay | 0-0.05 | 29.9 | Clymer Meadow Preserve, TX USA |
| LQ2 | ACTCACGGTATG | CATGCTGCCTCCCGTAGGAGT | silty clay loam | 0-0.05 | 41.1 | Luquillo LTER, Puerto Rico |
| SR2 | AGCTATCCACGA | CATGCTGCCTCCCGTAGGAGT | sandy loam | 0-0.05 | 14.6 | Sedgwig Reserve, CA USA |
| CH1 | ACCACATACATC | CATGCTGCCTCCCGTAGGAGT | loam | 0-0.05 | 28.3 | Coffey Ranch, TX USA |
| VC1 | AGGTGTGATCGC | CATGCTGCCTCCCGTAGGAGT | sandy loam | 0-0.05 | 56.7 | Valles Caldera, NM USA |

TABLE 1-continued

Sample Metadata Mapping File

| Sample ID | Barcode Sequence | LinkerPrimerSequence | TEXTURE | DEPTH | TOT_ORG | SPECIFIC_LOCATION |
|---|---|---|---|---|---|---|
| IE2 | ACGTCTGTAGCA | CATGCTGCCTCCCGTAGGAGT | sandy loam | 0-0.05 | 40.7 | Institute for Ecosystem Studies, N |
| RT2 | AGAGTCCTGAGC | CATGCTGCCTCCCGTAGGAGT | silty clay loam | 0-0.05 | 37.5 | USDA Grassland Research Center, |
| BB1 | AAGAGATGTCGA | CATGCTGCCTCCCGTAGGAGT | sandy loam | 0-0.05 | 12.84 | Bear Brook, ME |
| CC1 | ACACTAGATCCG | CATGCTGCCTCCCGTAGGAGT | sand | 0-0.05 | 19.1 | Cedar Creek LTER, MN USA |
| TL2 | AGGACGCACTGT | CATGCTGCCTCCCGTAGGAGT | silt loams | 0-0.05 | 158.3 | Toollk Lake LTER, AK USA |
| PE6 | AGAGAGCAAGTG | CATGCTGCCTCCCGTAGGAGT | clay | 0-0.05 | 33.4 | Manu National Park, Peru |
| HI1 | ACGCGATACTGG | CATGCTGCCTCCCGTAGGAGT | loam | 0-0.05 | 11.4 | Kohala Peninsula, HI USA |
| PE7 | AGAGCAAGAGCA | CATGCTGCCTCCCGTAGGAGT | silty clay | 0-0.05 | 63.8 | Manu National Park, Peru |
| BF1 | AATCAGTCTCGT | CATGCTGCCTCCCGTAGGAGT | loam | 0-0.05 | 64.4 | Bousson Forest, PA, USA |
| TL1 | AGCTTGACAGCT | CATGCTGCCTCCCGTAGGAGT | loam | 0-0.05 | 70.2 | Toollk Lake LTER, AK USA |
| KP1 | ACTACAGCCTAT | CATGCTGCCTCCCGTAGGAGT | silt loam | 0-0.05 | 61.2 | Konza Prairie LTER, KS USA |
| CL3 | ACAGTGCTTCAT | CATGCTGCCTCCCGTAGGAGT | loamy sand | 0-0.05 | 12.1 | Calhoun Experimental Forest, SC |

(SEQ ID NOS: 10-65, respectively)

Barcode Decoding and Quality Control

Next, in a combined analysis step, sequence barcodes will be read to identify the source sample of each sequence, poor quality regions of sequence reads will be trimmed, and poor quality reads will be discarded. These steps will be combined for computational efficiency. The features included in quality filtering include whether the barcode will unambiguously be mapped to a sample barcode, per-base quality scores, and the number of ambiguous (N) base calls. The default settings for all quality control parameters in QIIME will be determined by benchmarking combinations of these parameters on artificial (i.e., "mock") community data, where microbial communities were created in the lab from known concentrations of cultured microbes, and the composition of the communities is thus known in advance.

Sequence Clustering or "OTU Picking"

After mapping sequence reads to samples and performing quality control, sequences will be clustered into OTUs (Operational Taxonomic Units). This is typically the most computationally expensive step in microbiome data analysis, and will be performed to reduce the computational complexity at subsequent steps. The assumption made at this stage is that organisms that are closely related, as determined by the similarity of their marker gene sequences, are functionally similar. Highly similar sequences (e.g., those that are greater than 97% identical to one another) will be clustered, the count of sequences that are contained in each cluster will be retained, and then a single representative sequence from that cluster for use in downstream analysis steps such as taxonomic assignment and phylogenetic tree construction will be chosen. This process of clustering sequences is referred to as OTU picking, where the OTUs (i.e., the clusters of sequences) are considered to represent taxonomic units such as species.

There are three high-level strategies for OTU picking, each of which is implemented in QIIME. In a de novo OTU picking process, reads will be clustered against one another without any external reference sequence collection. pick_de_novo_otus.py is the primary interface for de novo OTU picking in QIIME, and includes taxonomy assignment, sequence alignment, and tree-building steps. A benefit of de novo OTU picking is that all reads are clustered. A drawback is that there is no existing support for running this in parallel, so it can be too slow to apply to large datasets (e.g., more than 10 million reads). De novo OTU picking must be used if there is no reference sequence collection to cluster against, for example because an infrequently used marker gene is being used. De novo OTU picking cannot be used if the comparison is between non-overlapping amplicons, such as the V2 and the V4 regions of the 16S rRNA gene or for very large data sets, like a full HiSeq™ 2000 run. Although technically, de novo OTU picking can be used for very large data sets, the program would take too long to run to be practical.

In a closed-reference OTU picking process, reads will be clustered against a reference sequence collection and any reads that do not hit a sequence in the reference sequence collection are excluded from downstream analyses. pick_closed_reference_otus.py is the primary interface for closed-reference OTU picking in QIIME. If the user provides taxonomic assignments for sequences in the reference database, those are assigned to OTUs. Closed-reference OTU picking must be used if non-overlapping amplicons, such as the V2 and the V4 regions of the 16S rRNA, will be compared to each other. The reference sequences must span both of the regions being sequenced. Closed-reference OTU picking cannot be used if there is no reference sequence collection to cluster against, for example because an infrequently used marker gene is being used. A benefit of closed-reference OTU picking is speed in that the picking is fully parallelizable, and therefore useful for extremely large data sets. Another benefit is that because all OTUs are already defined in the reference sequence collection, a trusted tree and taxonomy for those OTUs may already exist. There is the option of using those, or building a tree and taxonomy from the sequence data. A drawback to reference-based OTU picking is that there is an inability to detect novel diversity with respect to the reference sequence collection. Because reads that do not hit the reference sequence collection are discarded, the analyses only focus on the diversity that is already known. Also, depending on how well-characterized the environment is, a small fraction of the reads (e.g., discarding 1-10% of the reads is common for 16S-based human microbiome studies, where databases like Greengenes cover most of the organisms that are typically present) or a large fraction of your reads (e.g., discarding 50-80% of the reads has been observed for "unusual" environments like the Guerrero Negro microbial mats) may be discarded.

In an open-reference OTU picking process, reads will be clustered against a reference sequence collection and any reads which do not hit the reference sequence collection are subsequently clustered de novo. pick_open_reference_otus.py is the primary interface for open-reference OTU picking in QIIME, and includes taxonomy assignment, sequence alignment, and tree-building steps. Open-reference OTU picking with pick_open_reference_otus.py is the preferred strategy for OTU picking. Open-reference OTU picking cannot be used for comparing non-overlapping amplicons, such as the V2 and the V4 regions of the 16S rRNA, or when there is no reference sequence collection to cluster against, for example because an infrequently used marker gene is being used. A benefit of open-reference OTU picking is that all reads are clustered. Another benefit is speed. Open-reference OTU picking is partially run in parallel. In particular, the subsampled open reference OTU picking process implemented in pick_open_reference_otus.py is much faster than pick_de_novo_otus.py as some strategies are applied to run several pieces of the workflow in parallel. However, a drawback of open-reference OTU picking is also speed. Some steps of this workflow run serially. For data sets with a lot of novel diversity with respect to the reference sequence collection, this can still take days to run.

Generally, uclust is the preferred method for performing OTU picking. QIIME's uclust-based open reference OTU picking protocol will be used when circumstances allow (i.e., when none of the cases above, where open reference OTU picking is not possible, apply).

The OTU-picking protocol described above is used for processing taxonomic marker gene sequences such as those from the 16S rRNA, ITS and LSU genes as well as other marker genes. In that case, the sequences themselves are not used to identify biological functions performed by members of the microbial community; they are instead used to identify which kinds of organisms are present. In the case of shotgun metagenomic sequencing, the data obtained are random fragments of all genomic DNA present in a given microbiome. These can be compared to reference genomes to identify the types of organisms present in a manner similar to marker gene sequences, but they may also be used to infer biological functions encoded by the genomes of microbes in the community. Typically this is done by comparing them to reference genomes and/or individual genes or genetic fragments that have been annotated for functional content. In the case of shotgun metatranscriptomic sequencing, the data obtained are similar to that for shotgun metatranscroptomic sequencing except that the RNA rather than the DNA is used, and physical or chemical steps to deplete particular classes of sequence such as eukaryotic messenger RNA or ribosomal RNA are often used prior to library construction for sequencing. In the case of shotgun metaproteomics, protein fragments are obtained and matched to reference databases. In the case of shotgun metabolomics, metabolites are obtained by biophysical methods including nuclear magnetic resonance or mass spectrometry. In all of these cases, some type of coarse-graining of the original data equivalent to OTU picking to identify biologically relevant features is employed, and a biological observation matrix as described above relating either the raw or coarse-grained observations to samples is obtained. The steps downstream from the Biological Observation Matrix, including the construction of distance matrices, taxon or functional tables, and industry-specific, actionable models from such data, are conceptually equivalent for each of these datatypes and are within the scope of the present Invention.

Choosing OTU representative sequences, assigning taxonomy, aligning sequences, and constructing phylogenetic trees Next, the centroid sequence in each OTU will be selected as the representative sequence for that OTU. The centroid sequence will be chosen so that all sequences are within the similarity threshold to their representative sequence, and the centroid sequences are specifically chosen to be the most abundant sequence in each OTU.

The OTU representative sequences will next be aligned using an alignment algorithm such as the PyNAST software package. PyNAST is a reference-based alignment approach, and is chosen because it achieves similar quality alignments to non-reference-based alignment approaches (e.g., muscle), where quality is defined as the effect of the alignment algorithm choice on the results of phylogenetic diversity analyses, but is easily run in parallel, which is not the case for non-reference-based alignment algorithms.

Once a PyNAST alignment is obtained, positions that mostly contain gaps, or too high or too low variability, will be stripped to create a position-filtered alignment. This position-filtered alignment will be used to construct a phylogenetic tree using FastTree. This tree relates the OTUs to one another, will be used in phylogenetic diversity calculations (discussed below), and is referred to below as the OTU phylogenetic tree.

In addition to being aligned, all OTU representative sequences will have taxonomy assigned to them. This can be performed using a variety of techniques, though our currently preferred approach is the uclust-based consensus taxonomy assigner implemented in QIIME. Here, all representative sequences (the "query" sequences) are queried against a reference database (e.g., Greengenes, which contains near-full length 16S rRNA gene sequences with human-curated taxonomic assignments; UNITE database for ITS; SILVA for 18S rRNA) with uclust. The taxonomy assignments of the three best database hits for each query sequences are then compared, and a consensus of those assignments is assigned to the query sequence.

Constructing a Biological Observation Matrix (BIOM) Table

The last of the "upstream" processing steps is to create a Biological Observation Matrix (BIOM) table, which contains counts of OTUs on a per-sample basis and the taxonomic assignment for each OTU. This table, which will be referred to as the BIOM table, the OTU phylogenetic tree constructed above, and the sample metadata mapping file will be the data required for computing phylogenetic diversity metrics in the next steps, and for doing visual and statistical analysis based on these diversity metrics. Although the BIOM is a specific file format for the table with OTU counts on a per-table basis, other file formats are also possible as well.

Analysis of Microbial Communities

Once a BIOM table, an OTU phylogenetic tree, and a sample metadata mapping file (n-dimensional plot) are compiled, the microbial communities present in each sample will be analyzed and compared. These analyses include, but are not limited to, summarizing the taxonomic composition of the samples, understanding the "richness" and "evenness" of samples (defined below), understanding the relative similarity of communities, and identifying organisms or groups of organisms that are significantly different across community types. The different types of analysis on soil microbial community data will be illustrated in Example 11.

Taxonomic Composition of Samples

Figure 11:
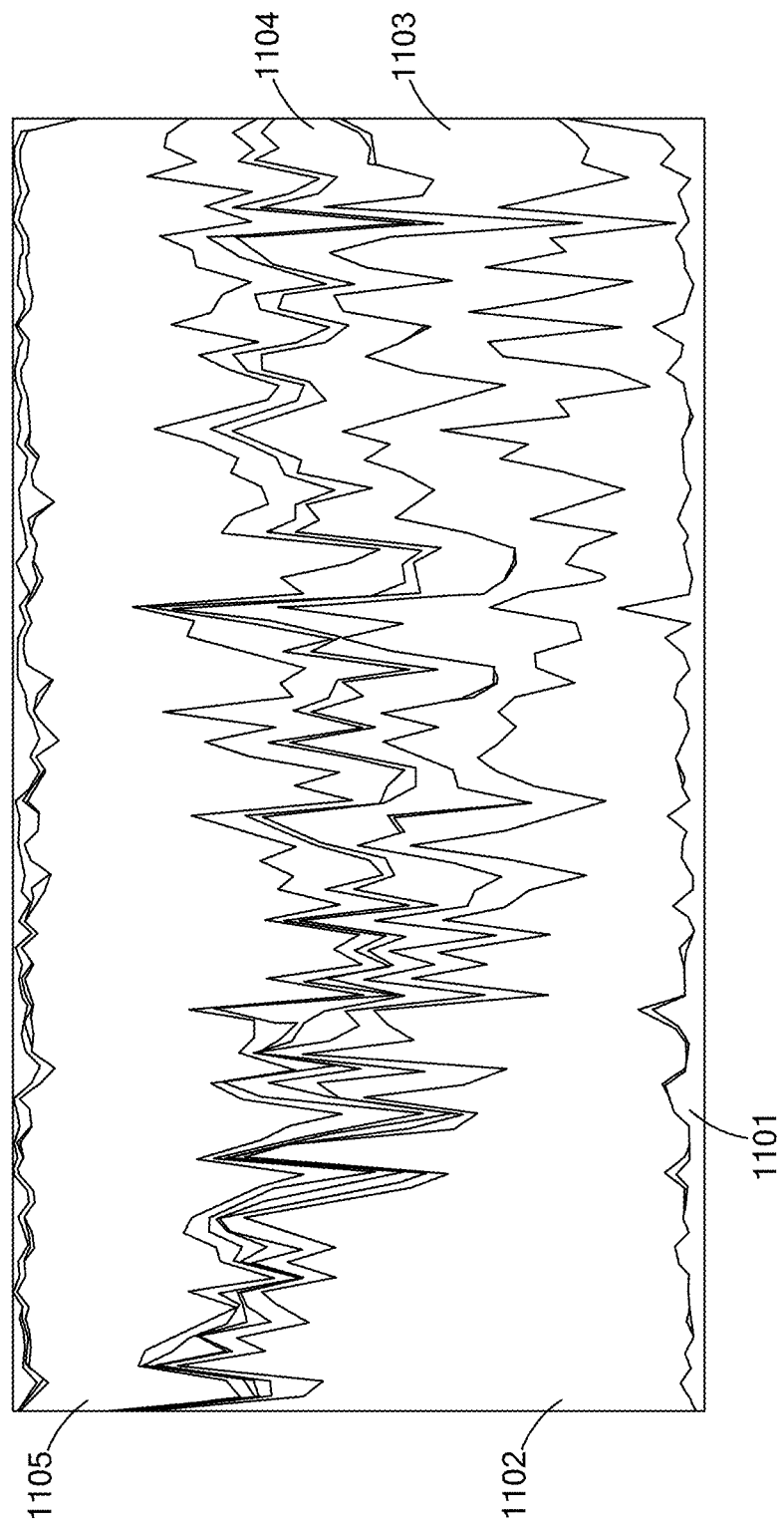
FIG. 11 is an illustration of an embodiment of microbiome composition presented in accordance with an embodiment of the present inventions.

The taxonomic composition of samples is often something that researchers are most immediately interested in. This can be studied at various taxonomic levels (e.g., phylum, class, species) by collapsing OTUs in the BIOM table based on their taxonomic assignments. The abundance of each taxon on a per-sample basis is then typically presented in bar charts, area charts or pie charts, though this list is not comprehensive. FIG. 11 contains an area chart illustrating the phylum level composition of 88 soils spanning a pH gradient.

Figure 8:
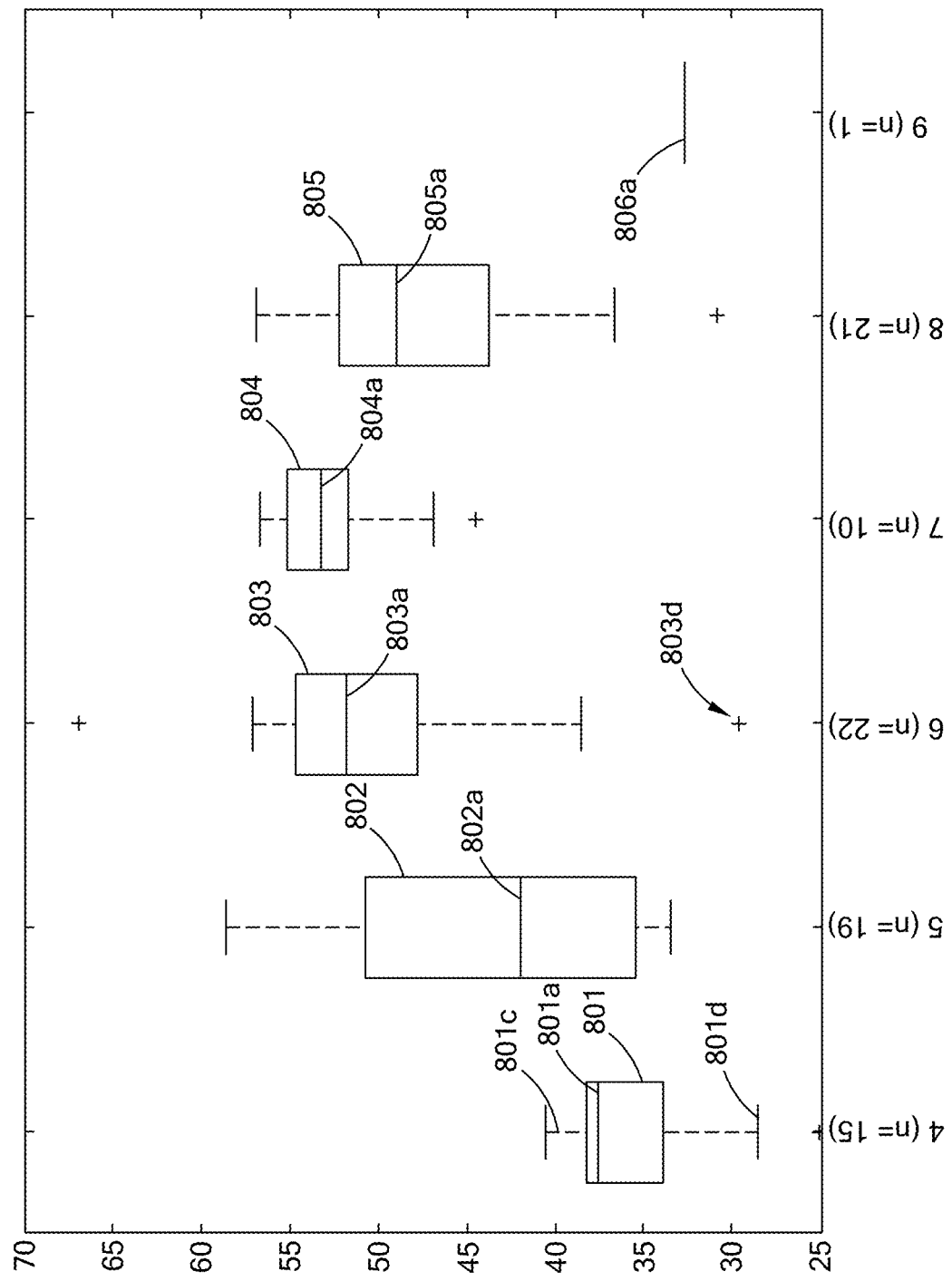
FIG. 8 is a chart of an embodiment of the association of environmental parameters with microbial composition in accordance with the present inventions.

Within-Sample Diversity (Richness and Evenness):

Alpha diversity refers to diversity of single samples (i.e., within-sample diversity), including features such as taxonomic richness and evenness. The species richness is a measure of the number of different species of microbes in a given sample. Species evenness refers to how close in numbers the abundance of each species in an environment is. Measures of alpha diversity (or, within-sample diversity) have a long history in ecology. Alpha diversity scores have been shown to differ in different types of communities, for example, from different human body habitats. For instance, skin-surface bacterial communities have been found to be significantly more rich (i.e., containing more species) in females than in males, and at dry sites rather than sebaceous sites, and the gut microbiome of lean individuals have been found to be significantly more rich than those of obese individuals. FIG. 8 illustrate one way of viewing alpha diversity in the context of environmental metadata. Here we show that the degree of phylogenetic diversity in a sample (a phylogeny-aware measure of richness) changes with soil pH, for 88 soils ranging from pH around 6.5 through 9.5, with a peak in richness around neutral pH of 7. These data suggest that in some cases alpha diversity will be useful input features for building predictive models via supervised classifiers.

Between-Sample Diversity (UniFrac and Principal Coordinates Analysis)

Generally the primary question of interest when beginning a survey of new microbial community types is what environmental features are associated with differences in the composition of microbial communities? This is a question of between-sample (or "beta") diversity. Beta diversity metrics provide a measure of community dissimilarity, allowing investigators to determine the relative similarity of microbial communities. Metrics of beta diversity are pairwise, operating on two samples at a time.

The difference in overall community composition between each pair of samples can be determined using the phylogenetically-aware UniFrac distance metric, which allows researchers to address many of these broader questions about the composition of microbial communities. UniFrac calculates the fraction of branch length unique to a sample across a phylogenetic tree constructed from each pair of samples. In other words, the UniFrac metric measures the distance between communities as the percentage of branch length that leads to descendants from only one of a pair of samples represented in a single phylogenetic tree, or the fraction of evolution that is unique to one of the microbial communities. Phylogenetic techniques for comparing microbial communities, such as UniFrac, avoid some of the pitfalls associated with comparing communities at only a single level of taxonomic resolution and provide a more robust index of community distances than traditional taxon-based methods, such as the Jaccard and Sorenson indices. Unlike phylogenetic techniques, species-based methods that measure the distance between communities based solely on the number of shared taxa do not consider the amount of evolutionary divergence between taxa, which can vary widely in diverse microbial populations. Among the first applications of phylogenetic information to comparisons of microbial communities were the Phylogenetic (P)-test and the $F_{ST}$ test. Pairwise significance tests are limited because they cannot be used to relate many samples simultaneously. Although phylogenetically-aware techniques such as UniFrac offer significant benefits, techniques lacking phylogenetic awareness can also be implemented with success: after an alternative distance metric (e.g. Bray-Curtis, Jensen-Shannon divergence) has been applied, the resulting inter-sample distance matrix is processed in the same way as a UniFrac distance matrix as described below.

QIIME implements the UniFrac metric and uses multivariate statistical techniques to determine whether groups of microbial communities are significantly different. When studying a set of n microbial communities, the UniFrac distances between all pairs of communities are computed to derive a distance matrix (using UniFrac or other distances) for all samples. This will be an n×n matrix, which is symmetric (because the distance between sample A and sample B is always equal to the distance between sample B and sample A) and will have zeros on the diagonal (because the distance between any sample and itself is always zero). For any reasonably larger value of n (e.g., n>5) it becomes difficult to interpret patterns of beta diversity from a distance matrix directly (FIG. 6). FIG. 6 shows matrix formed from unweighted UniFrac distances between the first 12 of the 88 soil samples included in the analysis in Example 10. As the number of samples increases beyond just a few (e.g., five) samples, it becomes very difficult to identify meaningful patterns from distance matrices alone.

Ordination techniques, such as principal coordinates analysis (PCoA) and non-metric multidimensional scaling (NMDS), together with approximations to these techniques that reduce computational cost or improve parallelism, will be used to summarize these patterns in two or three dimensional scatter plots. The patterns can also be represented in two dimensions using, for example, line graph, bar graphs, pie charts, Venn diagrams, etc. This is a non-exhaustive list. The patterns can also be represented in three dimensions using, for example, wire frame, ball and stick models, 3-D monitors, etc. This list is also non-exhaustive and does not limit the 2-D or 3-D forms by which the data can be represented.

PCoA is a multivariate statistical technique for finding the most important orthogonal axes along which samples vary. Distances are converted into points in a space with a number of dimensions one less than the number of samples. The principal components, in descending order, describe how much of the variation (technically, the inertia) each of the axes in this new space explains. The first principal component separates the data as much as possible; the second principal component provides the next most separation along an orthogonal axis, and so forth. QIIME returns information on all principal component axes in a data table. It also allows easy visualization of that data in interactive scatter plots that allow users to choose which principal components to display. The points (each representing a single sample) are typically marked with colored symbols, (grey scale symbols are used for the purposes of the patent figures) and users can interactively change the colors of the points to detect associations between sample microbial composition and sample metadata. PCoA often reveals patterns of similarity that are difficult to see in a distance matrix (see e.g., FIGS. 9 and 10), and the axes along which variation occurs can sometimes be correlated with environmental variables such as pH or temperature. Industrial variables, or control data, can include presence of oil, pressure, viscosity, etc. These control data can be filtered or removed in order to observe other control data factors to visualize possible patterns.

New ways of exploring and visualizing results and identifying meaningful patterns are increasingly important as the size and complexity of microbial datasets rapidly increase. QIIME 1.8.0 (released in December 2013) introduces several powerful tools to assist in visualizations of the results of PCoA, primarily the Emperor 3D scatter plot viewer (https://github.com/qiime/emperor). This includes (i) the ability to color large collections of samples using different user-defined subcategories (for example, coloring environmental samples according to temperature or pH), (ii) automatic scaled/unscaled views, which accentuate dimensions that explain more variance, (iii) the ability to interactively explore tens of thousands of points (and user-configurable labels) in 3D, and (iv) parallel coordinates displays that allow the dimensions that separate particular groups of environments to be readily identified.

The significance of patterns identified in PCoA can be tested with a variety of methods. The significance of the clusters identified by UniFrac can be established using Monte Carlo based t-tests, where samples are grouped into categories based on their metadata, and distributions of distances within and between categories are compared. For example, if microbial communities are being compared between soils from an oil well and soils unassociated with oil, the distribution of UniFrac distances between soils from the same group can be compared to the those between soils from different groups by computing a t-score (the actual t-score). The sample labels (oil and not oil) can then be randomly shuffled 10,000 times, and a t-score calculated for each of these randomized data sets (the randomized t-scores). If the oil soils and non-oil soils are significantly different from one another in composition, the actual t-score should higher than the vast majority of the randomized t-scores. A p-value will be computed by dividing the number of randomized t-scores that are better than the actual t-score by 9999. The Monte Carlo simulations described here will be run in parallel, and are not limited to pairs of sample categories, so they support analysis of many different sample types.

If the samples fall along a gradient that is correlated with some environmental metadata (e.g., pH, salinity), rather than clustering into discrete groups (as described above), there are alternative approaches to testing for statistical significance. For example, if pH appears to be correlated with the principal coordinate 1 (PC1) values in a PCoA plot, a Monte Carlo-based Pearson or Spearman correlation test will be performed. Here, pH and PC1 will be tested to, for example, compute a Spearman rho value. The labels of the samples will again be shuffled 10,000 times and rho computed for each randomized data set. The p-value for the pH versus PC1 correlation will then be the number of randomized rho values that are higher than the actual rho value divided by 9999.

Identifying Features that are Predictive of Environment Characteristics (i.e., Sample Metadata)

Supervised classification is a machine learning approach for developing predictive models from training data. Each training data point consists of a set of input features, for example, the relative abundance of taxa, and a qualitative dependent variable giving the correct classification of that data point. In microbiome analysis, such classifications might include soil nutrients, the presence of oil, predominant weather patterns, disease states, therapeutic results, or forensic identification. The goal of supervised classification is to derive some function from the training data that can be used to assign the correct class or category labels to novel inputs (e.g. new samples), and to learn which features, for example, taxa, discriminate between classes. Common applications of supervised learning include text classification, microarray analysis, and other bioinformatics analyses. For example, when microbiologists use the Ribosomal Database Project website to classify 16S rRNA gene sequences taxonomically, a form of supervised classification is used.

The primary goal of supervised learning is to build a model from a set of categorized data points that can predict the appropriate category membership of unlabeled future data. The category labels can be any type of important metadata, such as pressure, viscosity, pH or temperature. The ability to classify unlabeled data is useful whenever alternative methods for obtaining data labels are difficult or expensive.

This goal of building predictive models is very different from the traditional goal of fitting an explanatory model to one's data set. The concern is less with how well the model fits our particular set of training data, but rather with how well it will generalize to novel input data. Hence, there is a problem of model selection. A model that is too simple or general is undesirable because it will fail to capture subtle, but important information about the independent variables (underfitting). A model that is too complex or specific is also undesirable because it will incorporate idiosyncrasies that are specific only to the particular training data (overfitting). The expected prediction error (EPE) of the model on future data must be optimized.

When the labels for the data are easily obtained, a predictive model is unnecessary. In these cases, supervised learning will still be useful for building descriptive models of the data, especially in data sets where the number of independent variables or the complexity of their interactions diminishes the usefulness of classical univariate hypothesis testing. Examples of this type of model can be seen in the various applications of supervised classification to microarray data, in which the goal is to identify a small, but highly predictive subset of the thousands of genes profiled in an experiment for further investigation. In microbial ecology, the analogous goal is to identify a subset of predictive taxa. In these descriptive models, accurate estimation of the EPE is still important to ensure that the association of the selected taxa with the class labels is not just happenstance or spurious. This process of finding small but predictive subsets of features, called feature selection, is increasingly important as the size and dimensionality of microbial community analyses continue to grow.

A common way to estimate the EPE of a particular model is to fit the model to a subset (e.g., 90%) of the data and then test its predictive accuracy on the other 10% of the data. This can provide an idea of how well the model would perform on future data sets if the goal is to fit it to the entire current data set. To improve the estimate of the EPE, this process will be repeated ten times so that each data point is part of the held-out validation data once. This procedure, known as cross-validation, will allow for the comparison of models that use very different inner machinery or different subsets of input features. Of course if many different models are tried and one provides the lowest cross-validation error for the entire data set is selected, it is likely that the reported EPE will be too optimistic. This is similar to the problem of making multiple comparisons in statistical inference; some models are bound to fortuitously match a particular data set. Hence, whenever possible, an entirely separate test set will be held out for estimating the EPE of the final model, after performing model selection.

Even if the method for selecting the best parameters or degree of complexity for a particular kind of model is determined, there is still a general challenge of picking what general class of models is most appropriate for a particular data set. The core aspect of choosing the right models for microbiome classification is to combine the knowledge of the most relevant constraints (e.g., data sparseness) inherent in the data with the understanding of the strengths and weaknesses of various approaches to supervised classification. If it is understood what structures will be inherent in the data, then models that take advantage of those structures will be chosen. For example, in the classification of microbiome, methods that can model nonlinear effects and complex interactions between organisms will be desired. In another example, the highly diverse nature of many microbial communities on the human body, models designed specifically to perform aggressive feature selection when faced with high-dimensional data will be most appropriate. Specialized generative models will be designed to incorporate prior knowledge about the data as well as the level of certainty about that prior knowledge. Instead of learning to predict class labels based on input features, a generative model will learn to predict the input features themselves. In other words, a generative model will learn what the data "looks like," regardless of the class labels. One potential benefit of generative models such as topic models and deep-layered belief nets will be that they can extract useful information even when the data are unlabeled. The ability to use data from related experiments to help build classifiers for one's own labeled data will be important as the number of publicly available microbial community data sets continues to grow.

Machine learning classification techniques will be applied to many types of microbial community data, for example, to the analysis of soil and sediment samples. For the soil and sediment samples, the samples will be classified according to environment type using support vector machines (SVMs) and k-nearest neighbors (KNN). Supervised learning will been used extensively in other classification domains with high-dimensional data, such as macroscopic ecology, microarray analysis, and text classification.

The goal of feature selection will be to find the combination of the model parameters and the feature subset that provides the lowest expected error on novel input data. Feature selection will be of utmost importance in the realm of microbiome classification due to the generally large number of features (i.e., constituent species-level taxa, or genes, or transcripts, or metabolites, or some combination of these): in addition to improving predictive accuracy, reducing the number of features leads to the production of more interpretable models. Approaches to feature selection are typically divided into three categories: filter methods, wrapper methods, and embedded methods.

As the simplest form of feature selection, filter methods are completely agnostic to the choice of learning algorithm being used; that is, they treat the classifier as a black box. Filter methods use a two-step process. First a univariate test (e.g. t-test) or multivariate test (e.g., a linear classifier built with each unique pair of features) will be performed to estimate the relevance of each feature, and (1) all features whose scores exceed a predetermined threshold will be selected or (2) the best n features for inclusion in the model will be selected; then a classifier on the reduced feature set will be run. The choice of n can be determined using a validation data set or cross-validation on the training set.

Filter methods have several benefits, including their low computational complexity, their ease of implementation, and their potential, in the case of multivariate filters, to identify important interactions between features. The fact that the filter has no knowledge about the classifier is advantageous in that it provides modularity, but it can also be disadvantageous, as there is no guarantee that the filter and the classifier will have the same optimal feature subsets. For example, a linear filter (e.g., correlation-based) is unlikely to choose an optimal feature subset for a nonlinear classifier such as an SVM or a random forest (RF).

The purpose of a filter will be to identify features that are generally predictive of the response variable, or to remove features that are noisy or uninformative. Common filters include, but are not limited to, the between-class $\chi^2$ test, information gain (decrease in entropy when the feature is removed), various standard classification performance measures such as precision, recall, and the F-measure, and the accuracy of a univariate classifier, and the bi-normal separation (BNS), which treats the univariate true positive rate and the false-positive rate (tpr, fpr, based on document presence/absence in text classification) as though they were cumulative probabilities from the standard normal cumulative distribution function, and the difference between their respective z-scores, $F^1$ (tpr)-$F^1$ (fpr), will be used as a measure of that variable's relevance to the classification task.

Wrapper methods are usually the most computationally intensive and perhaps the least elegant of the feature selection methods. A wrapper method, like a filter method, will treat the classifier as a black box, but instead of using a simple univariate or multivariate test to determine which features are important, a wrapper will use the classifier itself to evaluate subsets of features. This leads to a computationally intensive search: an ideal wrapper will retrain the classifier for all feature subsets, and will choose the one with the lowest validation error. Were this search tractable, wrappers would be superior to filters because they would be able to find the optimal combination of features and classifier parameters. The search will not be tractable for high-dimensional data sets; hence, the wrapper will use heuristics during the search to find the optimal feature subset. The use of a heuristic will limit the wrapper's ability to interact with the classifier for two reasons: the inherent lack of optimality of the search heuristic, and the compounded lack of optimality in cases where the wrapper's optimal feature set differs from that of the classifier. In many cases the main benefit of using wrappers instead of filters, namely that the wrapper can interact with the underlying classifier, is shared by embedded methods, and the additional computational cost incurred by wrappers therefore makes such methods unattractive.

Embedded approaches to feature selection will perform an integrated search over the joint space of model parameters and feature subsets so that feature selection becomes an integral part of the learning process. Embedded feature selection will have the advantage over filters that it has the opportunity to search for the globally optimal parameter-feature combination. This is because feature selection will be performed with knowledge of the parameter selection process, whereas filter and wrapper methods treat the classifier as a "black box." As discussed above, performing the search over the whole joint parameter-feature space is generally intractable, but embedded methods will use knowledge of the classifier structure to inform the search process, while in the other methods the classifier must be built from scratch for every feature set.

Industrial Use Examples

The method described herein will be useful in a plethora of industrial settings, examples provided below. The scope of the information obtained can vary, based on the type of industrial goal to be obtained. For example, the method can be applied on a macro scale, for example, sampling and analysis from all garment mills throughout the world. The method can also be applied on a regional scale, for example, sampling and analysis of garment mills in a region of the United States. Further, the method can be applied on a local scale, for example, sampling and analysis in a garment mill in South Carolina. Next, the method can be applied on a run-based scale, for example, sampling and analysis of a run of Levis 501™ jeans. The following examples are provided to illustrate various devices, tools, configurations and activities. These examples are for illustrative purposes, and should not be viewed as limiting, and do not otherwise limit, the scope of the present inventions.

Example 10

Figure 7:
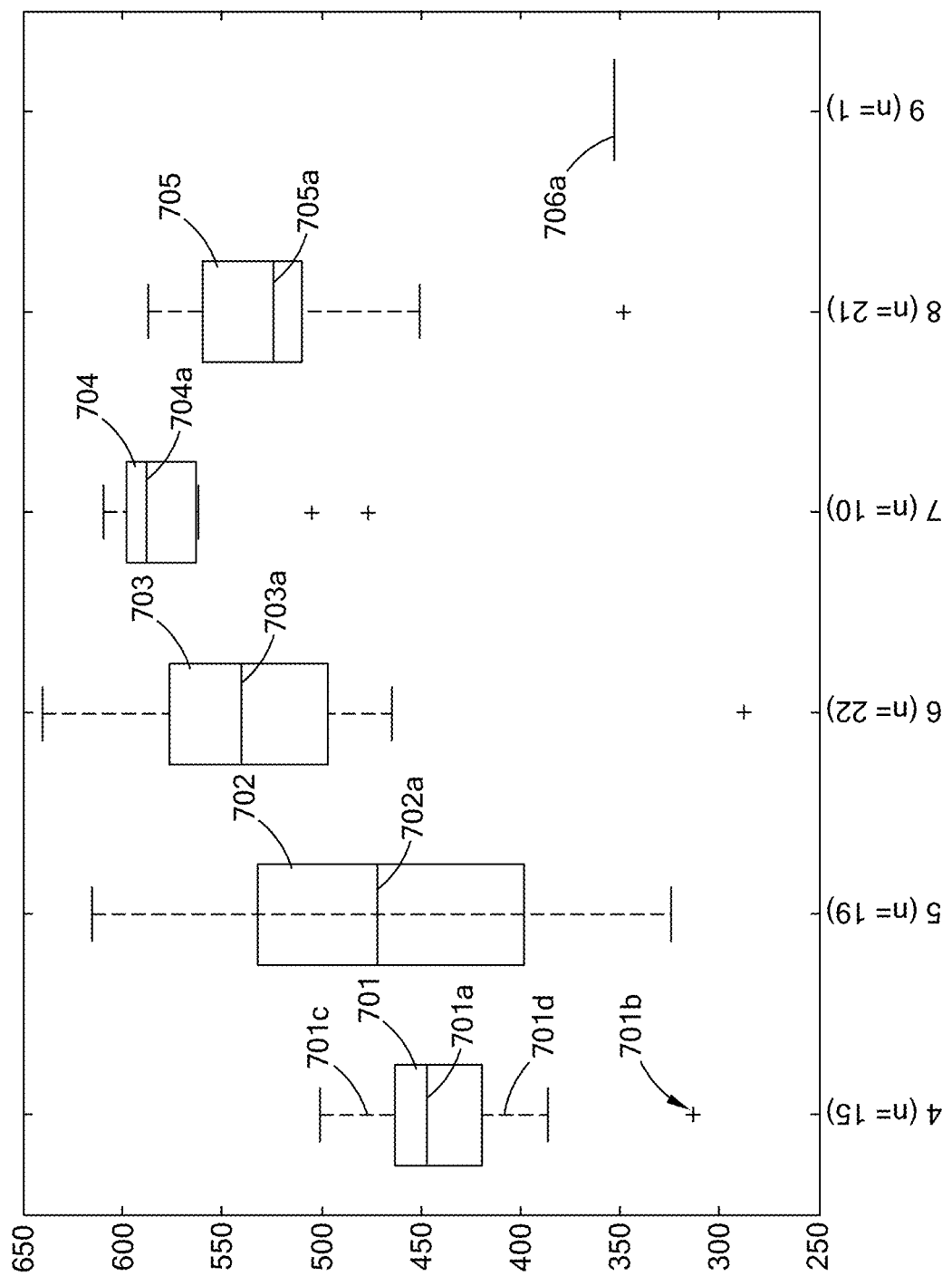
FIG. 7 is chart of an embodiment of the association of environmental parameters with microbial composition in accordance with the present inventions

In this example, two indices will be used to compare community-level bacterial richness across 88 different soils. First the number of observed OTUs will be computed, based on OTUs clustered with an open reference OTU picking protocol at the 97% sequence similarity level. The number of observed OTUs are shown in FIG. 7. The legend for FIG. 7 is the x axis is Soil pH; and the y-axis is Observed OTUs. The x-axis represents the number of OTUs observed (a measure of "alpha diversity"); the x-axis represents the pH of a soil sample; and each box 701, 702, 703, 704, 705, represents the distribution of number of OTUs observed in soils of the corresponding pH. The rectangles extend from the lower to upper quartile values of the data, with a lines 701*a*, 702*a*, 703*a*, 704*a*, 705*a*, 706*a* (pH with no distribution, n=1), at the median. The whiskers (dashed lines, e.g., 701*c*, 701*d*) extend from the box to 1.5 times the interquartile range. Outliers (those that are outside of 1.5 times the interquartile range) are the pluses, e.g., 701*b*, past the end of the whiskers. This plot illustrates that the number of OTUs peaks at neutral pH. This index of diversity is limited in that it characterizes diversity at only a single level of taxonomic resolution. Diversity will also be computed using Faith's index of phylogenetic diversity (Faith's PD), which provides an integrated index of the phylogenetic breadth contained within each community.

An example of the computation of the phylogenetic diversity is shown in FIG. 8. Thus, FIG. 8 is an embodiment of a graph of an embodiment of the association of environmental parameters with microbial composition across 88 soil samples included in a global survey of soil microbial diversity. The legend for FIG. 8 is the x-axis is Soil pH; and the y-axis is Phylogenetic Diversity. The y-axis represents the phylogenetic diversity observed (a measure of "alpha diversity"); the x-axis represents the pH of a soil sample; and each box 801, 802, 803, 804, 805, represents the distribution of the observed phylogenetic diversity in soils of the corresponding pH. The rectangles extend from the lower to upper quartile values of the data, with a lines 801*a*, 802*a*, 803*a*, 804*a*, 805*a*, 806*a* (pH with no distribution, n=1), at the median. The whiskers (dashed lines, e.g., 801*c*, 801*d*) extend from the box to 1.5 times the interquartile range. Outliers (those that are outside of 1.5 times the interquartile range) are the pluses, e.g., 803*d*, past the end of the whiskers. As in FIG. 7, this plot illustrates that the phylogenetic diversity peaks at neutral pH.

In both cases, the diversity metrics will be calculated for a randomly selected subset of the same number of sequences per soil sample, here 934, because diversity is unavoidably correlated with the number of sequences collected. The results of these analyses are presented in FIGS. 7-8, and both richness metrics show similar patterns in this specific case. By using a set number of sequences, general diversity patterns will be compared even if it is highly unlikely that the full extent of diversity was surveyed in each community.

Different metadata factors (pH and elevation, for example) and their effects on microbial community composition will be determined using UniFrac. As previously discussed, UniFrac quantifies the fraction of unique branch lengths against the total branch length between pairs of communities from one phylogenetic tree, giving an estimate of the phylogenetic distance between those communities. Separate neighbor-joining phylogenetic trees containing all of the bacterial will be generated with FastTree. Phylogenetic distances between the bacterial communities for each plot will be generated using weighted and unweighted UniFrac. Dendograms are among the available methods of viewing a tree.

Figure 9:
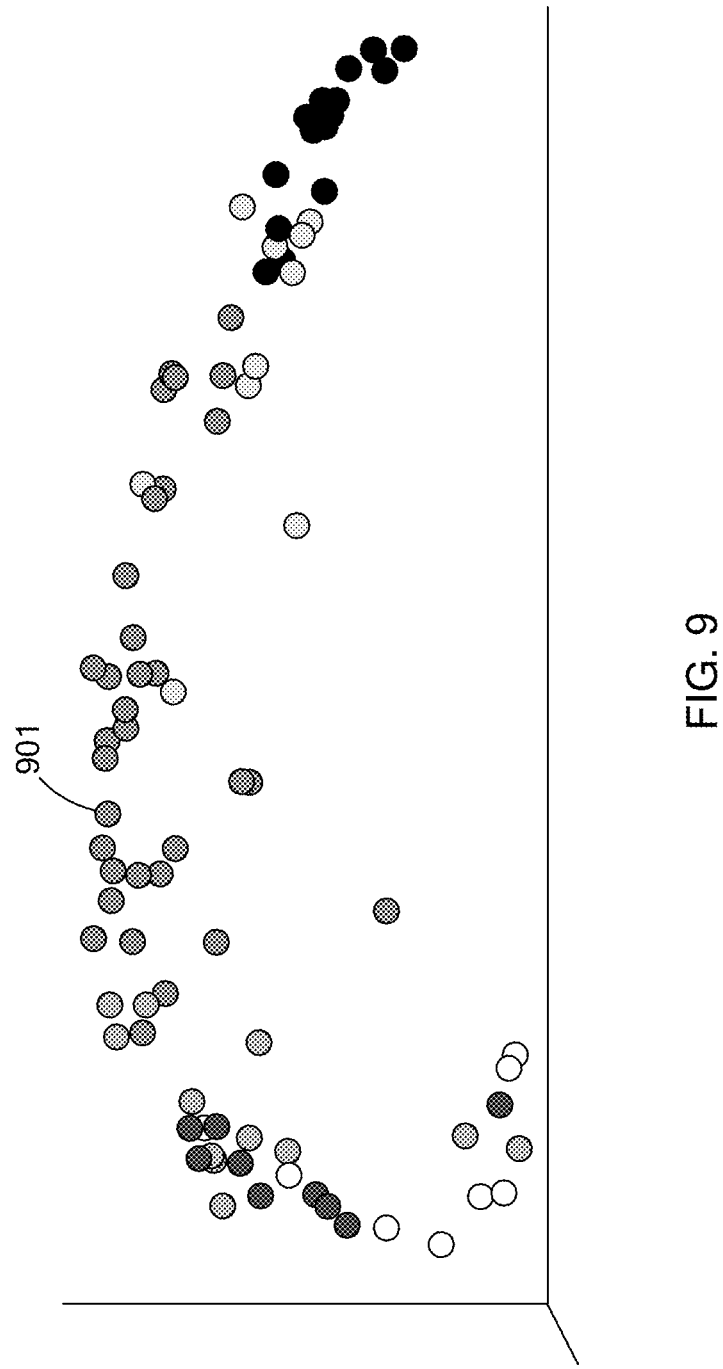
FIG. 9 is an embodiment of a Principal Coordinates (PCoA) plot in accordance with the present inventions.

The composition of bacterial communities was highly variable across the soils discussed in this example. On average, each pair of soils shared only 0.9% of their phylotypes (at the 97% similarity level), although this degree of community overlap is likely to be an underestimate given that not all phylotypes present in a given sample were identified. Visualization of the pairwise UniFrac distances on PCoA plots indicates significant variability within and across the biomes. Except for the desert soils and perhaps the soils from Mediterranean-type biomes, soils from similar biomes do not necessarily harbor similar bacterial communities, as the variability between biomes exceeded the variability within a given biome. This pattern was confirmed by a nonsignificant ANOSIM P value (P>0.05) for biome effects on UniFrac distances. FIG. 9 is a PCoA plot of the 88 soil samples included in this analysis with points colored by sample pH. It is clear that samples which are more similar in microbial composition (i.e., closer in space in the PCoA plot) are similar in pH.

FIG. 9 is an embodiment of a Principal Coordinates (PCoA) plot. Each point, e.g., 901, in this PCoA plot represented one of 88 soil samples included in a global survey of soil microbial diversity. Points that are closer in space are more similar in phylogenetic composition. Points are shown in varying color (grey scale for purposes of patent figure) based upon sample pH. It is clear that samples which are more similar in microbial composition (i.e., closer in space in the PCoA plot) are similar in pH. This illustrates one strategy that can be employed to associate overall phylogenetic composition with environmental information to identify parameters associated with, driving, or driven by microbial composition. This plot was generated using Emperor, an open source software package developed for the visualization of PCoA plots in the context of sample metadata, which supports exploratory data analysis such as this.

Figure 10:
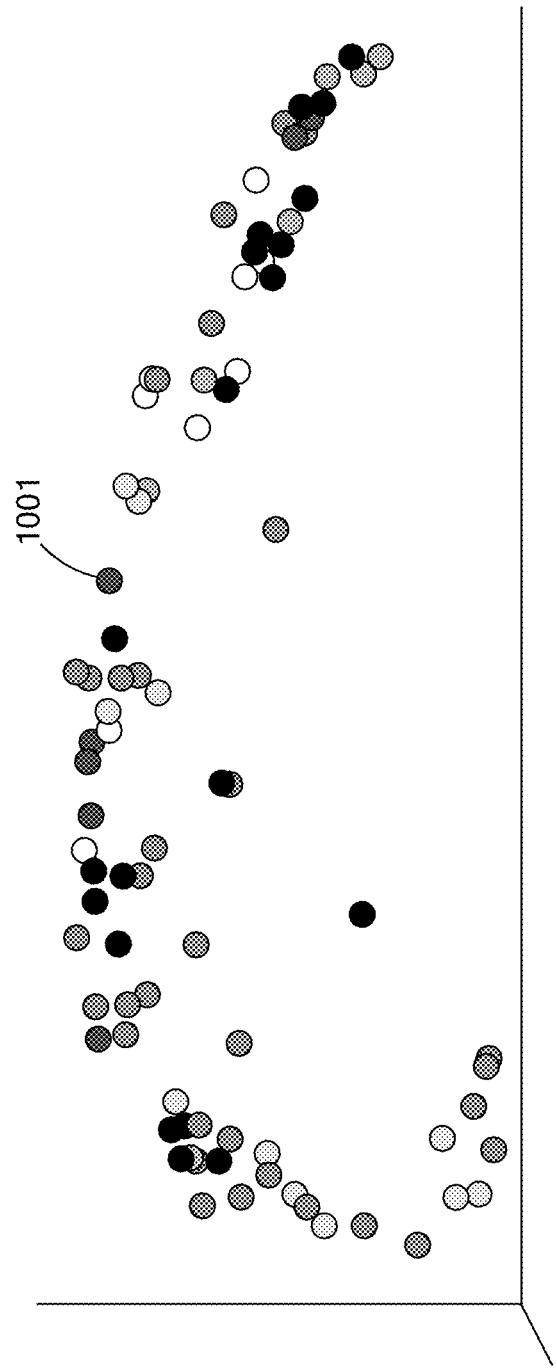
FIG. 10 is an embodiment of a Principal Coordinates (PCoA) plot in accordance with the present inventions.

FIG. 10 is an embodiment of a PCoA plot. Each point, e.g., 1001 in this PCoA plot represented one of 88 soil samples included in a global survey of soil microbial diversity. Points that are closer in space are more similar in phylogenetic composition. This is the same plot presented in FIG. 7 except that points are now colored (grey scale for purposes of patent figure) by the latitude at which the sample was collected, rather than pH. It is clear that samples which are more similar in microbial composition (i.e., closer in space in the PCoA plot) are not necessarily similar in latitude. When compared to FIG. 7, it is clear that pH is far more strongly associated with microbial composition than is latitude.

Of the edaphic soil characteristics measured, pH was most strongly correlated with the overall UniFrac distances between soils. UniFrac distances show minimal overlap among communities that differ by more than 2 pH units when samples are viewed by pH category as seen in FIG. 9. FIG. 10 shows the same PCoA plot, but with samples colored (grey scale for purposes of patent figures) by latitude. There does not appear to be an association between the latitude at which the sample was collected and its microbial composition. The plots are generated using Emperor, an open source software package developed for the visualization of PCoA plots in the context of sample metadata, which supports exploratory data analysis such as this.

Custom analyses with UniFrac will be done as well. The UniFrac and diversity metrics will be applied to specific lineages of bacteria (Acidobacteria, Actinobacteria, Alphaproteobacteria, Beta|Gammaproteobacteria, and Bacteroidetes). These lineage-specific analyses will be distinct from those described previously in that the diversity and phylogenetic composition of these individual taxa across the collected soils will be compared, not just the overall patterns evident from examining all taxa together. These five taxa will be the most abundant groups of bacteria in the total sequence dataset, these five taxonomic groups will be referred to as phyla, recognizing that the term "phyla" is being used in a general manner. The beta- and gammaproteobacterial groups will not be analyzed separately, as these groups are often combined in certain taxonomic schemes.

For the lineage-specific UniFrac analyses, the number of sequences will be limited to 250, 200, 100, 100, and 100 randomly selected sequences per soil for Acidobacteria, Alphaproteobacteria, Bacteroidetes, Beta/Gammaproteobacteria, and Actinobacteria, respectively. Normalizing the number of sequences per soil allows for control for the effects of survey effort (number of sequences per phylum per soil) in comparing the lineage-specific UniFrac distances across the sample set. Because some soils did not have the required number of sequences per phylum, these lineage-specific analyses will be conducted on only 57 to 69 of the 88 samples, excluding those soils where the individual phyla were relatively rare. From the lineage analysis, a gradient in the abundance of specific taxa was also present.

FIG. 11 is an illustration of an embodiment of microbiome composition. The y-axis is relative abundance of specific microbial phyla (a high-level taxonomic group; each phylum contains many bacterial species); the x-axis represents soil pH; and the colors (grey scale and simplified for purposes of patent figures) present different bacterial phyla.

For example these phyla include:
k_Bacteria;p_AD3
k_Bacteria;p_Acidobacteria
k_Bacteria;p_Actinobacteria
k_Bacteria;p_Armatimonadetes
k_Bacteria;p_BH180-139
k_Bacteria;p_BRCI
k_Bacteria;p_Bacteroidetes
k_Baeteria;p_Chlorobi
k_Bacteria;p_Chloroflexi
k_Bacteria;p_Cyanobacteria
k_Bacteria;p_Elusimicrobia
k_Bacteria;p_FBP
k_Bacteria;p_FCPU426
k_Bacteria;p_Fibrobacteres
k_Bacteria;p_Firmicutes
k_Bacteria;p_GAL15
k_Bacteria;p_GN02
k_Bacteria;p_Gemmatimonadetes
k_Bacteria;p._Kazan-3B-28
k_Bacteria;p._MVP-21
k_Bacteria;p_NC10
k_Bacteria;p_NKB19
k_Bacteria;p_Nitrospirae
k_Bacteria;p._ODI
k_Bacteria;p_OPII
k_Bacteria;p._0P3
k_Bacteria;p_0P8
k_Bacteria;p_Planctomycetes
k_Bacteria;p_Proteobacteria
k_Bacteria;p_SRI
k_Bacteria;p_Spirochaetes
k_Bacteria;p_TM6
k_Bacteria;p_TM7
Unassigned;Other
k_Bacteria;Other
k_Bacteria;p_

As seen in FIG. 11, each microbial taxon is denoted by a different color (e.g., area, 1101, 1102, 1103, 1104, 1105 for purposes of patent figures), with the x-axis representing increasing pH and the y-axis representing relative abundance. Some taxa change in a consistent way from low to high pH, for example, Acidobacteria is represented in area 1102. These consistent changes can drive the pattern in PCoA.

The phylogenetic approaches of UniFrac distances and Faith's PD are more powerful than standard OTU-based approaches where community structure and diversity are compared at a single level of sequence similarity because they take into account different levels of similarity between different pairs of taxa. In particular, comparing communities by grouping sequences into OTUs defined at the 97% similarity level has limitations in that such surveys will be far from comprehensive, and overarching patterns evident by comparing overall phylogenetic structure may be more difficult to discern and quantify.

Example 11

In the oil well setting, detailed metadata for each sample will be collected and compiled in a spreadsheet, database, or other system for organizing tabular or otherwise structured information. Text mining or other techniques may also be used to convert unstructured information into structured information for analysis, or the unstructured data may be analyzed directly. This metadata includes information about sample collection, the well and formation, chemical and physical characteristics of the fluid, and well productivity. Other associated metadata can be gathered from well logs, production, seismic, cores, etc. For each sample, general metadata requirements will include, but is not limited to: source well identifier; source formation identifier(s); collection source (wellhead or tank); collection date and time; collector name or identifier (to test for collector-specific patterns, which may indicate contamination); and method of collection (if more than one is used). For each well, general metadata requirements will include, but are not limited to: well history; previous experiments at that particular well; previous well identifiers that were affected by certain experiments maps; time in operation; physical characteristics of fluid, including pressure, temperature, and/or viscosity of the reservoir away from the wellbore and injection locations; chemical characteristics of fluid, including the concentrations and distributions of specific hydrocarbons, and other parameters previously collected; geological characteristics, including permeability, porosity, location of oil/water interface; production data, including volume of different hydrocarbons over time, rate of decline, different recovery operations (primary, secondary, tertiary recovery, etc.); indication of "strange" wells, or those that had surprising or unpredictable performance (for example, which wells stopped producing rapidly, did not meet productivity expectations, had unusual chemistries, physics, oil/water .changes, etc.). Determining the microbial communities will be helpful for an assortment of goals, for example, if the microbial profile varies as a function of pressure, temperature, and/or viscosity then it can be an indicator for reservoir rock/fluid conditions. Knowledge of these parameters can change the flow rates and pressure used in a flooding operating.

Example 12

Farmers rely heavily on the soil for the growth of their crops. With microbiome analysis of particular soil that yielded a successful crop season generally or a successful season for a particular crop, or that was especially resistant to climatic variation, a farmer will use this information to predict a number of things. First, the farmer will use the microbiome information from a successful soybean crop of the previous season and compare with the soil on his farm currently to see if the soil is likely to yield a successful soybean crop this season. Second, if the soil microbiome is much different, the farmer will use that information to plant a different crop that will flourish in the soil. This data will be obtained from previous years' soil analysis. Third, if the farmer is looking to expand his farm or purchase a different farm, the soil microbiome of the prospective farm will be tested to see which crops have growth potential in that particular soil. If the farmer desires to plant a specific crop, for example, soybeans, the analysis of the soil may steer him away from the new land if the microbiome of the soil is more likely to yield a successful season of a different crop, for example, corn. Fourth, a particular high-end crop or functional food in which the farmer is interested in cultivating may only grow in certain soil conditions. An analysis of the soil (including the microbiome) where the particular crop has thrived compared to the farmer's current soil will inform the farmer of the feasibility of the new crop.

Example 13

Cosmetics and skin care are significant industries. With men and woman looking for the fountain of youth, personalized formulas are desirable. Microbiome analysis of the particular consumer's face will lead to a personalized regiment of skincare, perfectly harmonized with that particular person's skin. For example, a particular microbiome may be associated with greasy skin. Greasy skin can lead to acne or other blemishes. A particular cream or serum with the microbiome of skin that is not greasy can be applied to the greasy-skin consumer, changing the skin of that consumer. In another example, a particular acne medication will be designed particularly for a consumer with a specific greasy skin microbiome in order to counteract both the acne and the skin condition, including the direct targeting of the acne-supporting community and indirect targeting of organisms that support that community especially where direct targeting does not work. In another example, the particular cream or make-up will be designed to maintain the microbiome of healthy glowing skin. These personalized cosmetic products will exploit the existence of a particular microbiome associated with particular types of skin. Therefore, a consumer will, through changing the microbiome of the skin, acquire the type of skin he or she desires.

Example 14

Animal husbandry refers to the practice of selectively breeding and raising livestock to promote desirable traits in animals for utility, sport, pleasure or research. It also refers to the efficient exploitation of species in agriculture in a manner that benefits all species involved in the relationship. The microbiome of the gut of the animal will be analyzed to dictate particularized breeding or raising of the livestock. For example, a cow may be having digestive issues, preventing it from absorbing nutrients. A healthy gut microbiome will be cultivated within the afflicted cow, restoring its digestion. In another example, the microbiome of the udder of a dairy cow will be analyzed to design, for example, a more nutrient-rich milk or milk that has a particular taste, or to transmit beneficial bacteria that prevent harmful bacteria from colonizing and souring the milk. The microbiome in the milk production area of the cow will be altered to produce the desired milk characteristics.

Example 15

The microbiome of a particular environment is different than that of other environments. The weather of a particular area will affect the microbiome of that area. For example, an area that used to receive abundant rainfall will have a gradually shifting microbiome corresponding to the gradual reduction of the rainfall to a drier environment. A continual analysis of a particular area is used in combination with other data, such as rainfall, temperature, UV index, etc., to enhance long range, extend prediction of weather patterns and changes.

Example 16

The microbiome of an oil patch is distinctive and that microbiome can be analyzed to predict where other oil patches may exist. To develop useful microbial sensors based on oil extracted from wells, essential baseline information about compositional differences of fluids across space and time must be collected. This is necessary to inform future studies of microbial communities at this site. For example, the studies will provide information about the intra-well temporal dynamics of microbial communities, and how those compositional differences relate to the inter-well and inter-formation differences and the associated characteristics, including productivity, of each well. The production zone that oil was extracted from when it reaches a wellbore will include production-zone-specific microbial indicators that, from an oil sample, could be used to indicate the source production zone. Microbial indicators of pressure, temperature, and/or viscosity that, from an oil sample, will be used to determine the pressure, temperature, and/or viscosity of the reservoir away from the wellbore and injection locations.

The predictive power of the microbiome analysis will be used to predict discrete variables and continuous variables. In another example, the microbiome indicators will provide information on primary production, when the location of the water/oil interface changes, so that the concentration of oil in the extract decreases. Microbial indicators of the location of or distance from the oil/water interface will indicate that the interface has shifted, or that the well is tapped. In another example, microbiome exploratory analysis will be used to determine what fluid/well parameters or production characteristics may be correlated with our microbial indicators. The low specificity, high sensitivity sweep for microbial indicators that are economically useful will provide preliminary data that can be used to perform more robust investigation in future sampling events.

Example 17

A constant question in space exploration is whether a given extraterrestrial environment can support life. Microbial life will be a very significant step in this exploration, whether or not independently evolved life may use DNA as its genetic material. Another angle to this research will be to bring microbiome samples to an environment in space to observe if the any particular microbiome or any particular part of a microbiome can survive the harsh environment. This will provide information about environments that may not be as harsh as others, and a potential environment for either housing life forms or being able to sustain life. In another example, constant sampling of particular surfaces in space and other celestial bodies will provide insight on the particular places where any microbiome is found. Additionally, defining the habitats that can support microbial life may have important implications for understanding and preventing biodegradation, such as that frequently occurring on the International Space Station.

Example 18

The pharmaceutical industry will benefit from microbiome predictive analysis. In a pharmaceutical manufacturing operation compositional differences between microbial communities residing on samples of drugs and/or their containers can be used to determine correct storage practices, counterfeit product, or point of manufacture.

Example 19

Many people are allergic to goods that are made in factories, for example, latex gloves. The microbiome of those individuals with allergies will be compared to those individuals with no allergies to a particular allergen. With the differences known, it will be possible to design and manufacture latex gloves that have certain characteristics that will prevent the allergic reaction based on the microbiome information. For example, the latex formulation may be adjusted to allow for the microbiome of the allergic patients to more closely match those of the non-allergic patient. In another example, particular harmless microorganisms may be placed on the latex gloves to prevent the allergic reaction.

It should be understood that the use of headings in this specification is for the purpose of clarity, and is not limiting in any way. Thus, the processes and disclosures described under a heading should be read in context with the entirely of this specification, including the various examples. The use of headings in this specification should not limit the scope of protection afford the present inventions. Thus, it should be understood that the teachings for one processes or apparatus, under one heading, and the teachings for the other processes or apparatus, under other headings, can be applicable to each other, as well as, being applicable to other sections and teachings in this specification, and vice versa.

The various embodiments of applications, methods, activities and operations set forth in this specification may be used for various other fields and for various other activities, uses and embodiments. Additionally, these embodiments, for example, may be used with: existing systems, articles, components, operations or activities; may be used with systems, articles, components, operations or activities that may be developed in the future; and with such systems, articles, components, operations or activities that may be modified, in-part, based on the teachings of this specification. Further, the various embodiments and examples set forth in this specification may be used with each other, in whole or in part, and in different and various combinations. Thus, for example, the configurations provided in the various embodiments and examples of this specification may be used with each other; and the scope of protection afforded the present inventions should not be limited to a particular embodiment, example, configuration or arrangement that is set forth in a particular embodiment, example, or in an embodiment in a particular Figure.

The inventions may be embodied in other forms than those specifically disclosed herein without departing from its spirit or essential characteristics. The described embodiments are to be considered in all respects only as illustrative and not restrictive.

What is claimed:

1. A computerized method comprising:
generating, using one or more computer processors, microbiome information from genetic material extracted from a first sample of a plurality samples sourced from a plurality of wells at a location associated with an industrial operation;
generating, using the one or more computer processors, microbiome information from genetic material extracted from a second sample of the plurality of samples;
selecting, using the one or more computer processors, a machine-learned model from a plurality of machine-learned models based on a testing of a predictive accuracy of the machine-learned model when applied to a plurality of subsets of the microbiome information from the genetic material extracted from the first sample, the selecting based on a class of the machine-learned model being a specialized generative model that was generated using an embedded approach to feature selection having knowledge of a parameter-selection process;
generating, using the one or more computer processors, predictive microbiome information corresponding to the microbiome information from the genetic material extracted from the second sample, the generating of the predictive microbiome information including applying the selected machine-learned model to the genetic material from the second sample, the predictive microbiome information relating to a source production zone corresponding to a hydrocarbon formation or a characteristic of a reservoir corresponding to the hydrocarbon formation, the characteristic including at least one of pressure, temperature, or viscosity; and
communicating, using the one or more computer processors, the predictive microbiome information relating to the source production zone or the characteristic of the reservoir for display in a user interface.

2. The method of claim 1, wherein at least a portion of the predictive microbiome information is displayed in a two dimensional plot.

3. The method of claim 1, wherein at least a portion of the predictive microbiome information is displayed in a three dimensional plot.

4. The method of claim 1, wherein non-genetic information corresponding to the predictive microbiome information is selected from a group consisting of temperature, GPS, pressure, depth, borehole true vertical depth, casing collar location, and viscosity, and the method further comprises communicating the non-genetic information for display in the user interface.

5. A method comprising:
selecting, using one or more computer processors, a machine-learned model from a plurality of machine-learned models based on a testing of a predictive accuracy of the machine-learned model when applied to a plurality of subsets of microbiome information from a genetic material extracted from a first sample, the selecting based on a class of the machine-learned model being a specialized generative model that was generated using an embedded approach to feature selection having knowledge of a parameter-selection process;
generating, using one or more computer processors, predictive microbiome information based on a nucleic acid sequencing data, the generating of the predictive microbiome information including applying a machine-learned model to the nucleic acid sequencing data, the predictive microbiome information predicting a productivity of each of a plurality of wells at a location based on intra-well temporal dynamics of microbial communities at the plurality of wells;
communicating, using the one or more computer processors, the predictive microbiome information for display in a user interface.

6. The method of claim 5, further comprising determining the intra-well and temporal dynamics based on real time microbiome information corresponding to the genetic material or an additional material.

7. The method of claim 5, further comprising determining the intra-well and temporal dynamics based on historic microbiome information corresponding to the genetic the material or an additional material.

8. The method of claim 5, wherein the plurality of wells is associated with an industrial operation selected from a group consisting of hydraulic fracturing and drilling a borehole.

9. The method of claim 5, further comprising determining the intra-well and temporal dynamics based on historic information and real time information corresponding to the genetic material or an additional material.

10. The method of claim 5, further comprising determining the intra-well and temporal dynamics is based on derived microbiome information and real time information corresponding to the genetic material or an additional material.

11. A method comprising:
performing operations at a computing system having one or more computer processors for communicating predictive microbiome information to a memory storage device for display in a human machine interface (HMI) of the memory storage device, the display having an interactive configuration for identifying patterns in the predictive microbiome information that are relevant to optimizing recovery of hydrocarbons, the operations comprising:
selecting, using the one or more computer processors, a machine-learned model from a plurality of machine-learned models based on a testing of a predictive accuracy of the machine-learned model when applied to a plurality of subsets of the microbiome information from a genetic material extracted from the first sample, the selecting based on a class of the machine-learned model being a specialized generative model that was generated using an embedded approach to feature selection having knowledge of a parameter-selection process;
generating, using the one or more computer processors, the predictive microbiome information, the predictive microbiome information corresponding to sequencing data extracted from genetic material from a second sample sourced at a well or an additional well, the generating of the predictive microbiome information including applying the selected machine-learned model to the sequencing data extracted from the genetic material from the second sample, the predictive microbiome information relating to a source production zone corresponding to a hydrocarbon formation or a characteristic of a reservoir corresponding to the hydrocarbon formation, the characteristic including at least one of pressure, temperature, or viscosity; and
performing, using the one or more computer processors, the communicating of the predictive microbiome information for the display in a user interface.

12. The method of claim 11, further comprising using computational analysis to subtract possible sources of contamination during collection of the first sample or the second sample.

13. The method of claim 11, further comprising communicating the predictive microbiome information for presentation in the user interface as n-dimensional space information.

14. The method of claim 11, wherein the predictive microbiome information further predicts a productivity based on information about temporal dynamics of microbial communities within the well or the additional well.

15. The method of claim 11, wherein the predictive microbiome information predicts inter-well and inter-formation differences between the well and the additional well.

16. The method of claim 11, wherein the predictive microbiome information pertains to a perforation and hydraulic fracturing plan to improve production.

17. The method of claim 11, further comprising storing the predictive microbiome information in auxiliary data structures for ready and efficient access.

18. The method of claim 17, wherein the auxiliary data structures include indexes or hashes.

19. The computerized method of claim 1, the user interface having an interactive configuration for visualizing patterns in the predictive microbiome information that are relevant to directing a recovery operation at the location, the interactive configuration including a plot using different colors for the predictive microbiome information and non-genetic information corresponding to the predictive microbiome information.

20. The method of claim 5, further comprising determining the intra-well spatial dynamics based on real time microbiome information corresponding to the genetic material or an additional material.

* * * * *